United States Patent
Concino et al.

(10) Patent No.: US 10,603,364 B2
(45) Date of Patent: Mar. 31, 2020

(54) LYSOSOMAL TARGETING AND USES THEREOF

(71) Applicant: Shire Human Genetic Therapies, Inc., Lexington, MA (US)

(72) Inventors: Michael F. Concino, Lexington, MA (US); Bettina Strack-Logue, Lexington, MA (US); Muthuraman Meiyappan, Lexington, MA (US); Angela W. Norton, Lexington, MA (US); Bohong Zhang, Lexington, MA (US); Andrea Iskenderian, Lexington, MA (US); Jianwen Feng, Lexington, MA (US); Kevin Holmes, Lexington, MA (US); Jing Pan, Lexington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

(21) Appl. No.: 15/503,227

(22) PCT Filed: Aug. 11, 2015

(86) PCT No.: PCT/US2015/044718
§ 371 (c)(1),
(2) Date: Feb. 10, 2017

(87) PCT Pub. No.: WO2016/025523
PCT Pub. Date: Feb. 18, 2016

(65) Prior Publication Data
US 2017/0246263 A1  Aug. 31, 2017

Related U.S. Application Data

(60) Provisional application No. 62/036,084, filed on Aug. 11, 2014.

(51) Int. Cl.
*A61K 38/47* (2006.01)
*C07K 14/475* (2006.01)
*C07K 16/18* (2006.01)
*A61K 47/64* (2017.01)
*C07K 14/705* (2006.01)
*C12N 9/24* (2006.01)

(52) U.S. Cl.
CPC .............. *A61K 38/47* (2013.01); *A61K 47/64* (2017.08); *C07K 14/475* (2013.01); *C07K 14/70571* (2013.01); *C07K 16/18* (2013.01); *C12N 9/2402* (2013.01); *C12Y 302/0105* (2013.01); *C07K 2319/06* (2013.01)

(58) Field of Classification Search
CPC ....................................................... C12N 9/14
USPC ........................................ 424/94.61; 435/197
See application file for complete search history.

(56) References Cited

U.S. PATENT DOCUMENTS

2011/0318327 A1* 12/2011 Concino .............. A61K 9/0085
424/94.61

FOREIGN PATENT DOCUMENTS

WO  WO 2011/163652 A2  12/2011
WO  WO 2012/122042 A2  9/2012

OTHER PUBLICATIONS

Petersen et al. JBC, vol. 272, No. 6, Issue of Feb. 7, pp. 3599-3605 (1997).*

* cited by examiner

*Primary Examiner* — Tekchand Saidha
(74) *Attorney, Agent, or Firm* — Proskauer Rose LLP; Fangli Chen

(57) ABSTRACT

The invention provides compositions and methods for effective lysosomal targeting mediated by SORT1. In particular, the compositions and methods provided by the invention may be used to treat lysosomal storage diseases such as Sanfilippo syndrome type B.

7 Claims, 44 Drawing Sheets

Specification includes a Sequence Listing.

SEQUENCE LISTING

```
<160> NUMBER OF SEQ ID NOS: 26

<210> SEQ ID NO 1
<211> LENGTH: 720
<212> TYPE: PRT
<213> ORGANISM: Homo sapiens

<400> SEQUENCE: 1

Asp Glu Ala Arg Glu Ala Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65                  70                  75                  80
```

-continued

```
Ser Gly Ser Gln Leu Arg Leu Pro Arg Pro Leu Pro Ala Val Pro Gly
                 85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
            115                 120                 125

Arg Glu Ile Asp Trp Met Ala Leu Asn Gly Ile Asn Leu Ala Leu Ala
        130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp
        195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
            260                 265                 270

Leu Arg Glu Leu Ile Lys Glu Phe Gly Thr Asp His Ile Tyr Gly Ala
        275                 280                 285

Asp Thr Phe Asn Glu Met Gln Pro Pro Ser Ser Glu Pro Ser Tyr Leu
    290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
            340                 345                 350

Gly Arg Leu Leu Val Leu Asp Leu Phe Ala Glu Ser Gln Pro Val Tyr
        355                 360                 365

Thr Arg Thr Ala Ser Phe Gln Gly Gln Pro Phe Ile Trp Cys Met Leu
    370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
            420                 425                 430

Ser Leu Met Ala Glu Leu Gly Trp Arg Lys Asp Pro Val Pro Asp Leu
        435                 440                 445

Ala Ala Trp Val Thr Ser Phe Ala Ala Arg Arg Tyr Gly Val Ser His
    450                 455                 460

Pro Asp Ala Gly Ala Ala Trp Arg Leu Leu Leu Arg Ser Val Tyr Asn
465                 470                 475                 480

Cys Ser Gly Glu Ala Cys Arg Gly His Asn Arg Ser Pro Leu Val Arg
                485                 490                 495
```

```
Arg Pro Ser Leu Gln Met Asn Thr Ser Ile Trp Tyr Asn Arg Ser Asp
            500                 505                 510

Val Phe Glu Ala Trp Arg Leu Leu Thr Ser Ala Pro Ser Leu Ala
    515                 520                 525

Thr Ser Pro Ala Phe Arg Tyr Asp Leu Leu Asp Leu Thr Arg Gln Ala
    530                 535                 540

Val Gln Glu Leu Val Ser Leu Tyr Glu Glu Ala Arg Ser Ala Tyr
545                 550                 555                 560

Leu Ser Lys Glu Leu Ala Ser Leu Leu Arg Ala Gly Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
            595                 600                 605

Glu Ala Glu Ala Asp Phe Tyr Glu Gln Asn Ser Arg Tyr Gln Leu Thr
            610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
            690                 695                 700

Lys Lys Ile Phe Leu Lys Tyr Tyr Pro Arg Trp Val Ala Gly Ser Trp
705                 710                 715                 720

<210> SEQ ID NO 2
<211> LENGTH: 743
<212> TYPE: PRT
<213> ORGANISM: Homo sapiens

<400> SEQUENCE: 2

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
            115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160
```

-continued

Gly Ile Asn Leu Ala Leu Ala Trp Ser Gly Gln Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

```
Glu Glu Ala Arg Ser Ala Tyr Leu Ser Lys Glu Leu Ala Ser Leu Leu
                580                 585                 590

Arg Ala Gly Gly Val Leu Ala Tyr Glu Leu Pro Ala Leu Asp Glu
            595                 600                 605

Val Leu Ala Ser Asp Ser Arg Phe Leu Leu Gly Ser Trp Leu Glu Gln
610                 615                 620

Ala Arg Ala Ala Ala Val Ser Glu Ala Glu Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
                660                 665                 670

Pro Arg Trp Arg Leu Phe Leu Glu Ala Leu Val Asp Ser Val Ala Gln
                675                 680                 685

Gly Ile Pro Phe Gln Gln His Gln Phe Asp Lys Asn Val Phe Gln Leu
                690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
                740

<210> SEQ ID NO 3
<211> LENGTH: 831
<212> TYPE: PRT
<213> ORGANISM: Homo sapiens

<400> SEQUENCE: 3

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
                20                  25                  30

Ser Gln Asp Arg Leu Asp Ala Pro Pro Pro Ala Ala Pro Leu Pro
            35                  40                  45

Arg Trp Ser Gly Pro Ile Gly Val Ser Trp Gly Leu Arg Ala Ala Ala
50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
                100                 105                 110

Ser Leu Ser Trp Val Gly Asp Ser Thr Gly Val Ile Leu Val Leu Thr
            115                 120                 125

Thr Phe His Val Pro Leu Val Ile Met Thr Phe Gly Gln Ser Lys Leu
130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
                180                 185                 190

Arg Gly Gly Arg Ile Phe Arg Ser Ser Asp Phe Ala Lys Asn Phe Val
            195                 200                 205
```

```
Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620
```

```
Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
            645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
            675                 680                 685

Val Glu Gln Pro Glu Leu Lys Gly His Asp Leu Glu Phe Cys Leu Tyr
            690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
            725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
            755                 760                 765

Val Thr Val Val Ala Gly Val Leu Ile Val Lys Lys Tyr Val Cys Gly
770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
            805                 810                 815

Asn Lys Ser Gly Tyr His Asp Ser Asp Glu Asp Leu Leu Glu
            820                 825                 830

<210> SEQ ID NO 4
<211> LENGTH: 44
<212> TYPE: PRT
<213> ORGANISM: Homo sapiens

<400> SEQUENCE: 4

Gln Asp Arg Leu Asp Ala Pro Pro Pro Ala Ala Pro Leu Pro Arg
1               5                   10                  15

Trp Ser Gly Pro Ile Gly Val Ser Trp Gly Leu Arg Ala Ala Ala
            20                  25                  30

Gly Gly Ala Phe Pro Arg Gly Arg Trp Arg Arg
            35                  40

<210> SEQ ID NO 5
<211> LENGTH: 593
<212> TYPE: PRT
<213> ORGANISM: Homo sapiens

<400> SEQUENCE: 5

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
            35                  40                  45

Trp Pro Thr Thr Leu Ser Arg His Leu Gly Gly Pro Cys Gln Val Asp
        50                  55                  60

Ala His Cys Ser Ala Gly His Ser Cys Ile Phe Thr Val Ser Gly Thr
65                  70                  75                  80
```

```
Ser Ser Cys Cys Pro Phe Pro Glu Ala Val Ala Cys Gly Asp Gly His
             85                  90                  95

His Cys Cys Pro Arg Gly Phe His Cys Ser Ala Asp Gly Arg Ser Cys
        100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Val Met Cys
            195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
            435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
```

```
                            500                 505                 510
His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
        530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 6
<211> LENGTH: 24
<212> TYPE: PRT
<213> ORGANISM: Homo sapiens

<400> SEQUENCE: 6

Thr Lys Cys Leu Arg Arg Glu Ala Pro Arg Trp Asp Ala Pro Leu Arg
1               5                   10                  15

Asp Pro Ala Leu Arg Gln Leu Leu
            20

<210> SEQ ID NO 7
<211> LENGTH: 524
<212> TYPE: PRT
<213> ORGANISM: Homo sapiens

<400> SEQUENCE: 7

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205
```

```
Gln Thr Ala Val Arg Thr Asn Ser Thr Phe Val Gln Ala Leu Val Glu
    210                 215                 220
His Val Lys Glu Glu Cys Asp Arg Leu Gly Pro Gly Met Ala Asp Ile
225                 230                 235                 240
Cys Lys Asn Tyr Ile Ser Gln Tyr Ser Glu Ile Ala Ile Gln Met Met
                245                 250                 255
Met His Met Gln Pro Lys Glu Ile Cys Ala Leu Val Gly Phe Cys Asp
            260                 265                 270
Glu Val Lys Glu Met Pro Met Gln Thr Leu Val Pro Ala Lys Val Ala
        275                 280                 285
Ser Lys Asn Val Ile Pro Ala Leu Glu Leu Val Glu Pro Ile Lys Lys
    290                 295                 300
His Glu Val Pro Ala Lys Ser Asp Val Tyr Cys Glu Val Cys Glu Phe
305                 310                 315                 320
Leu Val Lys Glu Val Thr Lys Leu Ile Asp Asn Asn Lys Thr Glu Lys
                325                 330                 335
Glu Ile Leu Asp Ala Phe Asp Lys Met Cys Ser Lys Leu Pro Lys Ser
            340                 345                 350
Leu Ser Glu Glu Cys Gln Glu Val Val Asp Thr Tyr Gly Ser Ser Ile
        355                 360                 365
Leu Ser Ile Leu Leu Glu Glu Val Ser Pro Glu Leu Val Cys Ser Met
    370                 375                 380
Leu His Leu Cys Ser Gly Thr Arg Leu Pro Ala Leu Thr Val His Val
385                 390                 395                 400
Thr Gln Pro Lys Asp Gly Gly Phe Cys Glu Val Cys Lys Lys Leu Val
                405                 410                 415
Gly Tyr Leu Asp Arg Asn Leu Glu Lys Asn Ser Thr Lys Gln Glu Ile
            420                 425                 430
Leu Ala Ala Leu Glu Lys Gly Cys Ser Phe Leu Pro Asp Pro Tyr Gln
        435                 440                 445
Lys Gln Cys Asp Gln Phe Val Ala Glu Tyr Glu Pro Val Leu Ile Glu
    450                 455                 460
Ile Leu Val Glu Val Met Asp Pro Ser Phe Val Cys Leu Lys Ile Gly
465                 470                 475                 480
Ala Cys Pro Ser Ala His Lys Pro Leu Leu Gly Thr Glu Lys Cys Ile
                485                 490                 495
Trp Gly Pro Ser Tyr Trp Cys Gln Asn Thr Glu Thr Ala Ala Gln Cys
            500                 505                 510
Asn Ala Val Glu His Cys Lys Arg His Val Trp Asn
    515                 520

<210> SEQ ID NO 8
<211> LENGTH: 120
<212> TYPE: PRT
<213> ORGANISM: Homo sapiens

<400> SEQUENCE: 8

Asp Gly Gly Phe Cys Glu Val Cys Lys Lys Leu Val Gly Tyr Leu Asp
1               5                   10                  15
Arg Asn Leu Glu Lys Asn Ser Thr Lys Gln Glu Ile Leu Ala Ala Leu
            20                  25                  30
Glu Lys Gly Cys Ser Phe Leu Pro Asp Pro Tyr Gln Lys Gln Cys Asp
        35                  40                  45
Gln Phe Val Ala Glu Tyr Glu Pro Val Leu Ile Glu Ile Leu Val Glu
```

```
                 50                  55                  60
Val Met Asp Pro Ser Phe Val Cys Leu Lys Ile Gly Ala Cys Pro Ser
 65                  70                  75                  80

Ala His Lys Pro Leu Leu Gly Thr Glu Lys Cys Ile Trp Gly Pro Ser
                 85                  90                  95

Tyr Trp Cys Gln Asn Thr Glu Thr Ala Ala Gln Cys Asn Ala Val Glu
            100                 105                 110

His Cys Lys Arg His Val Trp Asn
        115                 120
```

<210> SEQ ID NO 9
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

```
Gly Gly Gly Gly Gly Ala Ala Ala Ala Gly Gly Gly Gly
 1               5                  10
```

<210> SEQ ID NO 10
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

```
Gly Ala Pro
 1
```

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

```
Gly Gly Gly Gly Gly Pro
 1               5
```

<210> SEQ ID NO 12
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Gly Ala Pro Gly Gly Gly Gly Ala Ala Ala Gly Gly Gly Gly
 1               5                  10                  15

Gly Ala Pro Gly Gly Gly Gly Gly Ala Ala Ala Gly Gly Gly Gly
            20                  25                  30

Gly Ala Pro
        35
```

<210> SEQ ID NO 13
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Ala Pro Gly Gly Gly Gly Ala Ala Ala Ala
        35                  40                  45

Ala Gly Gly Gly Gly Gly Gly Ala Pro
    50                  55

<210> SEQ ID NO 14
<211> LENGTH: 2535
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
atggaggcgg tggcggtggc cgcggcggtg ggggtccttc tcctggccgg ggccggggc      60 gcggcaggcg acgaggcccg ggaggcggcg ccgtgcggg cgctcgtggc ccggctgctg     120
gggccaggcc ccgcggccga cttctccgtg tcggtggagc gcgctctggc tgccaagccg    180
ggcttggaca cctacagcct gggcggcggc ggcgcggcgc gcgtgcgggt gcgcggctcc    240
acgggcgtgg cggccgccgc ggggctgcac cgctacctgc gcgacttctg tggctgccac    300
gtggcctggt ccggctctca gctgcgcctg ccgcggccac tgccagccgt gccggggag    360 ctgaccgagg ccacgcccaa caggtaccgc tattaccaga atgtgtgcac gcaaagctac    420
tccttcgtgt ggtgggactg ggcccgctgg gagcgagaga tagactggat ggcgctgaat    480
ggcatcaacc tggcactggc ctggagcggc caggaggcca tctggcagcg ggtgtacctg    540
gccttgggcc tgacccaggc agagatcaat gagttccttta ctggtcctgc cttcctggcc    600 tggggggcgaa tggcaacct gcacacctgg gatggccccc tgccccctc ctggcacatc    660 aagcagcttt acctgcagca ccgggtcctg accagatgc gctccttcgg catgaccccca    720 gtgctgcctg cattcgcggg gcatgttccc gaggctgtca ccagggtgtt ccctcaggtc    780
aatgtcacga agatgggcag ttggggccac tttaactgtt cctactcctg ctccttcctt    840
ctggctccgg aagaccccat attccccatc atcgggagcc tcttcctgcg agagctgatc    900
aaagagtttg gcacagacca catctatggg gccgacactt tcaatgagat gcagccacct    960
tcctcagagc cctcctacct tgccgcagcc accactgccg tctatgaggc catgactgca   1020
gtggatactg aggctgtgtg gctgctccaa ggctggctct ccagcacca gccgcagttc   1080 tggggccccg cccagatcag ggctgtgctg ggagctgtgc ccgtggccg cctcctggtt   1140 ctggacctgt ttgctgagag ccagcctgtg tatacccgca ctgcctcctt ccagggccag   1200
cccttcatct ggtgcatgct gcacaacttt gggggaaacc atggtctttt tggagcccta   1260
```

```
gaggctgtga acggaggccc agaagctgcc cgcctcttcc ccaactccac catggtaggc      1320
acgggcatgg cccccgaggg catcagccag aacgaagtgg tctattccct catggctgag      1380
ctgggctggc gaaaggaccc agtgccagat ttggcagcct gggtgaccag ctttgccgcc      1440
cggcggtatg gggtctccca cccggacgca ggggcagcgt ggaggctact gctccggagt      1500
gtgtacaact gctccgggga ggcctgcagg ggccacaatc gtagcccgct ggtcaggcgg      1560
ccgtccctac agatgaatac cagcatctgg tacaaccgat ctgatgtgtt tgaggcctgg      1620
cggctgctgc tcacatctgc tccctccctg gccaccagcc ccgccttccg ctacgacctg      1680
ctggacctca ctcggcaggc agtgcaggag ctggtcagct tgtactatga ggaggcaaga      1740
agcgcctacc tgagcaagga gctggcctcc ctgttgaggg ctggaggcgt cctggcctat      1800
gagctgctgc cggcactgga cgaggtgctg gctagtgaca gccgcttctt gctgggcagc      1860
tggctagagc aggcccgagc agcggcagtc agtgaggccg aggccgattt ctacgagcag      1920
aacagccgct accagctgac cttgtggggg ccagaaggca acatcctgga ctatgccaac      1980
aagcagctgg cggggttggt ggccaactac tacaccccct gctggcggct tttcctggag      2040
gcgctggttg acagtgtggc ccagggcatc cctttccaac agcaccagtt tgacaaaaat      2100
gtcttccaac tggagcaggc cttcgttctc agcaagcaga ggtaccccag ccagccgcga      2160
ggagacactg tggacctggc caagaagatc ttcctcaaat attaccccg ctgggtggcc       2220 ggctcttggg gcgcgccagg aggcggagga ggcgccgctg ctgcagccgg aggtggggc       2280 ggaggcgctc ctggaggcgg cggggagcc gctgccgctg caggaggagg tggcggaggt       2340
gcgcctggcg gagggggagg cgctgcagct gccgccggag gaggggcgg cggagctcct       2400 caggaccggc tggacgcgcc gccgccgccc gctgcgccgc tgccgcgctg gtctggcccc      2460
atcggggtga ctgggggct gcgggcggcc gcagccgggg gcgcgtttcc ccgcggcggc       2520
cgttggcgtc gctag                                                       2535

<210> SEQ ID NO 15
<211> LENGTH: 2475
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
atggaggcgg tggcggtggc cgcggcggtg ggggtccttc tcctggccgg ggccgggggc        60
gcggcaggcg acgaggcccg ggaggcggcg gccgtgcggg cgctcgtggc ccggctgctg       120
gggccaggcc ccgcggccga cttctccgtg tcggtggagc gcgctctggc tgccaagccg       180
ggcttggaca cctacagcct gggcggcggc ggcgcggcgc gcgtgcgggt gcgcggctcc       240 acggcgtgg cggccgccgc ggggctgcac cgctacctgc gcgacttctg tggctgccac       300
gtggcctggt ccgctctca gctgcgcctg ccgcggccac tgccagccgt gccggggag       360 ctgaccgagg ccacgcccaa caggtaccgc tattaccaga atgtgtgcac gcaaagctac      420
tccttcgtgt ggtgggactg ggccgcctgg agcgagagaa tagactggat ggcgctgaat       480
ggcatcaacc tggcactggc ctggagcggc caggaggcca tctggcagcg ggtgtacctg       540
gccttgggcc tgacccaggc agagatcaat gagttcttta ctggtcctgc cttcctggcc       600
tgggggcgaa tggcaaacct gcacacctgg gatggccccc tgccccccte ctggcacatc       660 aagcagcttt acctgcagca ccgggtcctg gaccagatgc gctccttcgg catgacccca      720
```

| | |
|---|---|
| gtgctgcctg cattcgcggg gcatgttccc gaggctgtca ccagggtgtt ccctcaggtc | 780 |
| aatgtcacga agatgggcag ttggggccac tttaactgtt cctactcctg ctccttcctt | 840 |
| ctggctccgg aagacccat attccccatc atcgggagcc tcttcctgcg agagctgatc | 900 |
| aaagagtttg gcacagacca catctatggg gccgacactt tcaatgagat gcagccacct | 960 |
| tcctcagagc cctcctacct tgccgcagcc accactgccg tctatgaggc catgactgca | 1020 |
| gtggatactg aggctgtgtg gctgctccaa ggctggctct tccagcacca gccgcagttc | 1080 |
| tgggggcccg cccagatcag ggctgtgctg ggagctgtgc ccgtggccg cctcctggtt | 1140 |
| ctggacctgt ttgctgagag ccagcctgtg tatacccgca ctgcctcctt ccagggccag | 1200 |
| cccttcatct ggtgcatgct gcacaacttt gggggaaacc atggtctttt tggagcccta | 1260 |
| gaggctgtga acgaggccc agaagctgcc cgcctcttcc ccaactccac catggtaggc | 1320 |
| acgggcatgg cccccgaggg catcagccag aacgaagtgg tctattccct catggctgag | 1380 |
| ctgggctggc gaaaggaccc agtgccagat ttggcagcct gggtgaccag ctttgccgcc | 1440 |
| cggcggtatg gggtctccca cccggacgca ggggcagcgt ggaggctact gctccggagt | 1500 |
| gtgtacaact gctccgggga ggcctgcagg ggccacaatc gtagcccgct ggtcaggcgg | 1560 |
| ccgtccctac agatgaatac cagcatctgg tacaaccgat ctgatgtgtt tgaggcctgg | 1620 |
| cggctgctgc tcacatctgc tccctccctg gccaccagcc ccgccttccg ctacgacctg | 1680 |
| ctggacctca ctcggcaggc agtgcaggag ctggtcagct tgtactatga ggaggcaaga | 1740 |
| agcgcctacc tgagcaagga gctggcctcc ctgttgaggg ctggaggcgt cctggcctat | 1800 |
| gagctgctgc cggcactgga cgaggtgctg gctagtgaca gccgcttctt gctgggcagc | 1860 |
| tggctagagc aggcccgagc agcggcagtc agtgaggccg aggccgattt ctacgagcag | 1920 |
| aacagccgct accagctgac cttgtggggg ccagaaggca acatcctgga ctatgccaac | 1980 |
| aagcagctgg cggggttggt ggccaactac tacaccccctc gctggcggct tttcctggag | 2040 |
| gcgctggttg acagtgtggc ccagggcatc cctttccaac agcaccagtt tgacaaaaat | 2100 |
| gtcttccaac tggagcaggc cttcgttctc agcaagcaga ggtacccag ccagccgcga | 2160 |
| ggagacactg tggacctggc caagaagatc ttcctcaaat attaccccg ctgggtggcc | 2220 |
| ggctcttggg gcgcgccagg aggcggagga ggcgccgctg ctgcagccgg aggtgggggc | 2280 |
| ggaggcgctc ctggaggcgg cggggagcc gctgccgctg caggaggagg tggcggaggt | 2340 |
| gcgcctggcg gagggggagg cgctgcagct gccgccggag gaggggcgg cggagctcct | 2400 |
| accaagtgtt tgcgcaggga ggccccgcgc tgggacgccc ctttgaggga cccagccttg | 2460 |
| agacagctgc tgtga | 2475 |

<210> SEQ ID NO 16
<211> LENGTH: 2763
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

| | |
|---|---|
| atggaggcgg tggcggtggc cgcggcggtg ggggtccttc tcctggccgg ggccgggggc | 60 |
| gcggcaggcg acgaggcccg ggaggcggcg ccgtgcggg cgctcgtggc ccggctgctg | 120 |
| gggccaggcc ccgcggccga cttctccgtg tcggtggagc gcgctctggc tgccaagccg | 180 |

```
ggcttggaca cctacagcct gggcggcggc ggcgcggcgc gcgtgcgggt gcgcggctcc    240
acgggcgtgg cggccgccgc ggggctgcac cgctacctgc gcgacttctg tggctgccac    300
gtggcctggt ccggctctca gctgcgcctg ccgcggccac tgccagccgt gccggggag    360 ctgaccgagg ccacgcccaa caggtaccgc tattaccaga atgtgtgcac gcaaagctac    420
tccttcgtgt ggtgggactg ggcccgctgg gagcgagaga tagactggat ggcgctgaat    480
ggcatcaacc tggcactggc ctggagcggc caggaggcca tctggcagcg ggtgtacctg    540
gccttgggcc tgacccaggc agagatcaat gagttcttta ctggtcctgc cttcctggcc    600
tgggggcgaa tggcaacct gcacacctgg gatggccccc tgcccccctc ctggcacatc    660
aagcagcttt acctgcagca ccgggtcctg gaccagatgc gctccttcgg catgacccca    720
gtgctgcctg cattcgcggg gcatgttccc gaggctgtca ccagggtgtt ccctcaggtc    780
aatgtcacga agatgggcag ttggggccac tttaactgtt cctactcctg ctccttcctt    840
ctggctccgg aagaccccat attccccatc atcgggagcc tcttcctgcg agagctgatc    900
aaagagtttg gcacagacca catctatggg ccgacacttt caatgagat gcagccacct    960 tcctcagagc cctcctacct tgccgcagcc accactgccg tctatgaggc catgactgca   1020
gtggatactg aggctgtgtg gctgctccaa ggctggctct ccagcacca gccgcagttc   1080 tgggggcccg cccagatcag gctgtgctg ggagctgtgc cccgtggccg cctcctggtt   1140
ctggacctgt ttgctgagag ccagcctgtg tatacccgca ctgcctcctt ccagggccag   1200
cccttcatct ggtgcatgct gcacaacttt ggggaaacc atggtctttt tggagcccta   1260
gaggctgtga acgaggccc agaagctgcc cgcctcttcc ccaactccac catggtaggc   1320
acgggcatgg cccccgaggg catcagccag aacgaagtgg tctattccct catggctgag   1380
ctgggctggc gaaaggaccc agtgccagat ttggcagcct gggtgaccag ctttgccgcc   1440
cggcggtatg gggtctccca cccggacgca ggggcagcgt ggaggctact gctccggagt   1500
gtgtacaact gctccgggga ggcctgcagg ggccacaatc gtagcccgct ggtcaggcgg   1560
ccgtccctac agatgaatac cagcatctgg tacaaccgat ctgatgtgtt tgaggcctgg   1620
cggctgctgc tcacatctgc tccctccctg gccaccagcc ccgccttccg ctacgacctg   1680
ctggacctca ctcggcaggc agtgcaggag ctggtcagct tgtactatga ggaggcaaga   1740
agcgcctacc tgagcaagga gctggcctcc ctgttgaggg ctggaggcgt cctggcctat   1800
gagctgctgc cggcactgga cgaggtgctg gctagtgaca gccgcttctt gctgggcagc   1860
tggctagagc aggcccgagc agcggcagtc agtgaggccg aggccgattt ctacgagcag   1920
aacagccgct accagctgac cttgtggggg ccagaaggca acatcctgga ctatgccaac   1980
aagcagctgg cggggttggt ggccaactac tacacccctc gctggcggct tttcctggag   2040
gcgctggttg acagtgtggc ccagggcatc cctttccaac agcaccagtt tgacaaaaat   2100
gtcttccaac tggagcaggc cttcgttctc agcaagcaga ggtaccccag ccagccgcga   2160
ggagacactg tggacctggc caagaagatc ttcctcaaat attaccccg ctgggtggcc   2220 ggctcttggg gcgcgccagg aggcggagga ggcgccgctg ctgcagccgg aggtgggggc   2280
ggaggcgctc ctggaggcgg cggggagcc gctgccgctg caggaggagg tggcggaggt   2340
gcgcctggcg gaggggagg cgctgcagct gccgccggag gagggggcgg cggagctcct   2400
gacggtggct tctgcgaagt gtgcaagaag ctggtggggtt atttggatcg caacctggag   2460
aaaaacagca ccaagcagga gatcctggct gctcttgaga aaggctgcag cttcctgcca   2520
gacccttacc agaagcagtg tgatcagttt gtggcagagt acgagcccgt gctgatcgag   2580
```

-continued

```
atcctggtgg aggtgatgga tccttccttc gtgtgcttga aaattggagc ctgcccctcg    2640
gcccataagc ccttgttggg aactgagaag tgtatatggg gcccaagcta ctggtgccag    2700
aacacagaga cagcagccca gtgcaatgct gtcgagcatt gcaaacgcca tgtgtggaac    2760
tag                                                                  2763
```

<210> SEQ ID NO 17
<211> LENGTH: 844
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
                35                  40                  45

Ser Val Ser Val Glu Arg Ala Leu Ala Ala Lys Pro Gly Leu Asp Thr
    50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
                115                 120                 125

Tyr Arg Tyr Tyr Gln Asn Val Cys Thr Gln Ser Tyr Ser Phe Val Trp
                130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
                180                 185                 190

Phe Thr Gly Pro Ala Phe Leu Ala Trp Gly Arg Met Gly Asn Leu His
                195                 200                 205

Thr Trp Asp Gly Pro Leu Pro Pro Ser Trp His Ile Lys Gln Leu Tyr
                210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
                275                 280                 285

Pro Ile Ile Gly Ser Leu Phe Leu Arg Glu Leu Ile Lys Glu Phe Gly
                290                 295                 300

Thr Asp His Ile Tyr Gly Ala Asp Thr Phe Asn Glu Met Gln Pro Pro
```

```
            305                 310                 315                 320
Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Gln Gly Trp
                340                 345                 350

Leu Phe Gln His Gln Pro Gln Phe Trp Pro Ala Gln Ile Arg Ala
                355                 360                 365

Val Leu Gly Ala Val Pro Arg Gly Arg Leu Leu Val Leu Asp Leu Phe
            370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
                420                 425                 430

Phe Pro Asn Ser Thr Met Val Gly Thr Gly Met Ala Pro Glu Gly Ile
                435                 440                 445

Ser Gln Asn Glu Val Val Tyr Ser Leu Met Ala Glu Leu Gly Trp Arg
                450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
                500                 505                 510

Asn Arg Ser Pro Leu Val Arg Arg Pro Ser Leu Gln Met Asn Thr Ser
                515                 520                 525

Ile Trp Tyr Asn Arg Ser Asp Val Phe Glu Ala Trp Arg Leu Leu Leu
                530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
                580                 585                 590

Arg Ala Gly Gly Val Leu Ala Tyr Glu Leu Leu Pro Ala Leu Asp Glu
                595                 600                 605

Val Leu Ala Ser Asp Ser Arg Phe Leu Leu Gly Ser Trp Leu Glu Gln
                610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
                660                 665                 670

Pro Arg Trp Arg Leu Phe Leu Glu Ala Leu Val Asp Ser Val Ala Gln
                675                 680                 685

Gly Ile Pro Phe Gln Gln His Gln Phe Asp Lys Asn Val Phe Gln Leu
                690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735
```

```
Arg Trp Val Ala Gly Ser Trp Gly Ala Pro Gly Gly Gly Gly Ala
            740                 745                 750

Ala Ala Ala Ala Gly Gly Gly Gly Gly Ala Pro Gly Gly Gly Gly
            755                 760                 765

Gly Ala Ala Ala Ala Gly Gly Gly Gly Ala Pro Gly Gly
            770                 775             780

Gly Gly Gly Ala Ala Ala Ala Gly Gly Gly Gly Gly Ala Pro
785                 790                 795                 800

Gln Asp Arg Leu Asp Ala Pro Pro Pro Ala Ala Pro Leu Pro Arg
            805                 810                 815

Trp Ser Gly Pro Ile Gly Val Ser Trp Gly Leu Arg Ala Ala Ala
            820                 825                 830

Gly Gly Ala Phe Pro Arg Gly Gly Arg Trp Arg Arg
            835                 840

<210> SEQ ID NO 18
<211> LENGTH: 824
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
            20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
            50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
            85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
            115                 120                 125

Tyr Arg Tyr Tyr Gln Asn Val Cys Thr Gln Ser Tyr Ser Phe Val Trp
            130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
            165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
            195                 200                 205

Thr Trp Asp Gly Pro Leu Pro Pro Ser Trp His Ile Lys Gln Leu Tyr
            210                 215                 220

Leu Gln His Arg Val Leu Asp Gln Met Arg Ser Phe Gly Met Thr Pro
225                 230                 235                 240
```

Val Leu Pro Ala Phe Ala Gly His Val Pro Glu Ala Val Thr Arg Val
                    245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr

```
                        660                 665                 670
Pro Arg Trp Arg Leu Phe Leu Glu Ala Leu Val Asp Ser Val Ala Gln
            675                 680                 685

Gly Ile Pro Phe Gln Gln His Gln Phe Asp Lys Asn Val Phe Gln Leu
        690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Gly Gly Gly Gly Gly Ala
            740                 745                 750

Ala Ala Ala Gly Gly Gly Gly Gly Ala Pro Gly Gly Gly
        755                 760                 765

Gly Ala Ala Ala Ala Gly Gly Gly Gly Ala Pro Gly Gly
        770                 775                 780

Gly Gly Gly Ala Ala Ala Ala Gly Gly Gly Gly Gly Ala Pro
785                 790                 795                 800

Thr Lys Cys Leu Arg Arg Glu Ala Pro Arg Trp Asp Ala Pro Leu Arg
            805                 810                 815

Asp Pro Ala Leu Arg Gln Leu Leu
            820

<210> SEQ ID NO 19
<211> LENGTH: 920
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Ala Ala Arg Val Arg Val Arg Gly Ser
65              70                  75                  80

Thr Gly Val Ala Ala Ala Ala Gly Leu His Arg Tyr Leu Arg Asp Phe
            85                  90                  95

Cys Gly Cys His Val Ala Trp Ser Gly Ser Gln Leu Arg Leu Pro Arg
        100                 105                 110

Pro Leu Pro Ala Val Pro Gly Glu Leu Thr Glu Ala Thr Pro Asn Arg
    115                 120                 125

Tyr Arg Tyr Tyr Gln Asn Val Cys Thr Gln Ser Tyr Ser Phe Val Trp
130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
            165                 170                 175

Arg Val Tyr Leu Ala Leu Gly Leu Thr Gln Ala Glu Ile Asn Glu Phe
        180                 185                 190
```

```
Phe Thr Gly Pro Ala Phe Leu Ala Trp Gly Arg Met Gly Asn Leu His
    195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
            290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
            370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
            450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
            530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605
```

```
Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Gly Gly Gly Gly Gly Ala
            740                 745                 750

Ala Ala Ala Ala Gly Gly Gly Gly Gly Ala Pro Gly Gly Gly Gly
        755                 760                 765

Gly Ala Ala Ala Ala Gly Gly Gly Gly Gly Ala Pro Gly Gly
    770                 775                 780

Gly Gly Gly Ala Ala Ala Ala Gly Gly Gly Gly Gly Ala Pro
785                 790                 795                 800

Asp Gly Gly Phe Cys Glu Val Cys Lys Lys Leu Val Gly Tyr Leu Asp
                805                 810                 815

Arg Asn Leu Glu Lys Asn Ser Thr Lys Gln Glu Ile Leu Ala Ala Leu
            820                 825                 830

Glu Lys Gly Cys Ser Phe Leu Pro Asp Pro Tyr Gln Lys Gln Cys Asp
        835                 840                 845

Gln Phe Val Ala Glu Tyr Glu Pro Val Leu Ile Glu Ile Leu Val Glu
    850                 855                 860

Val Met Asp Pro Ser Phe Val Cys Leu Lys Ile Gly Ala Cys Pro Ser
865                 870                 875                 880

Ala His Lys Pro Leu Leu Gly Thr Glu Lys Cys Ile Trp Gly Pro Ser
                885                 890                 895

Tyr Trp Cys Gln Asn Thr Glu Thr Ala Ala Gln Cys Asn Ala Val Glu
            900                 905                 910

His Cys Lys Arg His Val Trp Asn
        915                 920

<210> SEQ ID NO 20
<211> LENGTH: 860
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
```

```
            35                  40                  45
Ser Val Ser Val Glu Arg Ala Leu Ala Ala Lys Pro Gly Leu Asp Thr
 50                  55                  60

Tyr Ser Leu Gly Gly Gly Ala Ala Arg Val Arg Val Arg Gly Ser
 65                  70                  75                  80

Thr Gly Val Ala Ala Ala Gly Leu His Arg Tyr Leu Arg Asp Phe
                     85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
                115                 120                 125

Tyr Arg Tyr Tyr Gln Asn Val Cys Thr Gln Ser Tyr Ser Phe Val Trp
130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
                180                 185                 190

Phe Thr Gly Pro Ala Phe Leu Ala Trp Gly Arg Met Gly Asn Leu His
                195                 200                 205

Thr Trp Asp Gly Pro Leu Pro Pro Ser Trp His Ile Lys Gln Leu Tyr
210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
                275                 280                 285

Pro Ile Ile Gly Ser Leu Phe Leu Arg Glu Leu Ile Lys Glu Phe Gly
                290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
                340                 345                 350

Leu Phe Gln His Gln Pro Gln Phe Trp Gly Pro Ala Gln Ile Arg Ala
                355                 360                 365

Val Leu Gly Ala Val Pro Arg Gly Arg Leu Leu Val Leu Asp Leu Phe
                370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
                420                 425                 430

Phe Pro Asn Ser Thr Met Val Gly Thr Gly Met Ala Pro Glu Gly Ile
                435                 440                 445

Ser Gln Asn Glu Val Val Tyr Ser Leu Met Ala Glu Leu Gly Trp Arg
                450                 455                 460
```

```
Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Gly Gly Gly Gly Gly Ala
            740                 745                 750

Ala Ala Ala Ala Gly Gly Gly Gly Ala Pro Gly Gly Gly Gly
        755                 760                 765

Gly Ala Ala Ala Ala Gly Gly Gly Gly Gly Ala Pro Gly Gly
        770                 775                 780

Gly Gly Gly Ala Ala Ala Ala Gly Gly Gly Gly Gly Ala Pro
785                 790                 795                 800

Leu Cys Gly Gly Glu Leu Val Asp Thr Leu Gln Phe Val Cys Gly Asp
                805                 810                 815

Arg Gly Phe Tyr Phe Ser Arg Pro Ala Ser Arg Val Ser Arg Arg Ser
            820                 825                 830

Arg Gly Ile Val Glu Glu Cys Cys Phe Arg Ser Cys Asp Leu Ala Leu
        835                 840                 845

Leu Glu Thr Tyr Cys Ala Thr Pro Ala Lys Ser Glu
850                 855                 860
```

<210> SEQ ID NO 21
<211> LENGTH: 60

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Leu Cys Gly Gly Glu Leu Val Asp Thr Leu Gln Phe Val Cys Gly Asp
1               5                   10                  15

Arg Gly Phe Tyr Phe Ser Arg Pro Ala Ser Arg Val Ser Arg Arg Ser
            20                  25                  30

Arg Gly Ile Val Glu Glu Cys Cys Phe Arg Ser Cys Asp Leu Ala Leu
        35                  40                  45

Leu Glu Thr Tyr Cys Ala Thr Pro Ala Lys Ser Glu
    50                  55                  60

<210> SEQ ID NO 22
<211> LENGTH: 821
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65              70                  75                  80

Ser Gly Ser Gln Leu Arg Leu Pro Arg Pro Leu Pro Ala Val Pro Gly
            85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
            115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145             150                 155                 160

Leu Thr Gln Ala Glu Ile Asn Glu Phe Phe Thr Gly Pro Ala Phe Leu
            165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp
        195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225             230                 235                 240

Lys Met Gly Ser Trp Gly His Phe Asn Cys Ser Tyr Ser Cys Ser Phe
```

```
                    245                 250                 255
Leu Leu Ala Pro Glu Asp Pro Ile Phe Pro Ile Ile Gly Ser Leu Phe
                260                 265                 270
Leu Arg Glu Leu Ile Lys Glu Phe Gly Thr Asp His Ile Tyr Gly Ala
                275                 280                 285
Asp Thr Phe Asn Glu Met Gln Pro Pro Ser Ser Glu Pro Ser Tyr Leu
            290                 295                 300
Ala Ala Ala Thr Thr Ala Val Tyr Glu Ala Met Thr Ala Val Asp Thr
305                 310                 315                 320
Glu Ala Val Trp Leu Leu Gln Gly Trp Leu Phe Gln His Gln Pro Gln
                325                 330                 335
Phe Trp Gly Pro Ala Gln Ile Arg Ala Val Leu Gly Ala Val Pro Arg
                340                 345                 350
Gly Arg Leu Leu Val Leu Asp Leu Phe Ala Glu Ser Gln Pro Val Tyr
                355                 360                 365
Thr Arg Thr Ala Ser Phe Gln Gly Gln Pro Phe Ile Trp Cys Met Leu
            370                 375                 380
His Asn Phe Gly Gly Asn His Gly Leu Phe Gly Ala Leu Glu Ala Val
385                 390                 395                 400
Asn Gly Gly Pro Glu Ala Ala Arg Leu Phe Pro Asn Ser Thr Met Val
                405                 410                 415
Gly Thr Gly Met Ala Pro Glu Gly Ile Ser Gln Asn Glu Val Val Tyr
                420                 425                 430
Ser Leu Met Ala Glu Leu Gly Trp Arg Lys Asp Pro Val Pro Asp Leu
                435                 440                 445
Ala Ala Trp Val Thr Ser Phe Ala Ala Arg Arg Tyr Gly Val Ser His
                450                 455                 460
Pro Asp Ala Gly Ala Ala Trp Arg Leu Leu Leu Arg Ser Val Tyr Asn
465                 470                 475                 480
Cys Ser Gly Glu Ala Cys Arg Gly His Asn Arg Ser Pro Leu Val Arg
                485                 490                 495
Arg Pro Ser Leu Gln Met Asn Thr Ser Ile Trp Tyr Asn Arg Ser Asp
                500                 505                 510
Val Phe Glu Ala Trp Arg Leu Leu Leu Thr Ser Ala Pro Ser Leu Ala
                515                 520                 525
Thr Ser Pro Ala Phe Arg Tyr Asp Leu Leu Asp Leu Thr Arg Gln Ala
                530                 535                 540
Val Gln Glu Leu Val Ser Leu Tyr Tyr Glu Glu Ala Arg Ser Ala Tyr
545                 550                 555                 560
Leu Ser Lys Glu Leu Ala Ser Leu Leu Arg Ala Gly Gly Val Leu Ala
                565                 570                 575
Tyr Glu Leu Leu Pro Ala Leu Asp Glu Val Leu Ala Ser Asp Ser Arg
                580                 585                 590
Phe Leu Leu Gly Ser Trp Leu Glu Gln Ala Arg Ala Ala Ala Val Ser
                595                 600                 605
Glu Ala Glu Ala Asp Phe Tyr Glu Gln Asn Ser Arg Tyr Gln Leu Thr
                610                 615                 620
Leu Trp Gly Pro Glu Gly Asn Ile Leu Asp Tyr Ala Asn Lys Gln Leu
625                 630                 635                 640
Ala Gly Leu Val Ala Asn Tyr Tyr Thr Pro Arg Trp Arg Leu Phe Leu
                645                 650                 655
Glu Ala Leu Val Asp Ser Val Ala Gln Gly Ile Pro Phe Gln Gln His
                660                 665                 670
```

```
Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
        690                 695                 700

Lys Lys Ile Phe Leu Lys Tyr Tyr Pro Arg Trp Val Ala Gly Ser Trp
705                 710                 715                 720

Gly Ala Pro Gly Gly Gly Gly Ala Ala Ala Ala Gly Gly Gly
            725                 730                 735

Gly Gly Gly Ala Pro Gly Gly Gly Gly Ala Ala Ala Ala Ala Gly
            740                 745                 750

Gly Gly Gly Gly Ala Pro Gly Gly Gly Gly Ala Ala Ala Ala
            755                 760                 765

Ala Gly Gly Gly Gly Gly Ala Pro Gln Asp Arg Leu Asp Ala Pro
            770                 775                 780

Pro Pro Pro Ala Ala Pro Leu Pro Arg Trp Ser Gly Pro Ile Gly Val
785                 790                 795                 800

Ser Trp Gly Leu Arg Ala Ala Ala Gly Gly Ala Phe Pro Arg Gly
                    805                 810                 815

Gly Arg Trp Arg Arg
            820

<210> SEQ ID NO 23
<211> LENGTH: 801
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Tyr Gln Asn Val
            100                 105                 110

Cys Thr Gln Ser Tyr Ser Phe Val Trp Trp Asp Trp Ala Arg Trp Glu
        115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190
```

```
Pro Ser Trp His Ile Lys Gln Leu Tyr Leu Gln His Arg Val Leu Asp
            195                 200                 205
Gln Met Arg Ser Phe Gly Met Thr Pro Val Leu Pro Ala Phe Ala Gly
    210                 215                 220
His Val Pro Glu Ala Val Thr Arg Val Phe Pro Gln Val Asn Val Thr
225                 230                 235                 240
Lys Met Gly Ser Trp Gly His Phe Asn Cys Ser Tyr Ser Cys Ser Phe
                245                 250                 255
Leu Leu Ala Pro Glu Asp Pro Ile Phe Pro Ile Ile Gly Ser Leu Phe
            260                 265                 270
Leu Arg Glu Leu Ile Lys Glu Phe Gly Thr Asp His Ile Tyr Gly Ala
        275                 280                 285
Asp Thr Phe Asn Glu Met Gln Pro Pro Ser Ser Glu Pro Ser Tyr Leu
    290                 295                 300
Ala Ala Ala Thr Thr Ala Val Tyr Glu Ala Met Thr Ala Val Asp Thr
305                 310                 315                 320
Glu Ala Val Trp Leu Leu Gln Gly Trp Leu Phe Gln His Gln Pro Gln
                325                 330                 335
Phe Trp Gly Pro Ala Gln Ile Arg Ala Val Leu Gly Ala Val Pro Arg
            340                 345                 350
Gly Arg Leu Leu Val Leu Asp Leu Phe Ala Glu Ser Gln Pro Val Tyr
        355                 360                 365
Thr Arg Thr Ala Ser Phe Gln Gly Gln Pro Phe Ile Trp Cys Met Leu
    370                 375                 380
His Asn Phe Gly Gly Asn His Gly Leu Phe Gly Ala Leu Glu Ala Val
385                 390                 395                 400
Asn Gly Gly Pro Glu Ala Ala Arg Leu Phe Pro Asn Ser Thr Met Val
                405                 410                 415
Gly Thr Gly Met Ala Pro Glu Gly Ile Ser Gln Asn Glu Val Val Tyr
            420                 425                 430
Ser Leu Met Ala Glu Leu Gly Trp Arg Lys Asp Pro Val Pro Asp Leu
        435                 440                 445
Ala Ala Trp Val Thr Ser Phe Ala Ala Arg Arg Tyr Gly Val Ser His
    450                 455                 460
Pro Asp Ala Gly Ala Ala Trp Arg Leu Leu Leu Arg Ser Val Tyr Asn
465                 470                 475                 480
Cys Ser Gly Glu Ala Cys Arg Gly His Asn Arg Ser Pro Leu Val Arg
                485                 490                 495
Arg Pro Ser Leu Gln Met Asn Thr Ser Ile Trp Tyr Asn Arg Ser Asp
            500                 505                 510
Val Phe Glu Ala Trp Arg Leu Leu Leu Thr Ser Ala Pro Ser Leu Ala
        515                 520                 525
Thr Ser Pro Ala Phe Arg Tyr Asp Leu Leu Asp Leu Thr Arg Gln Ala
    530                 535                 540
Val Gln Glu Leu Val Ser Leu Tyr Tyr Glu Ala Arg Ser Ala Tyr
545                 550                 555                 560
Leu Ser Lys Glu Leu Ala Ser Leu Leu Arg Ala Gly Gly Val Leu Ala
                565                 570                 575
Tyr Glu Leu Leu Pro Ala Leu Asp Glu Val Leu Ala Ser Asp Ser Arg
            580                 585                 590
Phe Leu Leu Gly Ser Trp Leu Glu Gln Ala Arg Ala Ala Ala Val Ser
        595                 600                 605
Glu Ala Glu Ala Asp Phe Tyr Glu Gln Asn Ser Arg Tyr Gln Leu Thr
```

```
              610                 615                 620
Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
                660                 665                 670

Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
690                 695                 700

Lys Lys Ile Phe Leu Lys Tyr Tyr Pro Arg Trp Val Ala Gly Ser Trp
705                 710                 715                 720

Gly Ala Pro Gly Gly Gly Gly Ala Ala Ala Ala Gly Gly Gly
                725                 730                 735

Gly Gly Gly Ala Pro Gly Gly Gly Gly Ala Ala Ala Ala Gly
            740                 745                 750

Gly Gly Gly Gly Ala Pro Gly Gly Gly Gly Ala Ala Ala Ala
        755                 760                 765

Ala Gly Gly Gly Gly Gly Ala Pro Thr Lys Cys Leu Arg Arg Glu
770                 775                 780

Ala Pro Arg Trp Asp Ala Pro Leu Arg Asp Pro Ala Leu Arg Gln Leu
785                 790                 795                 800

Leu
```

<210> SEQ ID NO 24
<211> LENGTH: 897
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
                20                  25                  30

Leu Ala Ala Lys Pro Gly Leu Asp Thr Tyr Ser Leu Gly Gly Gly Gly
            35                  40                  45

Ala Ala Arg Val Arg Val Arg Gly Ser Thr Gly Val Ala Ala Ala Ala
50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
                100                 105                 110

Cys Thr Gln Ser Tyr Ser Phe Val Trp Trp Asp Trp Ala Arg Trp Glu
            115                 120                 125

Arg Glu Ile Asp Trp Met Ala Leu Asn Gly Ile Asn Leu Ala Leu Ala
        130                 135                 140

Trp Ser Gly Gln Glu Ala Ile Trp Gln Arg Val Tyr Leu Ala Leu Gly
145                 150                 155                 160
```

```
Leu Thr Gln Ala Glu Ile Asn Glu Phe Phe Thr Gly Pro Ala Phe Leu
                165                 170                 175
Ala Trp Gly Arg Met Gly Asn Leu His Thr Trp Asp Gly Pro Leu Pro
            180                 185                 190
Pro Ser Trp His Ile Lys Gln Leu Tyr Leu Gln His Arg Val Leu Asp
        195                 200                 205
Gln Met Arg Ser Phe Gly Met Thr Pro Val Leu Pro Ala Phe Ala Gly
    210                 215                 220
His Val Pro Glu Ala Val Thr Arg Val Phe Pro Gln Val Asn Val Thr
225                 230                 235                 240
Lys Met Gly Ser Trp Gly His Phe Asn Cys Ser Tyr Ser Cys Ser Phe
                245                 250                 255
Leu Leu Ala Pro Glu Asp Pro Ile Phe Pro Ile Ile Gly Ser Leu Phe
            260                 265                 270
Leu Arg Glu Leu Ile Lys Glu Phe Gly Thr Asp His Ile Tyr Gly Ala
        275                 280                 285
Asp Thr Phe Asn Glu Met Gln Pro Pro Ser Ser Glu Pro Ser Tyr Leu
    290                 295                 300
Ala Ala Ala Thr Thr Ala Val Tyr Glu Ala Met Thr Ala Val Asp Thr
305                 310                 315                 320
Glu Ala Val Trp Leu Leu Gln Gly Trp Leu Phe Gln His Gln Pro Gln
                325                 330                 335
Phe Trp Gly Pro Ala Gln Ile Arg Ala Val Leu Gly Ala Val Pro Arg
            340                 345                 350
Gly Arg Leu Leu Val Leu Asp Leu Phe Ala Glu Ser Gln Pro Val Tyr
        355                 360                 365
Thr Arg Thr Ala Ser Phe Gln Gly Gln Pro Phe Ile Trp Cys Met Leu
    370                 375                 380
His Asn Phe Gly Gly Asn His Gly Leu Phe Gly Ala Leu Glu Ala Val
385                 390                 395                 400
Asn Gly Gly Pro Glu Ala Ala Arg Leu Phe Pro Asn Ser Thr Met Val
                405                 410                 415
Gly Thr Gly Met Ala Pro Glu Gly Ile Ser Gln Asn Glu Val Val Tyr
            420                 425                 430
Ser Leu Met Ala Glu Leu Gly Trp Arg Lys Asp Pro Val Pro Asp Leu
        435                 440                 445
Ala Ala Trp Val Thr Ser Phe Ala Ala Arg Arg Tyr Gly Val Ser His
    450                 455                 460
Pro Asp Ala Gly Ala Ala Trp Arg Leu Leu Arg Ser Val Tyr Asn
465                 470                 475                 480
Cys Ser Gly Glu Ala Cys Arg Gly His Asn Arg Ser Pro Leu Val Arg
                485                 490                 495
Arg Pro Ser Leu Gln Met Asn Thr Ser Ile Trp Tyr Asn Arg Ser Asp
            500                 505                 510
Val Phe Glu Ala Trp Arg Leu Leu Leu Thr Ser Ala Pro Ser Leu Ala
        515                 520                 525
Thr Ser Pro Ala Phe Arg Tyr Asp Leu Leu Asp Leu Thr Arg Gln Ala
    530                 535                 540
Val Gln Glu Leu Val Ser Leu Tyr Tyr Glu Ala Arg Ser Ala Tyr
545                 550                 555                 560
Leu Ser Lys Glu Leu Ala Ser Leu Leu Arg Ala Gly Gly Val Leu Ala
                565                 570                 575
Tyr Glu Leu Leu Pro Ala Leu Asp Glu Val Leu Ala Ser Asp Ser Arg
```

```
            580                 585                 590
Phe Leu Leu Gly Ser Trp Leu Glu Gln Ala Arg Ala Ala Val Ser
                595                 600                 605
Glu Ala Glu Ala Asp Phe Tyr Glu Gln Asn Ser Arg Tyr Gln Leu Thr
            610                 615                 620
Leu Trp Gly Pro Glu Gly Asn Ile Leu Asp Tyr Ala Asn Lys Gln Leu
625                 630                 635                 640
Ala Gly Leu Val Ala Asn Tyr Tyr Thr Pro Arg Trp Arg Leu Phe Leu
                645                 650                 655
Glu Ala Leu Val Asp Ser Val Ala Gln Gly Ile Pro Phe Gln Gln His
            660                 665                 670
Gln Phe Asp Lys Asn Val Phe Gln Leu Glu Gln Ala Phe Val Leu Ser
            675                 680                 685
Lys Gln Arg Tyr Pro Ser Gln Pro Arg Gly Asp Thr Val Asp Leu Ala
            690                 695                 700
Lys Lys Ile Phe Leu Lys Tyr Tyr Pro Arg Trp Val Ala Gly Ser Trp
705                 710                 715                 720
Gly Ala Pro Gly Gly Gly Gly Ala Ala Ala Ala Gly Gly
                725                 730                 735
Gly Gly Gly Ala Pro Gly Gly Gly Gly Ala Ala Ala Ala Gly
            740                 745                 750
Gly Gly Gly Gly Ala Pro Gly Gly Gly Gly Ala Ala Ala
            755                 760                 765
Ala Gly Gly Gly Gly Ala Pro Asp Gly Gly Phe Cys Glu Val
770                 775                 780
Cys Lys Lys Leu Val Gly Tyr Leu Asp Arg Asn Leu Glu Lys Asn Ser
785                 790                 795                 800
Thr Lys Gln Glu Ile Leu Ala Ala Leu Glu Lys Gly Cys Ser Phe Leu
                805                 810                 815
Pro Asp Pro Tyr Gln Lys Gln Cys Asp Gln Phe Val Ala Glu Tyr Glu
            820                 825                 830
Pro Val Leu Ile Glu Ile Leu Val Glu Val Met Asp Pro Ser Phe Val
            835                 840                 845
Cys Leu Lys Ile Gly Ala Cys Pro Ser Ala His Lys Pro Leu Leu Gly
            850                 855                 860
Thr Glu Lys Cys Ile Trp Gly Pro Ser Tyr Trp Cys Gln Asn Thr Glu
865                 870                 875                 880
Thr Ala Ala Gln Cys Asn Ala Val Glu His Cys Lys Arg His Val Trp
                885                 890                 895
Asn

<210> SEQ ID NO 25
<211> LENGTH: 837
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Glu Ala Arg Glu Ala Ala Val Arg Ala Leu Val Ala Arg Leu
1               5                   10                  15
Leu Gly Pro Gly Pro Ala Ala Asp Phe Ser Val Ser Val Glu Arg Ala
                20                  25                  30
```

```
Leu Ala Ala Lys Pro Gly Leu Asp Thr Tyr Ser Leu Gly Gly Gly
            35                  40                  45

Ala Ala Arg Val Arg Val Arg Gly Ser Thr Gly Val Ala Ala Ala
 50                  55                  60

Gly Leu His Arg Tyr Leu Arg Asp Phe Cys Gly Cys His Val Ala Trp
 65                  70                  75                  80

Ser Gly Ser Gln Leu Arg Leu Pro Arg Pro Leu Pro Ala Val Pro Gly
                 85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
            115                 120                 125

Arg Glu Ile Asp Trp Met Ala Leu Asn Gly Ile Asn Leu Ala Leu Ala
            130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp
            195                 200                 205

Gln Met Arg Ser Phe Gly Met Thr Pro Val Leu Pro Ala Phe Ala Gly
            210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
            260                 265                 270

Leu Arg Glu Leu Ile Lys Glu Phe Gly Thr Asp His Ile Tyr Gly Ala
            275                 280                 285

Asp Thr Phe Asn Glu Met Gln Pro Pro Ser Ser Glu Pro Ser Tyr Leu
            290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
            340                 345                 350

Gly Arg Leu Leu Val Leu Asp Leu Phe Ala Glu Ser Gln Pro Val Tyr
            355                 360                 365

Thr Arg Thr Ala Ser Phe Gln Gly Gln Pro Phe Ile Trp Cys Met Leu
            370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
            420                 425                 430

Ser Leu Met Ala Glu Leu Gly Trp Arg Lys Asp Pro Val Pro Asp Leu
            435                 440                 445

Ala Ala Trp Val Thr Ser Phe Ala Ala Arg Arg Tyr Gly Val Ser His
```

```
            450                 455                 460
Pro Asp Ala Gly Ala Ala Trp Arg Leu Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
            500                 505                 510

Val Phe Glu Ala Trp Arg Leu Leu Thr Ser Ala Pro Ser Leu Ala
        515                 520                 525

Thr Ser Pro Ala Phe Arg Tyr Asp Leu Leu Asp Leu Thr Arg Gln Ala
    530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Val Ser
        595                 600                 605

Glu Ala Glu Ala Asp Phe Tyr Glu Gln Asn Ser Arg Tyr Gln Leu Thr
    610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
        675                 680                 685

Lys Gln Arg Tyr Pro Ser Gln Pro Arg Gly Asp Thr Val Asp Leu Ala
    690                 695                 700

Lys Lys Ile Phe Leu Lys Tyr Tyr Pro Arg Trp Val Ala Gly Ser Trp
705                 710                 715                 720

Gly Ala Pro Gly Gly Gly Gly Ala Ala Ala Ala Gly Gly
                725                 730                 735

Gly Gly Gly Ala Pro Gly Gly Gly Gly Ala Ala Ala Ala Gly
            740                 745                 750

Gly Gly Gly Gly Ala Pro Gly Gly Gly Gly Ala Ala Ala
        755                 760                 765

Ala Gly Gly Gly Gly Gly Ala Pro Leu Cys Gly Gly Glu Leu Val
770                 775                 780

Asp Thr Leu Gln Phe Val Cys Gly Asp Arg Gly Phe Tyr Phe Ser Arg
785                 790                 795                 800

Pro Ala Ser Arg Val Ser Arg Arg Ser Arg Gly Ile Val Glu Glu Cys
                805                 810                 815

Cys Phe Arg Ser Cys Asp Leu Ala Leu Leu Glu Thr Tyr Cys Ala Thr
            820                 825                 830

Pro Ala Lys Ser Glu
        835

<210> SEQ ID NO 26
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic 6xHis tag"

<400> SEQUENCE: 26

His His His His His His
1               5
```

LYSOSOMAL TARGETING AND USES THEREOF

CROSS-REFERENCE TO RELATED APPLICATIONS

This application is a 35 U.S.C. § 371 National Stage Application of International Application No. PCT/US2015/044718, filed Aug. 11, 2015, which claims priority to U.S. Provisional Application 62/036,084 filed on Aug. 11, 2014, the disclosure of which is hereby incorporated by reference in its entirety.

BACKGROUND

More than forty lysosomal storage diseases are caused, directly or indirectly, by the absence or deficiency of one or more lysosomal enzymes. Sanfilippo syndrome, or mucopolysaccharidosis III (MPS III), is one such disease. It is a rare genetic disorder characterized by the deficiency of enzymes involved in the degradation of glycosaminoglycans (GAG).

Four distinct forms of MPS III, designated MPS IIIA, B, C, and D, have been identified. Each is characterized by the absence or deficiency of a different lysosomal enzyme. Mucopolysaccharidosis type IIIB (MPS IIIB; Sanfilippo B disease) is an autosomal recessive disorder that is caused by a deficiency of the enzyme alpha-N-acetyl-glucosaminidase (Naglu), resulting in the accumulation of heparan sulfate in lysosomes of particularly neurons and glial cells in the brain, with additional lysosomal accumulation of heparan sulfate elsewhere. MPS IIIB manifests itself primarily in the brain.

Enzyme replacement therapy (ERT) has been used to deliver enzymes for the treatment of various lysosomal storage diseases. Normally, lysosomal enzymes are synthesized in the cytosol and then traverse the endoplasmic reticulum (ER), where they are glycosylated with N-linked, high mannose type carbohydrates. In the Golgi apparatus, high mannose carbohydrates on glycoproteins are then modified by a series of glycotransferases to become mature N-glycan; one of the modifications is the addition of mannose-6-phosphate (M6P). Proteins carrying this modification are then targeted to the lysosome via binding of the M6P moiety to the cation-independent mannose-6-phosphate receptor (CI-MPR). Efficacy of enzyme replacement therapy is critically dependent on proper lysosomal targeting of the replacement enzyme. However, recombinantly produced Naglu protein is characterized by a dramatic lack of M6P phosphorylation, making lysosomal targeting of this enzyme and its effective use for ERT very difficult.

Therefore, there remains a need to develop alternative methods for lysosomal targeting to ensure effective enzyme replacement therapy.

SUMMARY

The present invention provides an alternative, but more efficient, reliable and consistent lysosomal targeting approach for enzyme replacement therapy. The present invention is, in part, based on the surprising discovery that replacement enzymes can be effectively delivered to lysosomes via a receptor other than the cation-independent mannose-6-phosphate receptor, i.e., the sortilin-1 receptor (SORT1). Since binding to SORT1 is not based on glycosylation and/or M6P phosphorylation, the present invention can be used for lysosomal delivery of enzymes with low levels, or even complete absence, of glycosylation and/or M6P phosphorylation. Accordingly, the present invention allows to simplify the manufacturing process for enzymes used for enzyme replacement therapy since steps geared to ensure proper glycosylation can be omitted, for example. Since SORT1 is known to be enriched in the CNS (Petersen et al., 1997 J. Biol. Chem. 272:3599-3605), SORT1-based lysosomal targeting is particularly useful in treating lysosomal storage diseases that have CNS manifestations.

Thus, in one aspect, the present invention provides a targeted therapeutic comprising a lysosomal enzyme and a lysosomal targeting moiety that binds to SORT1. In some embodiments, a lysosomal enzyme suitable for the present invention is selected from Table 2. In some embodiments, a suitable lysosomal enzyme is an N-Acetylglucosaminidase (Naglu) protein.

In some embodiments, the Naglu protein comprises an amino acid sequence at least about 70% (e.g., at least about 75%, 80%, 85%, 90%, or 95%) identical to SEQ ID NO:1. In some embodiments, the Naglu protein comprises an amino acid sequence at least 80% identical to SEQ ID NO:1. In some embodiments, the Naglu protein comprises an amino acid sequence at least 90% identical to SEQ ID NO:1. In some embodiments, the Naglu protein comprises an amino acid sequence at least 95% identical to SEQ ID NO:1. In some embodiments, the Naglu protein comprises an amino acid sequence identical to SEQ ID NO:1.

In some embodiments, a suitable lysosomal targeting moiety according to the invention is a peptide. In some embodiments, a suitable peptide is a SORT1 peptide, a progranulin peptide or a prosaposin peptide, or a fragment thereof.

In some embodiments, a suitable peptide contains a sequence at least about 70% (e.g., at least about 75%, 80%, 85%, 90%, or 95%) identical to SEQ ID NO. 3, 4, 5, 6, 7 or 8. In some embodiments, a suitable peptide contains a sequence at least 80% identical to SEQ ID NO. 3, 4, 5, 6, 7 or 8. In some embodiments, a suitable peptide contains a sequence at least 90% identical to SEQ ID NO. 3, 4, 5, 6, 7 or 8. In some embodiments, a suitable peptide contains a sequence at least 95% identical to SEQ ID NO. 3, 4, 5, 6, 7 or 8. In some embodiments, a suitable peptide contains a sequence identical to SEQ ID NO. 3, 4, 5, 6, 7 or 8.

In some embodiments, a suitable peptide is a SORT1 propeptide (SPP). In some embodiments, a suitable peptide comprises a sequence at least 80%, 90%, or 95% identical to SEQ ID NO:4. In some embodiments, a suitable peptide comprises an amino acid sequence identical to SEQ ID NO:4.

In some embodiments, a targeted therapeutic according to the present invention is a fusion protein. In some embodiments, the lysosomal targeting moiety is fused to the N-terminus of the lysosomal enzyme. In some embodiments, the lysosomal targeting moiety is fused to the C-terminus of the lysosomal enzyme.

In some embodiments, the lysosomal targeting moiety and the lysosomal enzyme are fused via a linker. In some embodiments, a suitable linker contains a sequence of

```
                                          (SEQ ID NO: 13)
GAPGGGGAAAAAGGGGGAPGGGGGAAAAAGGGGGAPGGGGGAAAAAG
GGGGAP.
```

In some embodiments, the fusion protein contains a sequence at least about 70% (e.g., at least about 75%, 80%, 85%, 90%, or 95%) identical to the amino acid sequence of SEQ ID NO. 17, 18 or 19. In some embodiments, the fusion protein contains a sequence at least 90% identical to the amino acid sequence of SEQ ID NO. 17, 18 or 19. In some embodiments, the fusion protein contains a sequence at least 95% identical to the amino acid sequence of SEQ ID NO. 17, 18 or 19. In some embodiments, the fusion protein comprises a sequence identical to the amino acid sequence of SEQ ID NO. 17, 18 or 19.

In some embodiments, the fusion protein contains a sequence at least about 70% (e.g., at least about 75%, 80%, 85%, 90%, or 95%) identical to the amino acid sequence of SEQ ID NO. 22, 23 or 24. In some embodiments, the fusion protein contains a sequence at least 90% identical to the amino acid sequence of SEQ ID NO. 22, 23 or 24. In some embodiments, the fusion protein contains a sequence at least 95% identical to the amino acid sequence of SEQ ID NO. 22, 23 or 24. In some embodiments, the fusion protein comprises a sequence identical to the amino acid sequence of SEQ ID NO. 22, 23 or 24.

Among other things, the present invention provides a nucleic acid encoding a fusion protein described herein. In some embodiments, the present invention provides a vector containing a nucleic acid sequence described herein. In some embodiments, the present invention provides a host cell containing a vector described herein. In some embodiments, a suitable host cell is selected from a bacterial, yeast, insect or mammalian cell. In some embodiments, a suitable host cell is a mammalian cell. In some embodiments, a suitable mammalian cell is a human cell. In some embodiments, a suitable mammalian cell is a CHO cell line.

In another aspect, the present invention provides a method of producing a fusion protein described herein. In some embodiments, a method according to the present invention includes the steps of a) culturing a host cell containing a nucleic acid encoding a fusion protein described herein under conditions suitable for expression of the fusion protein by the host cell; and b) harvesting the fusion protein expressed by the host cell.

In still another aspect, the present invention provides a pharmaceutical composition containing a targeted therapeutic described herein, and a pharmaceutical acceptable carrier.

In yet another aspect, the present invention provides a method of treating a lysosomal storage disease by administering to a subject in need of treatment a pharmaceutical composition described herein. In some embodiments, the present invention may be used to treat Sanfilippo syndrome type B. In some embodiments, the pharmaceutical composition is administered intravenously, subcutaneously, intrathecally and/or combinations thereof.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE FIGURES

FIGS. 8C-H show high magnification micrographs of immunohistochemical staining of Naglu protein in wild-type rat cerebral cortex tissue at 24 hours post intrathecal delivery of (C) vehicle control, (D) rhNaglu, (E) Naglu-SapDC (F) Naglu-tPRGN (G) Naglu-IGFII or (H) Naglu-SPP.

DEFINITIONS

Figure 1:
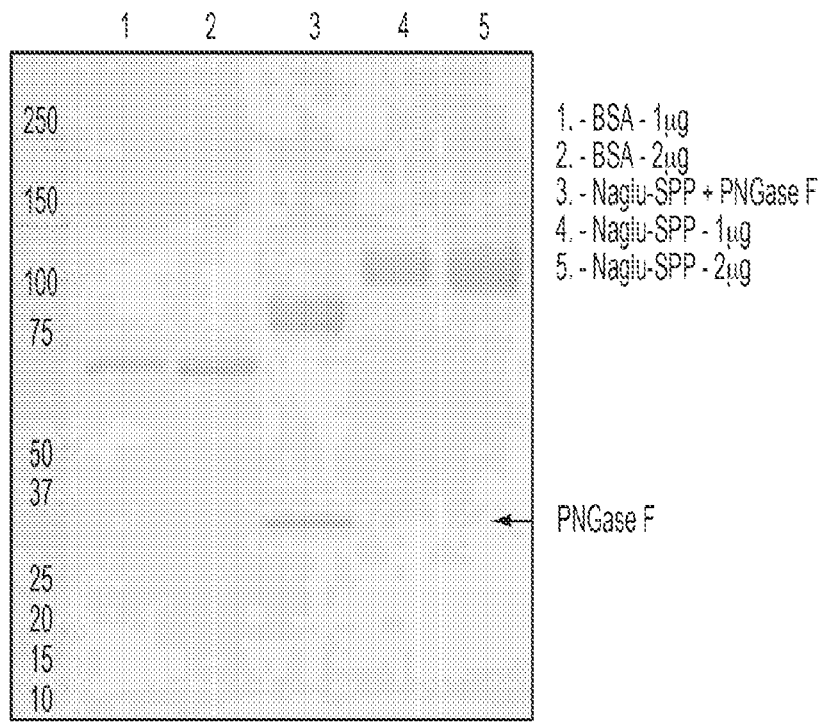
FIG. 1 shows SDS-PAGE analysis of purified Naglu-SPP before and after deglycosylation by PNGaseF.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor", "CI-MPR/IGF-II receptor", "CD222", "MPR300", "IGF-II receptor" or "IGF2 Receptor." These terms and abbreviations thereof are used interchangeably herein.

Cell culture: These terms as used herein refer to a cell population that is gown in a medium under conditions suitable to survival and/or growth of the cell population. As will be clear to those of ordinary skill in the art, these terms as used herein may refer to the combination comprising the cell population and the medium in which the population is grown.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalent, are used inter-changeably.

Fragment: The term "fragment" as used herein refers to polypeptides and is defined as any discrete portion of a given polypeptide that is unique to or characteristic of that polypeptide. The term as used herein also refers to any discrete portion of a given polypeptide that retains at least a fraction of the activity of the full-length polypeptide. Preferably the fraction of activity retained is at least 10% of the activity of the full-length polypeptide. More preferably the fraction of activity retained is at least 20%, 30%, 40%, 50%, 60%, 70%, 80% or 90% of the activity of the full-length polypeptide. More preferably still the fraction of activity retained is at least 95%, 96%, 97%, 98% or 99% of the activity of the full-length polypeptide. Most preferably, the fraction of activity retained is 100% of the activity of the full-length polypeptide. The term as used herein also refers to any portion of a given polypeptide that includes at least an established sequence element found in the full-length polypeptide. Preferably, the sequence element spans at least 4-5, more preferably at least about 10, 15, 20, 25, 30, 35, 40, 45, 50 or more amino acids of the full-length polypeptide.

Gene: The term "gene" as used herein refers to any nucleotide sequence, DNA or RNA, at least some portion of which encodes a discrete final product, typically, but not limited to, a polypeptide, which functions in some aspect of a cellular process. The term is not meant to refer only to the coding sequence that encodes the polypeptide or other discrete final product, but may also encompass regions preceding and following the coding sequence that modulate the basal level of expression, as well as intervening sequences ("introns") between individual coding segments ("exons"). In some embodiments, a gene may include regulatory sequences (e.g., promoters, enhancers, poly adenylation sequences, termination sequences, Kozac sequences, tata box, etc.) and/or modification sequences. In some embodiments, a gene may include references to nucleic acids that do not encode proteins but rather encode functional RNA molecules such as tRNAs, RNAi-inducing agents, etc.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Genetic control element: The term "genetic control element" as used herein refers to any sequence element that modulates the expression of a gene to which it is operably linked. Genetic control elements may function by either increasing or decreasing the expression levels and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 2.

Lysosomal enzyme deficiency: As used herein, "lysosomal enzyme deficiency" refers to a group of genetic disorders that result from deficiency in at least one of the enzymes that are required to break macromolecules (e.g., enzyme substrates) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Peptide: As used herein, a "peptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that peptides sometimes include "non-natural" amino acids or other entities that nonetheless are capable of integrating into a polypeptide chain, optionally. As used herein, the terms "polypeptide" and "peptide" are used inter-changeably.

Protein: As used herein, the term "protein" of "therapeutic protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient."

A subject can be afflicted with or is susceptible to a disease or disorder but may or may not display symptoms of the disease or disorder.

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

DETAILED DESCRIPTION

The present invention provides, among other things, methods and compositions for lysosomal targeting of a therapeutic protein (e.g., a lysosomal enzyme) based on a lysosomal targeting moiety that binds to SORT1. In some embodiments, the present invention provides a targeted therapeutic comprising a lysosomal enzyme and a lysosomal targeting moiety that binds to SORT1.

Various aspects of the invention are described in further detail in the following subsections. The use of subsections is not meant to limit the invention. Each subsection may apply to any aspect of the invention. In this application, the use of "or" means "and/or" unless stated otherwise.

Lysosomal Enzymes

The present invention may be used to target any therapeutic protein to a lysosome. In particular, the present invention may be used to target a lysosomal enzyme to a lysosome for the treatment of a lysosomal storage disease. According to the present invention, a lysosomal enzyme is contemplated to encompass any enzyme or protein, when targeted to the lysosome, is suitable for the treatment of a lysosomal storage disease. As a non-limiting example, a particularly suitable lysosomal enzyme is a N-Acetylglucosaminidase (Naglu) protein, which is deficient in Sanfilippo Syndrome Type B disease. Additional exemplary lysosomal enzymes are shown in Table 2.

Naglu Protein

A suitable Naglu protein according to the present invention can be any molecule that can substitute for naturally-occurring Naglu protein activity or rescue one or more phenotypes or symptoms associated with Naglu-deficiency. In some embodiments, a Naglu protein suitable for the invention is a polypeptide having an N-terminus and C-terminus, along with an amino acid sequence substantially similar or identical to mature human Naglu protein.

Typically, human Naglu is produced as a precursor molecule that is processed to a mature form. This process generally occurs by removing the 23 amino acid signal peptide as the protein enters the endoplasmic reticulum. Typically, the precursor form is also referred to as full-length precursor or full-length Naglu protein, which contains 743 amino acids. The N-terminal 23 amino acids are cleaved as the precursor protein enters the endoplasmic reticulum, resulting in a mature form. Thus, it is contemplated that the N-terminal 23 amino acids is generally not required for the Naglu protein activity. However, the use of the full-length precursor of the Naglu protein is also contemplated within the scope of the instant invention. The amino acid sequences of the mature form (SEQ ID NO:1) and full-length precursor (SEQ ID NO:2) of a typical wild-type or naturally-occurring human Naglu protein are shown in Table 1.

TABLE 1

Mature and Precursor Naglu Protein

| | |
|---|---|
| Mature Form of Naglu | DEAREAAAVRALVARLLGPGPAADFSVSVERALAAKPGLDTYSLGGGGAARVRV RGSTGVAAAAGLHRYLRDFCGCHVAWSGSQLRLPRPLPAVPGELTEATPNRYRY YQNVCTQSYSFVWWDWARWEREIDWMALNGINLALAWSGQEAIWQRVYLALGLT QAEINEFFTGPAFLAWGRMGNLHTWDGPLPPSWHIKQLYLQHRVLDQMRSFGMT PVLPAFAGHVPEAVTRVFPQVNVTKMGSWGHFNCSYSCSFLLAPEDPIFPIIGS LFLRELIKEFGTDHIYGADTFNEMQPPSSEPSYLAAATTAVYEAMTAVDTEAVW LLQGWLFQHQPQFWGPAQIRAVLGAVPRGRLLVLDLFAESQPVYTRTASFQGQP FIWCMLHNFGGNHGLFGALEAVNGGPEAARLFPNSTMVGTGMAPEGISQNEVVY SLMAELGWRKDPVPDLAAWVTSFAARRYGVSHPDAGAAWRLLLRSVYNCSGEAC RGHNRSPLVRRPSLQMNTSIWYNRSDVFEAWRLLLTSAPSLATSPAFRYDLLDL TRQAVQELVSLYYEEARSAYLSKELASLLRAGGVLAYELLPALDEVLASDSRFL LGSWLEQARAAAVSEAEADFYEQNSRYQLTLWGPEGNILDYANKQLAGLVANYY TPRWRLFLEALVDSVAQGIPFQQHQFDKNVFQLEQAFVLSKQRYPSQPRGDTVD LAKKIFLKYYPRWVAGSW (SEQ ID NO: 1) |

TABLE 1-continued

Mature and Precursor Naglu Protein

| | |
|---|---|
| Full-Length Precursor/Full-Length Naglu Protein | MEAVAVAAAVGVLLLAGAGGAAGDEAREAAAVRALVARLLGPGPAADFSVSVER ALAAKPGLDTYSLGGGGAARVRVRGSTGVAAAAGLHRYLRDFCGCHVAWSGSQL RLPRPLPAVPGELTEATPNRYRYYQNVCTQSYSFVWWDWARWEREIDWMALNGI NLALAWSGQEAIWQRVYLALGLTQAEINEFFTGPAFLAWGRMGNLHTWDGPLPP SWHIKQLYLQHRVLDQMRSFGMTPVLPAFAGHVPEAVTRVFPQVNVTKMGSWGH FNCSYSCSFLLAPEDPIFPIIGSLFLRELIKEFGTDHIYGADTFNEMQPPSSEP SYLAAATTAVYEAMTAVDTEAVWLLQGWLFQHQPQFWGPAQIRAVLGAVPRGRL LVLDLFAESQPVYTRTASFQGQPFIWCMLHNFGGNHGLFGALEAVNGGPEAARL FPNSTMVGTGMAPEGISQNEVVYSLMAELGWRKDPVPDLAAWVTSFAARRYGVS HPDAGAAWRLLLRSVYNCSGEACRGHNRSPLVRRPSLQMNTSIWYNRSDVFEAW RLLLTSAPSLATSPAFRYDLLDLTRQAVQELVSLYYEEARSAYLSKELASLLRA GGVLAYELLPALDEVLASDSRFLLGSWLEQARAAAVSEAEADFYEQNSRYQLTL WGPEGNILDYANKQLAGLVANYYTPRWRLFLEALVDSVAQGIPFQQHQFDKNVF QLEQAFVLSKQRYPSQPRGDTVDLAKKIFLKYYPRWVAGSW (SEQ ID NO: 2) |

Thus, in some embodiments, Naglu protein suitable for the present invention is a mature human Naglu protein (SEQ ID NO:1). In some embodiments, a suitable Naglu protein may be a homologue or an orthologue of the mature human Naglu protein from a different species (e.g., mouse, rat, sheep, pig, dog, etc.). In other embodiments, a suitable Naglu protein may be a functional variant of the mature human Naglu protein. A functional variant of the mature human Naglu protein may be a modified mature human Naglu protein containing one or more amino acid substitutions, deletions, and/or insertions as compared to a wild-type or naturally-occurring Naglu protein (e.g., SEQ ID NO:1), while retaining substantial Naglu protein activity. Thus, in some embodiments, a Naglu protein suitable for the present invention is substantially homologous to mature human Naglu protein (SEQ ID NO:1). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a Naglu protein suitable for the present invention is substantially identical to mature human Naglu protein (SEQ ID NO:1). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a Naglu protein suitable for the present invention contains a fragment or a portion of mature human Naglu protein.

Alternatively, a Naglu protein suitable for the present invention is a full-length Naglu protein. In some embodiments, a Naglu protein suitable may be a homologue or an orthologue of the full-length human Naglu protein from a different species (e.g., mouse, rat, sheep, pig, dog, etc.). In some embodiments, a suitable Naglu protein is a functional variant of the full-length human Naglu protein, containing one or more amino acid substitutions, deletions, and/or insertions as compared to a wild-type or naturally-occurring full-length Naglu protein (e.g., SEQ ID NO:2), while retaining substantial Naglu protein activity. Thus, in some embodiments, Naglu protein suitable for the present invention is substantially homologous to full-length human Naglu protein (SEQ ID NO:2). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a Naglu protein suitable for the present invention is substantially identical to SEQ ID NO:2. In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a Naglu protein suitable for the present invention contains a fragment or a portion of full-length human Naglu protein. As used herein, a full-length Naglu protein typically contains a signal peptide sequence.

Additional Lysosomal Enzymes

The present invention may be used to deliver any lysosomal enzymes that can be used to treat any lysosomal storage diseases, in particular those lysosomal storage diseases having CNS etiology and/or symptoms, including, but are not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucher disease and sialic acid storage disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in Table 2 below:

TABLE 2

Enzymes Associated With Lysosomal Storage Disease

| Disease Name | Enzyme Deficiency | Substance Stored |
|---|---|---|
| Pompe Disease | Acid-a1, 4-Glucosidase | Glycogen α-1-4 linked Oligosaccharides |
| GM1 Gangliodsidosis | β-Galactosidase | GM$_1$ Gangliosides |
| Tay-Sachs Disease | β-Hexosaminidase A | GM$_2$ Ganglioside |
| GM2 Gangliosidosis: AB Variant | GM$_2$ Activator Protein | GM$_2$ Ganglioside |
| Sandhoff Disease | β-Hexosaminidase A&B | GM$_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl/Oligosaccharides |
| Aspartylglucos-aminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

In some embodiments, a suitable lysosomal enzyme may be a naturally occurring lysosomal enzyme. In some embodiments, a suitable lysosomal enzyme may be a recombinant version of a naturally occurring lysosomal enzyme.

In some embodiments, a lysosomal enzyme suitable for the invention may have a wild-type or naturally occurring sequence. In some embodiments, a lysosomal enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

Lysosomal Targeting Moiety

According to the present invention, a lysosomal targeting moiety refers to any moiety that can facilitate lysosomal delivery via binding to SORT1, directly or indirectly.

SORT1 is a 95 kDa type 1 transmembrane receptor protein in the Golgi apparatus which mediates the trafficking of proteins and ligands from the Golgi apparatus to endosomes and vice versa. SORT1 is the largest protein in the Vps10 family. The N-terminal, luminal part of SORT1 consists of multiple domains that bind to a series of ligands such as Neurotensin, Prosaposin, Progranulin, Lipoprotein Lipase, etc. The relatively small C-terminal, cytosolic part of SORT1 contains a Golgi trafficking signal.

SORT1 is synthesized as Prosortilin (SEQ ID NO.: 3). The N-terminal part of Prosortilin is then cleaved in the Golgi apparatus, resulting in mature SORT1. The N-terminal cleavage of Prosortilin occurs in two steps. First, the N-terminal 33 amino acids of Prosortilin are cleaved. This is followed by N-terminal cleavage of a peptide containing additional 44 aminoacids; this peptide is referred to herein as SORT1 Propeptide or SPP (SEQ ID NO.: 4).

The type of ligands that bind to SORT1 are different from the ligands binding to CI-M6PR, and the sorting of proteins by SORT1 is not dependent on M6P. The function of SORT1 is not fully understood. SORT1 has been implicated, however, in lysosomal transport, neurotrophic signaling, carbohydrate metabolism and lipoprotein metabolism.

Exemplary Lysosomal Targeting Moieties

A suitable lysosomal targeting moiety may be any molecule or a portion of a molecule (e.g., a motif or domain) that can bind to SORT1. As used herein, binding to SORT1 typically refers to a physiologically meaningful binding. For example, a physiologically meaningful binding typically has a dissociation constant (Kd) no greater than $10^{-7}$ under physiological conditions (e.g., pH 6-8, and in particular, pH 7.4).

In some embodiments, a suitable lysosomal targeting moiety is a peptide that binds to SORT1. Suitable peptides may be derived from naturally-occurring ligands that bind SORT1, including, but not limited to SPP, Saposin, and Progranulin.

In some embodiments, a lysosomal targeting moiety is derived from human SORT1 (SEQ ID NO:3). In some embodiments, a SORT1 propeptide (SPP) sequence (SEQ ID NO:4) is used as a lysosomal targeting moiety. The amino acid sequences of a typical wild-type or naturally-occurring human SORT1 and SORT1 propeptide (SPP) are shown in Table 3.

TABLE 3

Human Sortilin-1 Sequences

| | |
|---|---|
| Prosortilin | MERPWGAADGLSRWPHGLGLLLLLQLLPPSTLSQDRLDAPPPPAAPLPRWSGPI<br>GVSWGLRAAAAGGAFPRGGRWRRSAPGEDEECGRVRDFVAKLANNTHQHVFDDL<br>RGSVSLSWVGDSTGVILVLTTFHVPLVIMTFGQSKLYRSEDYGKNFKDITDLIN<br>NTFIRTEFGMAIGPENSGKVVLTAEVSGGSRGGRIFRSSDFAKNFVQTDLPFHP<br>LTQMMYSPQNSDYLLALSTENGLWVSKNFGGKWEEIHKAVCLAKWGSDNTIFFT<br>TYANGSCKADLGALELWRTSDLGKSFKTIGVKIYSFGLGGRFLFASVMADKDTT<br>RRIHVSTDQGDTWSMAQLPSVGQEQFYSILAANDDMVFMHVDEPGDTGFGTIFT<br>SDDRGIVYSKSLDRHLYTTTGGETDFTNVTSLRGVYITSVLSEDNSIQTMITFD<br>QGGRWTHLRKPENSECDATAKNKNECSLHIHASYSISQKLNVPMAPLSEPNAVG<br>IVIAHGSVGDAISVMVPDVYISDDGGYSWTKMLEGPHYYTILDSGGIIVAIEHS<br>SRPINVIKFSTDEGQCWQTYTFTRDPIYFTGLASEPGARSMNISIWGFTESFLT<br>SQWVSYTIDFKDILERNCEEKDYTIWLAHSTDPEDYEDGCILGYKEQFLRLRKS<br>SVCQNGRDYVVTKQPSICLCSLEDFLCDFGYYRPENDSKCVEQPELKGHDLEFC<br>LYGREEHLTTNGYRKIPGDKCQGGVNPVREVKDLKKKCTSNFLSPEKQNSKSNS<br>VPIILAIVGLMLVTVVAGVLIVKKYVCGGRFLVHRYSVLQQHAEANGVDGVDAL<br>DTASHTNKSGYHDDSDEDLLE (SEQ ID NO: 3) |
| SORT1<br>Propeptide<br>(SPP) | QDRLDAPPPPAAPLPRWSGPIGVSWGLRAAAAGGAFPRGGRWRR<br>(SEQ ID NO: 4) |

In some embodiments, a lysosomal targeting moiety is a modified human SORT1 peptide sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to the sequence of human SORT1 (SEQ ID NO:3). In some embodiments, a lysosomal targeting moiety is a fragment of human SORT1. In particular embodiments, a lysosomal targeting moiety contains amino acids 34-77 of human SORT1 (SEQ ID NO:3). In some embodiments, a lysosomal targeting moiety contains an N-terminal, C-terminal or internal deletion in the sequence of human SORT1 (SEQ ID NO:3). In some embodiments, a lysosomal targeting moiety is a modified human SORT1 propeptide (SPP) sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to SPP (SEQ ID NO:4). In some embodiments, a lysosomal targeting moiety is a fragment of SPP. In some embodiments, a lysosomal targeting moiety is a modified human SORT1 peptide or SORT1 propeptide (SPP) that has diminished binding affinity for receptors.

In some embodiments, a lysosomal targeting moiety is derived from human Progranulin (SEQ ID NO:5). In some embodiments, a lysosomal targeting moiety is a Progranulin sequence of a wild-type or naturally-occurring human Progranulin protein. In some embodiments, an amino acid sequence comprising the 24 amino acid C terminal region of Progranulin (SEQ ID NO:6) is used as a lysosomal targeting moiety.

TABLE 4

Human Progranulin Sequences

| | |
|---|---|
| Human<br>Progranulin | MWTLVSWVALTAGLVAGTRCPDGQFCPVACCLDPGGASYSCCRPLLDKWPTTLS<br>RHLGGPCQVDAHCSAGHSCIFTVSGTSSCCPFPEAVACGDGHHCCPRGFHCSAD<br>GRSCFQRSGNNSVGAIQCPDSQFECPDFSTCCVMVDGSWGCCPMPQASCCEDRV<br>HCCPHGAFCDLVHTRCITPTGTHPLAKKLPAQRTNRAVALSSSVMCPDARSRCP<br>DGSTCCELPSGKYGCCPMPNATCCSDHLHCCPQDTVCDLIQSKCLSKENATTDL<br>LTKLPAHTVGDVKCDMEVSCPDGYTCCRLQSGAWGCCPFTQAVCCEDHIHCCPA<br>GFTCDTQKGTCEQGPHQVPWMEKAPAHLSLPDPQALKRDVPCDNVSSCPSSDTC<br>CQLTSGEWGCCPIPEAVCCSDHQHCCPQGYTCVAEGQCQRGSEIVAGLEKMPAR<br>RASLSHPRDIGCDQHTSCPVGQTCCPSLGGSWACCQLPHAVCCEDRQHCCPAGY<br>TCNVKARSCEKEVVSAQPATFLARSPHVGVKDVECGEGHFCHDNQTCCRDNRQG<br>WACCPYRQGVCCADRRHCCPAGFRCAARGTKCLRREAPRWDAPLRDPALRQLL<br>(SEQ ID NO: 5) |
| Human<br>Progranulin<br>C-terminal<br>peptide<br>(tPRGN) | TKCLRREAPRWDAPLRDPALRQLL (SEQ ID NO: 6) |

In some embodiments, a lysosomal targeting moiety is a modified human Progranulin sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to the sequence of human Progranulin (SEQ ID NO:5). In some embodiments, a lysosomal targeting moiety is a fragment of human Progranulin. In some embodiments, a lysosomal targeting moiety is a modified human 24 amino acid C terminal peptide (tPRGN) sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to tPRGN (SEQ ID NO:6). In some embodiments, a lysosomal targeting moiety is a fragment of tPRGN. In some embodiments, a lysosomal targeting moiety contains human Progranulin (SEQ ID NO:5) or tPRGN (SEQ ID NO:6) that has a N-terminal, C-terminal or internal deletion. In some embodiments, a lysosomal targeting moiety is a modified human Progranulin or tPRGN peptide that has diminished binding affinity for receptors.

In some embodiments, a lysosomal targeting moiety is derived from human Prosaposin (SEQ ID NO:7). In some embodiments, a lysosomal targeting moiety is a Prosaposin sequence of a wild-type or naturally-occurring human Prosaposin protein. In some embodiments, an amino acid sequence comprising the C terminal region and D functional domain of Prosaposin (SEQ ID NO:8) is used as a lysosomal targeting moiety.

the lysosomal enzyme at a position where the presence of the targeting moiety does not unduly interfere with the therapeutic activity of the enzyme. Where a lysosomal enzyme is a heteromeric protein, one or more of the subunits can be associated with a targeting moeity.

Linker or Spacer

A lysosomal targeting moiety can be fused to the N-terminus or C-terminus of a polypeptide encoding a lysosomal enzyme, or inserted internally. The lysosomal targeting moiety can be fused directly to the lysosomal enzyme polypeptide or can be separated from the lysosomal enzyme polypeptide by a linker or a spacer. An amino acid linker or spacer is generally designed to be flexible or to interpose a structure, such as an alpha-helix, between the two protein

| Human Prosaposin Sequences | |
|---|---|
| Human Prosaposin | MYALFLLASLLGAALAGPVLGLKECTRGSAVWCQNVKTASDCGAVKHCLQTVWN KPTVKSLPCDICKDVVTAAGDMLKDNATEEEILVYLEKTCDWLPKPNMSASCKE IVDSYLPVILDIIKGEMSRPGEVCSALNLCESLQKHLAELNHQKQLESNKIPEL DMTEVVAPFMANIPLLLYPQDGPRSKPQPKDNGDVCQDCIQMVTDIQTAVRTNS TFVQALVEHVKEECDRLGPGMADICKNYISQYSEIAIQMMMHMQPKEICALVGF CDEVKEMPMQTLVPAKVASKNVIPALELVEPIKKHEVPAKSDVYCEVCEFLVKE VTKLIDNNKTEKEILDAFDKMCSKLPKSLSEECQEVVDTYGSSILSILLEEVSP ELVCSMLHLCSGTRLPALTVHVTQPKDGGFCEVCKKLVGYLDRNLEKNSTKQEI LAALEKGCSFLPDPYQKQCDQFVAEYEPVLIEILVEVMDPSFVCLKIGACPSAH KPLLGTEKCIWGPSYWCQNTETAAQCNAVEHCKRHVWN (SEQ ID NO: 7) |
| Human Prosaposin DC peptide (SapDC) | DGGFCEVCKKLVGYLDRNLEKNSTKQEILAALEKGCSFLPDPYQKQCDQFVAEY EPVLIEILVEVMDPSFVCLKIGACPSAHKPLLGTEKCIWGPSYWCQNTETAAQC NAVEHCKRHVWN (SEQ ID NO: 8) |

In some embodiments, a lysosomal targeting moiety is a modified human Prosaposin sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to the sequence of human Prosaposin (SEQ ID NO:7). In some embodiments, a lysosomal targeting moiety is a fragment of human Prosaposin. In some embodiments, a lysosomal targeting moiety is a modified human Prosaposin DC peptide (SapDC) sequence containing amino acid substitutions, insertions or deletions. In some embodiments, a lysosomal targeting moiety has a sequence at least 50%, 55%, 60%, 65%, 70%, 75%, 80%, 85%, 90%, 95%, 98%, or 99% identical to SapDC (SEQ ID NO:8). In some embodiments, a lysosomal targeting moiety is a fragment of SapDC. In some embodiments, a lysosomal targeting moiety contains human Prosaposin (SEQ ID NO:7) or SapDC (SEQ ID NO:8) that has a N-terminal, C-terminal or internal deletion. In some embodiments, a lysosomal targeting moiety is a modified human Prosaposin or SapDC peptide that has diminished binding affinity for receptors.

Association Between Lysosomal Enzyme and Lysosomal Targeting Moiety

A lysosomal enzyme and a targeting moiety can be associated, directly or indirectly. In some embodiments, a lysosomal enzyme and a targeting moiety are non-covalently associated. The association is typically stable at or about pH 7.4. For example, a targeting moiety can be biotinylated and bind avidin associated with a lysosomal enzyme. In some embodiment, a targeting moiety and a lysosomal enzyme are crosslinked to each other (e.g. using a chemical crosslinking agent).

In some embodiments, a targeting moiety is fused to a lysosomal enzyme as a fusion protein. The targeting moiety can be at the amino-terminus of the fusion protein, the carboxy-terminus, or can be inserted within the sequence of moieties. A linker or spacer can be relatively short, such as a poly "GAG" sequence GGGGGAAAAGGGG (SEQ ID NO:9), a "GAP" sequence of GAP (SEQ ID NO:10), a "PolyGP" sequence of GGGGGP (SEQ ID NO:11), or can be longer, such as, for example, 10-50 (e.g., 10-20, 10-25, 10-30, 10-35, 10-40, 10-45, 10-50) amino acids in length. In some embodiments, various short linker sequences can be present in tandem repeats. For example, a suitable linker may contain the "GAG" amino acid sequence of GGGGGAAAAGGGG (SEQ ID NO:9) present in tandem repeats. In some embodiments, such a linker may further contain one or more "GAP" sequences, that frame the "GAG" sequence of GGGGGAAAAGGGG (SEQ ID NO:9). For example, in some embodiments a GAG2 linker may be used, which contains two tandem "GAG" repeats, each framed by a "GAP" sequence, such as GAPGGGGGAAAAGGGGGAPGGGGGAAAAGGGGGAP (SEQ ID NO:12). In some embodiments a GAG3 linker may be used, which contains three tandem "GAG" repeats, each framed by two "GAP" sequences, such as (SEQ ID NO: 13)
GAPGGGGGAAAAGGGGGAPGGGGGAAAAGGGGGAPGGGGGAAAAG
GGGGAP.

In some embodiments, a suitable linker or spacer may contain a sequence at least 50%, 55%, 60%, 65%, 70%, 75%, 80%, 85%, 90%, 95%, 98%, or 99% identical to any of the linker sequences described herein, including, but not limited to, SEQ ID NO:9, SEQ ID NO:10, SEQ ID NO:11, SEQ ID NO:12, or SEQ ID NO:13.

Additional linkers or spacers suitable for the invention are known in the art including those described in WO 2012122042, entitled "PEPTIDE LINKERS FOR POLYPEPTIDE COMPOSITIONS AND METHODS FOR USING SAME", which is incorporated by reference in its entirety.

It is contemplated that the association between a lysosomal enzyme and a lysosomal targeting moiety according to the present invention does not substantially alter enzyme activity. In some embodiments, the targeted therapeutic has an enzyme activity that is substantially similar or enhanced when compared to the corresponding native enzyme. In some embodiments, the enzyme activity of a targeted therapeutic retains at least about 60%, 65%, 70%, 75%, 80%, 85%, 90%, 95%, 98%, 99%, or 100% enzymatic activity as compared to the native enzyme. In some embodiments, the enzyme activity of a targeted therapeutic is enhanced by at least about 5%, 10%, 15%, 20%, 25%, 30%, 35%, 40%, 45%, 50%, 55%, 60%, 70%, 80%, 90% or 100% compared to the native enzyme.

In some embodiments, a targeted therapeutic of the present invention comprises a Naglu protein fused to a lysosomal targeting moiety. In some embodiments, the enzyme activity of the Naglu protein is at least about 100,000 nmol/hr/mg total protein, at least about 200,000 nmol/hr/mg total protein, or at least about 300,000 nmol/hr/mg total protein. In some embodiments, the Naglu protein has a Km for a known substrate (e.g., methylumbelliferyl-N-acetyl-α-D-glucosainide) of at least about 0.10 nM (e.g., at least about 0.15 nM, 0.20 nM, 0.25 nM, 0.30 nM, or 0.35 nM).

It is also contemplated that the targeted therapeutic of the present invention permits substantial binding between the lysosomal targeting moiety and the SORT1. In some embodiments, the level of SORT1 binding of the targeted therapeutic may be tested using any of a variety of well-known binding assays, such as, but not limited to, radiolabeled run on assay, radiolabeled binding assay, ELISA, Surface Plasmone Resonance and Isothermal Titration calorimetry. In some embodiments, the level of SORT1 binding of the targeted therapeutics of the invention may be evaluated by cellular uptake experiments using cells lines expression endogenous SORT1 at a high enough level or, alternatively, recombinant cell line overexpressing SORT1.

In some embodiments, a targeted therapeutic of the present invention binds to the sortlin-1 receptor. In some embodiments, a targeted therapeutic has an average association constant (ka [1/Ms]) of at least about $1.0 \times 10^5$ (e.g., at least about $1.0 \times 10^6$, $1.0 \times 10^7$, $1.0 \times 10^8$, $1.0 \times 10^9$) for SORT1. In some embodiments, a targeted therapeutic has an average disassociation constant (kd [1/s]) of at least about $1.0 \times 10^{-4}$ (e.g., at least about $1.0 \times 10^{-5}$, $1.0 \times 10^{-6}$, $1.0 \times 10^{-7}$, $1.0 \times 10^{-8}$, $1.0 \times 10^{-9}$) for SORT1. In some embodiments, a targeted therapeutic has an average equilibrium disassociation constant ($K_D[M]$) of at least about $1.0 \times 10^{-7}$ (e.g., at least about $1.0 \times 10^{-8}$, $1.0 \times 10^{-9}$, $1.0 \times 10^{-16}$, $1.0 \times 10^{-11}$, or $1.0 \times 10^{-12}$) for SORT1. In some embodiments, a targeted therapeutic selectively binds SORT1.

In some embodiments, the cellular uptake of a targeted therapeutic according to the present invention has a Kd of at least about 1.0e+2 nM (e.g., at least about 1.0e+3 nM, 1.0e+4 nM, or 1.0e+5 nM).

Production of Targeted Therapeutics

Targeted therapeutics according to the present invention may be produced via various methods known in the art. In some embodiments, a targeted therapeutic is a fusion protein and can be produced recombinantly. For example, a fusion protein according to the invention may be engineered using standard recombinant technology and produced using a cell culture system. Various prokaryotic and eukaryotic cells may be used for producing fusion proteins including, without limitation, cell lines derived from bacteria strains, yeast strains, insect cells, animal cells, mammalian cells and human cells. Aspects of the present invention also provide for expression constructs and the generation of recombinant stable cell lines useful for expressing fusion proteins which are disclosed in the present specification. In addition, aspects of the present invention also provide methods for producing cell lines that express fusion proteins using the disclosed nucleic acid sequences of the present specification.

Nucleic Acids Encoding Recombinant Fusion Proteins

In some embodiments, nucleic acid molecules are provided comprising nucleic acid sequences encoding for a recombinant fusion protein (herein referred to as a transgene), such as Naglu fusion proteins described in various embodiments herein. In some embodiments, the nucleic acid encoding a transgene may be modified to provide increased expression of the fusion protein, which is also referred to as codon optimization. For example, the nucleic acid encoding a transgene can be modified by altering the open reading frame for the coding sequence. As used herein, the term "open reading frame" is synonymous with "ORF" and means any nucleotide sequence that is potentially able to encode a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a nucleic acid molecule that specifies a particular amino acid during protein synthesis; also called a triplet or codon-triplet. For example, of the 64 possible codons in the standard genetic code, two codons, GAA and GAG encode the amino acid Glutamine whereas the codons AAA and AAG specify the amino acid Lysine. In the standard genetic code three codons are stop codons, which do not specify an amino acid. As used herein, the term "synonymous codon" means any and all of the codons that code for a single amino acid. Except for Methionine and Tryptophan, amino acids are coded by two to six synonymous codons. For example, in the standard genetic code the four synonymous codons that code for the amino acid Alanine are GCA, GCC, GCG and GCU, the two synonymous codons that specify Glutamine are GAA and GAG and the two synonymous codons that encode Lysine are AAA and AAG.

In some embodiments, a nucleic acid encoding the open reading frame of fusion protein may be modified using standard codon optimization methods. Various commercial algorithms for codon optimization are available and can be used to practice the present invention. Typically, codon optimization does not alter the encoded amino acid sequences. In some embodiments, codon optimization may lead to amino acids alteration such as substitution, deletion or insertion. Typically, such amino acid alteration does not substantially alter the protein activity.

Exemplary nucleic acid sequences encoding a Full-Length Naglu-SPP, Full-Length Naglu-tPRGN and Full-Length Naglu-SapDC fusion protein, respectively are shown in SEQ ID NO:14, 15 and 16 below.

Exemplary nucleic acid sequence encoding Full-Length Naglu-SPP.
SEQ ID NO:14

ATGGAGGCGGTGGCGGTGGCCGCGGCGGTGGGGGTCCTTCTCCTGGCCGGGGCCGGGGCGCGG

CAGGCGACGAGGCCCGGGAGGCGGCGGCCGTGCGGGCGCTCGTGGCCCGGCTGCTGGGGCCAGG

CCCCGCGGCCGACTTCTCCGTGTCGGTGGAGCGCGCTCTGGCTGCCAAGCCGGGCTTGGACACC

TACAGCCTGGGCGGCGGCGGCGCGGCGCGCGTGCGGGTGCGCGGCTCCACGGGCGTGGCGGCCG

CCGCGGGGCTGCACCGCTACCTGCGCGACTTCTGTGGCTGCCACGTGGCCTGGTCCGGCTCTCA

GCTGCGCCTGCCGCGGCCACTGCCAGCCGTGCCGGGGGAGCTGACCGAGGCCACGCCCAACAGG

TACCGCTATTACCAGAATGTGTGCACGCAAAGCTACTCCTTCGTGTGGTGGGACTGGGCCCGCT

GGGAGCGAGAGATAGACTGGATGGCGCTGAATGGCATCAACCTGGCACTGGCCTGGAGCGGCCA

GGAGGCCATCTGGCAGCGGGTGTACCTGGCCTTGGGCCTGACCCAGGCAGAGATCAATGAGTTC

TTTACTGGTCCTGCCTTCCTGGCCTGGGGGCGAATGGGCAACCTGCACACCTGGGATGGCCCCC

TGCCCCCCTCCTGGCACATCAAGCAGCTTTACCTGCAGCACCGGGTCCTGGACCAGATGCGCTC

CTTCGGCATGACCCCAGTGCTGCCTGCATTCGCGGGCATGTTCCCGAGGCTGTCACCAGGGTG

TTCCCTCAGGTCAATGTCACGAAGATGGGCAGTTGGGGCCACTTTAACTGTTCCTACTCCTGCT

CCTTCCTTCTGGCTCCGGAAGACCCCATATTCCCCATCATCGGGAGCCTCTTCCTGCGAGAGCT

GATCAAAGAGTTTGGCACAGACCACATCTATGGGGCCGACACTTTCAATGAGATGCAGCCACCT

TCCTCAGAGCCCTCCTACCTTGCCGCAGCCACCACTGCCGTCTATGAGGCCATGACTGCAGTGG

ATACTGAGGCTGTGTGGCTGCTCCAAGGCTGGCTCTTCCAGCACCAGCCGCAGTTCTGGGGGCC

CGCCCAGATCAGGGCTGTGCTGGGAGCTGTGCCCCGTGGCCGCCTCCTGGTTCTGGACCTGTTT

GCTGAGAGCCAGCCTGTGTATACCCGCACTGCCTCCTTCCAGGGCCAGCCCTTCATCTGGTGCA

TGCTGCACAACTTTGGGGGAAACCATGGTCTTTTTGGAGCCCTAGAGGCTGTGAACGGAGGCCC

AGAAGCTGCCCGCCTCTTCCCCAACTCCACCATGGTAGGCACGGGCATGGCCCCCGAGGGCATC

AGCCAGAACGAAGTGGTCTATTCCCTCATGGCTGAGCTGGGCTGGCGAAAGGACCCAGTGCCAG

ATTTGGCAGCCTGGGTGACCAGCTTTGCCGCCCGGCGGTATGGGGTCTCCCACCCGGACGCAGG

GGCAGCGTGGAGGCTACTGCTCCGGAGTGTGTACAACTGCTCCGGGGAGGCCTGCAGGGCCAC

AATCGTAGCCCGCTGGTCAGGCGGCCGTCCCTACAGATGAATACCAGCATCTGGTACAACCGAT

CTGATGTGTTTGAGGCCTGGCGGCTGCTGCTCACATCTGCTCCCTCCCTGGCCACCAGCCCCGC

CTTCCGCTACGACCTGCTGGACCTCACTCGGCAGGCAGTGCAGGAGCTGGTCAGCTTGTACTAT

GAGGAGGCAAGAAGCGCCTACCTGAGCAAGGAGCTGGCCTCCCTGTTGAGGGCTGGAGGCGTCC

TGGCCTATGAGCTGCTGCCGGCACTGGACGAGGTGCTGGCTAGTGACAGCCGCTTCTTGCTGGG

CAGCTGGCTAGAGCAGGCCCGAGCAGCGGCAGTCAGTGAGGCCGAGGCCGATTTCTACGAGCAG

AACAGCCGCTACCAGCTGACCTTGTGGGGGCCAGAAGGCAACATCCTGGACTATGCCAACAAGC

AGCTGGCGGGGTTGGTGGCCAACTACTACACCCCTCGCTGGCGGCTTTTCCTGGAGGCGCTGGT

TGACAGTGTGGCCCAGGGCATCCCTTTCCAACAGCACCAGTTTGACAAAAATGTCTTCCAACTG

GAGCAGGCCTTCGTTCTCAGCAAGCAGAGGTACCCCAGCCAGCCGCGAGGAGACACTGTGGACC

TGGCCAAGAAGATCTTCCTCAAATATTACCCCCGCTGGGTGGCCGGCTCTTGGGGCGCGCCAGG

AGGCGGAGGAGGCGCCGCTGCTGCAGCCGGAGGTGGGGGCGGAGGCGCTCCTGGAGGCGGCGGG

GGAGCCGCTGCCGCTGCAGGAGGAGGTGGCGGAGGTGCGCCTGGCGGAGGGGGAGGCGCTGCAG

```
CTGCCGCCGGAGGAGGGGGCGGCGGAGCTCCTCAGGACCGGCTGGACGCGCCGCCGCCGCCCGC

TGCGCCGCTGCCGCGCTGGTCTGGCCCCATCGGGGTGAGCTGGGGGCTGCGGGCGGCCGCAGCC

GGGGGCGCGTTTCCCCGCGGCGGCCGTTGGCGTCGCTAG
```

The nucleotide sequence encoding the amino acid sequence of the GAG3 linker is underlined.

The nucleotide sequence encoding the SPP amino acid sequence is bold and in italics.

```
Exemplary nucleic acid sequence encoding Full-Length Naglu-tPRGN.
                                                     SEQ ID NO:15
ATGGAGGCGGTGGCGGTGGCCGCGGCGGTGGGGGTCCTTCTCCTGGCCGGGGCCGGGGCGCGG

CAGGCGACGAGGCCCGGGAGGCGGCGGCCGTGCGGGCGCTCGTGGCCCGGCTGCTGGGGCCAGG

CCCCGCGGCCGACTTCTCCGTGTCGGTGGAGCGCGCTCTGGCTGCCAAGCCGGGCTTGGACACC

TACAGCCTGGGCGGCGGCGGCGCGGCGCGCGTGCGGGTGCGCGGCTCCACGGGCGTGGCGGCCG

CCGCGGGGCTGCACCGCTACCTGCGCGACTTCTGTGGCTGCCACGTGGCCTGGTCCGGCTCTCA

GCTGCGCCTGCCGCGGCCACTGCCAGCCGTGCCGGGGGAGCTGACCGAGGCCACGCCCAACAGG

TACCGCTATTACCAGAATGTGTGCACGCAAAGCTACTCCTTCGTGTGGTGGGACTGGGCCCGCT

GGGAGCGAGAGATAGACTGGATGGCGCTGAATGGCATCAACCTGGCACTGGCCTGGAGCGGCCA

GGAGGCCATCTGGCAGCGGGTGTACCTGGCCTTGGGCCTGACCCAGGCAGAGATCAATGAGTTC

TTTACTGGTCCTGCCTTCCTGGCCTGGGGCGAATGGGCAACCTGCACACCTGGGATGGCCCCC

TGCCCCCCTCCTGGCACATCAAGCAGCTTTACCTGCAGCACCGGGTCCTGGACCAGATGCGCTC

CTTCGGCATGACCCCAGTGCTGCCTGCATTCGCGGGGCATGTTCCCGAGGCTGTCACCAGGGTG

TTCCCTCAGGTCAATGTCACGAAGATGGGCAGTTGGGGCCACTTTAACTGTTCCTACTCCTGCT

CCTTCCTTCTGGCTCCGGAAGACCCCATATTCCCCATCATCGGGAGCCTCTTCCTGCGAGAGCT

GATCAAAGAGTTTGGCACAGACCACATCTATGGGGCCGACACTTTCAATGAGATGCAGCCACCT

TCCTCAGAGCCCTCCTACCTTGCCGCAGCCACCACTGCCGTCTATGAGGCCATGACTGCAGTGG

ATACTGAGGCTGTGTGGCTGCTCCAAGGCTGGCTCTTCCAGCACCAGCCGCAGTTCTGGGGGCC

CGCCCAGATCAGGGCTGTGCTGGGAGCTGTGCCCCGTGGCCGCCTCCTGGTTCTGGACCTGTTT

GCTGAGAGCCAGCCTGTGTATACCCGCACTGCCTCCTTCCAGGGCCAGCCCTTCATCTGGTGCA

TGCTGCACAACTTTGGGGGAAACCATGGTCTTTTTGGAGCCCTAGAGGCTGTGAACGGAGGCCC

AGAAGCTGCCCGCCTCTTCCCCAACTCCACCATGGTAGGCACGGGCATGGCCCCCGAGGGCATC

AGCCAGAACGAAGTGGTCTATTCCCTCATGGCTGAGCTGGGCTGGCGAAAGGACCCAGTGCCAG

ATTTGGCAGCCTGGGTGACCAGCTTTGCCGCCCGGCGGTATGGGGTCTCCCACCCGGACGCAGG

GGCAGCGTGGAGGCTACTGCTCCGGAGTGTGTACAACTGCTCCGGGGAGGCCTGCAGGGGCCAC

AATCGTAGCCCGCTGGTCAGGCGGCCGTCCCTACAGATGAATACCAGCATCTGGTACAACCGAT

CTGATGTGTTTGAGGCCTGGCGGCTGCTGCTCACATCTGCTCCCTCCCTGGCCACCAGCCCCGC

CTTCCGCTACGACCTGCTGGACCTCACTCGGCAGGCAGTGCAGGAGCTGGTCAGCTTGTACTAT

GAGGAGGCAAGAAGCGCCTACCTGAGCAAGGAGCTGGCCTCCCTGTTGAGGGCTGGAGGCGTCC

TGGCCTATGAGCTGCTGCCGGCACTGGACGAGGTGCTGGCTAGTGACAGCCGCTTCTTGCTGGG

CAGCTGGCTAGAGCAGGCCCGAGCAGCGGCAGTCAGTGAGGCCGAGGCCGATTTCTACGAGCAG

AACAGCCGCTACCAGCTGACCTTGTGGGGGCCAGAAGGCAACATCCTGGACTATGCCAACAAGC
```

-continued

```
AGCTGGCGGGGTTGGTGGCCAACTACTACACCCCTCGCTGGCGGCTTTTCCTGGAGGCGCTGGT

TGACAGTGTGGCCCAGGGCATCCCTTTCCAACAGCACCAGTTTGACAAAAATGTCTTCCAACTG

GAGCAGGCCTTCGTTCTCAGCAAGCAGAGGTACCCCAGCCAGCCGCGAGGAGACACTGTGGACC

TGGCCAAGAAGATCTTCCTCAAATATTACCCCGCTGGGTGGCCGGCTCTTGGGGCGCGCCAGG

AGGCGGAGGAGGCGCCGCTGCTGCAGCCGGAGGTGGGGCGGAGGCGCTCCTGGAGGCGGCGGG

GGAGCCGCTGCCGCTGCAGGAGGAGGTGGCGGAGGTGCGCCTGGCGGAGGGGAGGCGCTGCAG

CTGCCGCCGGAGGAGGGGCGGCGGAGCTCCT``ACCAAGTGTTTGCGCAGGGAGGCCCCGCGCTG``

``GGACGCCCCTTTGAGGGACCCAGCCTTGAGACAGCTGCTGTGA``
```

The nucleotide sequence encoding the amino acid sequence of the GAG3 linker is underlined.

The nucleotide sequence encoding the tPRGN amino acid sequence is bold and in italics.

```
Exemplary nucleic acid sequence encoding Full-Length Naglu-SapDC.
                                                    SEQ ID NO:16
ATGGAGGCGGTGGCGGTGGCCGCGGCGGTGGGGGTCCTTCTCCTGGCCGGGGCCGGGGCGCGG

CAGGCGACGAGGCCCGGGAGGCGGCGGCCGTGCGGGCGCTCGTGGCCCGGCTGCTGGGGCCAGG

CCCCGCGGCCGACTTCTCCGTGTCGGTGGAGCGCGCTCTGGCTGCCAAGCCGGGCTTGGACACC

TACAGCCTGGGCGGCGGCGGCGCGGCGCGCGTGCGGGTGCGCGGCTCCACGGGCGTGGCGGCCG

CCGCGGGGCTGCACCGCTACCTGCGCGACTTCTGTGGCTGCCACGTGGCCTGGTCCGGCTCTCA

GCTGCGCCTGCCGCGGCCACTGCCAGCCGTGCCGGGGGAGCTGACCGAGGCCACGCCCAACAGG

TACCGCTATTACCAGAATGTGTGCACGCAAAGCTACTCCTTCGTGTGGTGGGACTGGGCCCGCT

GGGAGCGAGAGATAGACTGGATGGCGCTGAATGGCATCAACCTGGCACTGGCCTGGAGCGGCCA

GGAGGCCATCTGGCAGCGGGTGTACCTGGCCTTGGGCCTGACCCAGGCAGAGATCAATGAGTTC

TTTACTGGTCCTGCCTTCCTGGCCTGGGGGCGAATGGGCAACCTGCACACCTGGGATGGCCCCC

TGCCCCCCTCCTGGCACATCAAGCAGCTTTACCTGCAGCACCGGGTCCTGGACCAGATGCGCTC

CTTCGGCATGACCCCAGTGCTGCCTGCATTCGCGGGGCATGTTCCCGAGGCTGTCACCAGGGTG

TTCCCTCAGGTCAATGTCACGAAGATGGGCAGTTGGGGCCACTTTAACTGTTCCTACTCCTGCT

CCTTCCTTCTGGCTCCGGAAGACCCCATATTCCCCATCATCGGGAGCCTCTTCCTGCGAGAGCT

GATCAAAGAGTTTGGCACAGACCACATCTATGGGGCCGACACTTTCAATGAGATGCAGCCACCT

TCCTCAGAGCCCTCCTACCTTGCCGCAGCCACCACTGCCGTCTATGAGGCCATGACTGCAGTGG

ATACTGAGGCTGTGTGGCTGCTCCAAGGCTGGCTCTTCCAGCACCAGCCGCAGTTCTGGGGGCC

CGCCCAGATCAGGGCTGTGCTGGAGCTGTGCCCCGTGGCCGCCTCCTGGTTCTGGACCTGTTT

GCTGAGAGCCAGCCTGTGTATACCCGCACTGCCTCCTTCCAGGGCCAGCCCTTCATCTGGTGCA

TGCTGCACAACTTTGGGGGAAACCATGGTCTTTTTGGAGCCCTAGAGGCTGTGAACGGAGGCCC

AGAAGCTGCCCGCCTCTTCCCCAACTCCACCATGGTAGGCACGGGCATGGCCCCCGAGGGCATC

AGCCAGAACGAAGTGGTCTATTCCCTCATGGCTGAGCTGGGCTGGCGAAAGGACCCAGTGCCAG

ATTTGGCAGCCTGGGTGACCAGCTTTGCCGCCCGGCGGTATGGGTCTCCCACCCGGACGCAGG

GGCAGCGTGGAGGCTACTGCTCCGGAGTGTGTACAACTGCTCCGGGGAGGCCTGCAGGGCCAC

AATCGTAGCCCGCTGGTCAGGCGGCCGTCCCTACAGATGAATACCAGCATCTGGTACAACCGAT

CTGATGTGTTTGAGGCCTGGCGGCTGCTGCTCACATCTGCTCCCTCCCTGGCCACCAGCCCCGC

CTTCCGCTACGACCTGCTGGACCTCACTCGGCAGGCAGTGCAGGAGCTGGTCAGCTTGTACTAT
```

```
GAGGAGGCAAGAAGCGCCTACCTGAGCAAGGAGCTGGCCTCCCTGTTGAGGGCTGGAGGCGTCC

TGGCCTATGAGCTGCTGCCGGCACTGGACGAGGTGCTGGCTAGTGACAGCCGCTTCTTGCTGGG

CAGCTGGCTAGAGCAGGCCCGAGCAGCGGCAGTCAGTGAGGCCGAGGCCGATTTCTACGAGCAG

AACAGCCGCTACCAGCTGACCTTGTGGGGGCCAGAAGGCAACATCCTGGACTATGCCAACAAGC

AGCTGGCGGGGTTGGTGGCCAACTACTACACCCCTCGCTGGCGGCTTTTCCTGGAGGCGCTGGT

TGACAGTGTGGCCCAGGGCATCCCTTTCCAACAGCACCAGTTTGACAAAAATGTCTTCCAACTG

GAGCAGGCCTTCGTTCTCAGCAAGCAGAGGTACCCCAGCCAGCCGCGAGGAGACACTGTGGACC

TGGCCAAGAAGATCTTCCTCAAATATTACCCCCGCTGGGTGGCCGGCTCTTGGGGCGCGCCAGG

AGGCGGAGGAGGCGCCGCTGCTGCAGCCGGAGGTGGGGCGGAGGCGCTCCTGGAGGCGGCGGG

GGAGCCGCTGCCGCTGCAGGAGGAGGTGGCGGAGGTGCGCCTGGCGGAGGGGGAGGCGCTGCAG

CTGCCGCCGGAGGAGGGGCGGCGGAGCTCCTGACGGTGGCTTCTGCGAAGTGTGCAAGAAGCT

GGTGGGTTATTTGGATCGCAACCTGGAGAAAAACAGCACCAAGCAGGAGATCCTGGCTGCTCTT

GAGAAAGGCTGCAGCTTCCTGCCAGACCCTTACCAGAAGCAGTGTGATCAGTTTGTGGCAGAGT

ACGAGCCCGTGCTGATCGAGATCCTGGTGGAGGTGATGGATCCTTCCTTCGTGTGCTTGAAAAT

TGGAGCCTGCCCCTCGGCCCATAAGCCCTTGTTGGGAACTGAGAAGTGTATATGGGCCCAAGC

TACTGGTGCCAGAACACAGAGACAGCAGCCCAGTGCAATGCTGTCGAGCATTGCAAACGCCATG

TGTGGAACTAG
```

The nucleotide sequence encoding the amino acid sequence of the GAG3 linker is underlined.
The nucleotide sequence encoding the SapDC amino acid sequence is bold and in italics.

In some embodiments, a nucleotide change may alter a synonymous codon within the open reading frame in order to agree with the endogenous codon usage found in a particular heterologous cell selected for expression. Alternatively or additionally, a nucleotide change may alter the G+C content within the open reading frame to better match the average G+C content of open reading frames found in endogenous nucleic acid sequence present in the heterologous host cell. A nucleotide change may also alter a polymononucleotide region or an internal regulatory or structural site found within a protein sequence. Thus, a variety of modified or optimized nucleotide sequences are envisioned including, without limitation, nucleic acid sequences providing increased expression of a fusion protein in a prokaryotic cell; yeast cell; insect cell; and in a mammalian cell.

Thus, in some embodiments, a nucleic acid encoding a Naglu-SPP fusion protein suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:14. In some embodiments, a nucleic acid encoding a Naglu-tPRGN fusion protein suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:15. In some embodiments, a nucleic acid encoding a Naglu-SapDC fusion protein suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:16. A modified nucleic acid may or may not result in amino acid sequence alterations in a fusion protein. In the event there is amino acid alteration, such alteration typically does not substantially alter the biological activity of the protein.

Expression Vectors

A nucleic acid sequence encoding a fusion protein as described in the present application, can be molecularly cloned (inserted) into a suitable vector for propagation or expression in a host cell. A wide variety of expression vectors can be used to practice the present invention, including, without limitation, a prokaryotic expression vector; a yeast expression vector; an insect expression vector and a mammalian expression vector. Exemplary vectors suitable for the present invention include, but are not limited to, viral based vectors (e.g., AAV based vectors, retrovirus based vectors, plasmid based vectors). Typically, a nucleic acid encoding a fusion protein is operably linked to various regulatory sequences or elements.

Regulatory Sequences or Elements

Various regulatory sequences or elements may be incorporated in an expression vector suitable for the present invention. Exemplary regulatory sequences or elements include, but are not limited to, promoters, enhancers, repressors or suppressors, 5' untranslated (or non-coding) sequences, introns, 3' untranslated (or non-coding) sequences.

As used herein, a "Promoter" or "Promoter sequence" is a DNA regulatory region capable of binding an RNA polymerase in a cell (e.g., directly or through other promoter bound proteins or substances) and initiating transcription of a coding sequence. A promoter sequence is, in general, bound at its 3' terminus by the transcription initiation site and extends upstream (5' direction) to include the minimum number of bases or elements necessary to initiate transcription at any level. The promoter may be operably associated with or operably linked to the expression control sequences, including enhancer and repressor sequences or with a nucleic acid to be expressed. In some embodiments, the promoter may be inducible. In some embodiments, the inducible promoter may be unidirectional or bio-directional. In some embodiments, the promoter may be a constitutive promoter. In some embodiments, the promoter can be a hybrid promoter, in which the sequence containing the transcriptional regulatory region is obtained from one source and the sequence containing the transcription initiation region is obtained from a second source. Systems for linking control elements to coding sequence within a transgene are well known in the art (general molecular biological and recombinant DNA techniques are described in Sambrook, Fritsch, and Maniatis, *Molecular Cloning: A Laboratory Manual*, Second Edition, Cold Spring Harbor Laboratory Press, Cold Spring Harbor, N.Y., 1989, which is incorporated herein by reference). Commercial vectors suitable for inserting a transgene for expression in various host cells under a variety of growth and induction conditions are also well known in the art.

In some embodiments, a specific promoter may be used to control expression of the transgene in a mammalian host cell such as, but are not limited to, SRα-promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), human CMV promoter, the human CMV5 promoter, the murine CMV immediate early promoter, the EF1-α-promoter, a hybrid CMV promoter for liver specific expression (e.g., made by conjugating CMV immediate early promoter with the transcriptional promoter elements of either human α-1-antitrypsin (HAT) or albumin (HAL) promoter), or promoters for hepatoma specific expression (e.g., wherein the transcriptional promoter elements of either human albumin (HAL; about 1000 bp) or human α-1-antitrypsin (HAT, about 2000 bp) are combined with a 145 long enhancer element of human α-1-microglobulin and bikunin precursor gene (AMBP); HAL-AMBP and HAT-AMBP); the SV40 early promoter region (Benoist at al., Nature 290:304-310 (1981)), the *Orgyia pseudotsugata* immediate early promoter, the herpes thymidine kinase promoter (Wagner at al., Proc. Natl. Acad. Sci. USA 78:1441-1445 (1981)); or the regulatory sequences of the metallothionein gene (Brinster et al., Nature 296:39-42 (1982)). In some embodiments, the mammalian promoter is a is a constitutive promoter such as, but not limited to, the hypoxanthine phosphoribosyl transferase (HPTR) promoter, the adenosine deaminase promoter, the pyruvate kinase promoter, the beta-actin promoter as well as other constitutive promoters known to those of ordinary skill in the art.

In some embodiments, a specific promoter may be used to control expression of a transgene in a prokaryotic host cell such as, but are not limited to, the β-lactamase promoter (Villa-Komaroff et al., Proc. Natl. Acad. Sci. USA 75:3727-3731 (1978)); the tac promoter (DeBoer et al., Proc. Natl. Acad. Sci. USA 80:21-25 (1983)); the T7 promoter, the T3 promoter, the M13 promoter or the M16 promoter; in a yeast host cell such as, but are not limited to, the GAL1, GAL4 or GAL10 promoter, the ADH (alcohol dehydrogenase) promoter, PGK (phosphoglycerol kinase) promoter, alkaline phosphatase promoter, glyceraldehyde-3-phosphate dehydrogenase III (TDH3) promoter, glyceraldehyde-3-phosphate dehydrogenase II (TDH2) promoter, glyceraldehyde-3-phosphate dehydrogenase I (TDH1) promoter, pyruvate kinase (PYK), enolase (ENO), or triose phosphate isomerase (TPI).

In some embodiments, the promoter may be a viral promoter, many of which are able to regulate expression of a transgene in several host cell types, including mammalian cells. Viral promoters that have been shown to drive constitutive expression of coding sequences in eukaryotic cells include, for example, simian virus promoters, herpes simplex virus promoters, papilloma virus promoters, adenovirus promoters, human immunodeficiency virus (HIV) promoters, Rous sarcoma virus promoters, cytomegalovirus (CMV) promoters, the long terminal repeats (LTRs) of Moloney murine leukemia virus and other retroviruses, the thymidine kinase promoter of herpes simplex virus as well as other viral promoters known to those of ordinary skill in the art.

In some embodiments, the gene control elements of an expression vector may also include 5' non-transcribing and 5' non-translating sequences involved with the initiation of transcription and translation, respectively, such as a TATA box, capping sequence, CAAT sequence, Kozak sequence and the like. Enhancer elements can optionally be used to increase expression levels of a polypeptide or protein to be expressed. Examples of enhancer elements that have been shown to function in mammalian cells include the SV40 early gene enhancer, as described in Dijkema et al., EMBO J. (1985) 4: 761 and the enhancer/promoter derived from the long terminal repeat (LTR) of the Rous Sarcoma Virus (RSV), as described in Gorman et al., Proc. Natl. Acad. Sci. USA (1982b) 79:6777 and human cytomegalovirus, as described in Boshart et al., Cell (1985) 41:521. Genetic control elements of an expression vector will also include 3' non-transcribing and 3'non-translating sequences involved with the termination of transcription and translation. Respectively, such as a poly polyadenylation (polyA) signal for stabilization and processing of the 3' end of an mRNA transcribed from the promoter. Poly A signals included, for example, the rabbit beta globin polyA signal, bovine growth hormone polyA signal, chicken beta globin terminator/polyA signal, or SV40 late polyA region.

Selectable Markers

Expression vectors will preferably but optionally include at least one selectable marker. In some embodiments, the selectable maker is a nucleic acid sequence encoding a resistance gene operably linked to one or more genetic regulatory elements, to bestow upon the host cell the ability to maintain viability when grown in the presence of a cyctotoxic chemical and/or drug. In some embodiments, a selectable agent may be used to maintain retention of the expression vector within the host cell. In some embodiments, the selectable agent is may be used to prevent modification (i.e. methylation) and/or silencing of the transgene sequence within the expression vector. In some embodiments, a selectable agent is used to maintain episomal expression of the vector within the host cell. In some embodiments, the selectable agent is used to promote stable integration of the transgene sequence into the host cell genome. In some embodiments, an agent and/or resistance gene may include, but is not limited to, methotrexate (MTX), dihydrofolate reductase (DHFR, U.S. Pat. Nos. 4,399,216; 4,634,665; 4,656,134; 4,956,288; 5,149,636;

5,179,017, ampicillin, neomycin (G418), zeomycin, mycophenolic acid, or glutamine synthetase (GS, U.S. Pat. Nos. 5,122,464; 5,770,359; 5,827,739) for eukaryotic host cell; tetracycline, ampicillin, kanamycin or chlorampenichol for a prokaryotic host cell; and URA3, LEU2, HIS3, LYS2, HIS4, ADE8, CUP1 or TRP1 for a yeast host cell.

Expression vectors may be transfected, transformed or transduced into a host cell. As used herein, the terms "transfection," "transformation" and "transduction" all refer to the introduction of an exogenous nucleic acid sequence into a host cell. In some embodiments, expression vectors containing nucleic acid sequences encoding a fusion therapeutic glycoprotein is transfected, transformed or transduced into a host cell. In some embodiments, one or more expression vectors containing nucleic acid sequences encoding a fusion therapeutic glycoprotein are transfected, transformed or transduced into a host cell sequentially. For example, a vector encoding a first fusion therapeutic glycoprotein protein may be transfected, transformed or transduced into a host cell, followed by the transfection, transformation or transduction of a vector encoding a second fusion therapeutic glycoprotein, and vice versa. Examples of transformation, transfection and transduction methods, which are well known in the art, include liposome delivery, i.e., Lipofectamine™ (Gibco BRL) Method of Hawley-Nelson, Focus 15:73 (1193), electroporation, CaPO$_4$ delivery method of Graham and van der Erb, *Virology*, 52:456-457 (1978), DEAE-Dextran medicated delivery, microinjection, biolistic particle delivery, polybrene mediated delivery, cationic mediated lipid delivery, transduction, and viral infection, such as, e.g., retrovirus, lentivirus, adenovirus adeno-associated virus and Baculovirus (Insect cells). General aspects of cell host transformations have been described in the art, such as by Axel in U.S. Pat. No. 4,399,216; Sambrook, supra, Chapters 1-4 and 16-18; Ausubel, supra, chapters 1, 9, 13, 15, and 16. For various techniques for transforming mammalian cells, see Keown et al., *Methods in Enzymology* (1989), Keown et al., *Methods in Enzymology*, 185:527-537 (1990), and Mansour et al., *Nature*, 336:348-352 (1988).

Once introduced inside cells, expression vectors may be integrated stably in the genome or exist as extra-chromosomal constructs. Vectors may also be amplified and multiple copies may exist or be integrated in the genome. In some embodiments, cells of the invention may contain 1, 2, 3, 4, 5, 6, 7, 8, 9, 10, 15, 20 or more copies of nucleic acids encoding a fusion therapeutic glycoprotein. In some embodiments, cells of the invention may contain multiple copies (e.g., 2, 3, 4, 5, 6, 7, 8, 9, 10, 15, 20 or more) of nucleic acids encoding one or more fusion therapeutic glycoproteins.

Mammalian Cell Lines

Any mammalian cell or cell type susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). In some embodiments, a suitable mammalian cell is not a endosomal acidification-deficient cell.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Non-Mammalian Cell Lines

Any non-mammalian derived cell or cell type susceptible to cell culture, and to expression of polypeptides, may be utilized in accordance with the present invention as a host cell. Non-limiting examples of non-mammalian host cells and cell lines that may be used in accordance with the present invention include cells and cell lines derived from *Pichia pastoris, Pichia methanolica, Pichia angusta, Schizosacccharomyces pombe, Saccharomyces cerevisiae,* and *Yarrowia lipolytica* for yeast; *Sodoptera frugiperda, Trichoplusis ni, Drosophila melangoster* and *Manduca sexta* for insects; and *Escherichia coli, Salmonella typhimurium, Bacillus subtilis, Bacillus licheniformis, Bacteroides fragilis, Clostridia perfringens, Clostridia difficile* for bacteria; and *Xenopus Laevis* from amphibian.

In other embodiments, transgenic nonhuman mammals have been shown to produce therapeutic glycoproteins (e.g., lysosomal enzymes) in their milk. Such transgenic nonhuman mammals may include mice, rabbits, goats, sheep, porcines or bovines. See U.S. Pat. Nos. 6,118,045 and 7,351,410, each of which are hereby incorporated by reference in their entirety.

Any and all methods suitable for producing recombinant protein can be used to produce therapeutic protein of the present invention.

Pharmaceutical Compositions and Administration

The present invention further provides pharmaceutical compositions containing targeted therapeutics according to the present invention. Typically, suitable pharmaceutical compositions contain at least one pharmaceutically acceptable excipient and are formulated for administration to humans.

For example, pharmaceutical compositions provided herein may be provided in a sterile injectable form (e.g., a form that is suitable for subcutaneous, intravenous, or intrathecal injection). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

Compositions of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, pharmaceutical compositions according to the present invention can be used for CNS delivery via various techniques and routes including, but not limited to, intraparenchymal, intracerebral, intraventricular cerebral (ICV), intrathecal (e.g., IT-Lumbar, IT-cisterna magna) administrations and any other techniques and routes for injection directly or indirectly to the CNS and/or CSF.

Intrathecal Delivery

In some embodiments, pharmaceutical compositions according to the present invention can be used for intrathecal administration. As used herein, intrathecal administration (also referred to as intrathecal injection or intrathecal delivery) refers to an injection into the spinal canal (intrathecal space surrounding the spinal cord). Various formulations for intrathecal administration are described in WO/2011/163652, the contents of which are incorporated herein by reference.

According to the present invention, a pharmaceutical composition containing a targeted therapeutics may be injected at any region surrounding the spinal canal. In some embodiments, a pharmaceutical composition containing a targeted therapeutics is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration."

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

Treatment of San B and Other Lysosomal Storage Diseases

The present invention may be used to effectively treat Sanfilippo Syndrome Type B and other lysosomal storage diseases. Sanfilippo Syndrome Type B, or Mucopolysaccharidosis III B (MPS III B), is an X-linked heritable metabolic disorder resulting from a deficiency of the enzyme Naglu. Naglu is localized to lysosomes and plays an important role in the catabolism of glycosaminoglycans (GAGs) heparan- and dermatan-sulfate. In the absence of enzyme, these substrates accumulate within cells, ultimately causing engorgement, followed by cellular death and tissue destruction. Due to the widespread expression of enzyme, multiple cell types and organ systems are affected in MPS III B patients.

A defining clinical feature of this disorder is central nervous system (CNS) degeneration, which results in cognitive impairment (e.g., decrease in IQ). Additionally, MRI scans of affected individuals have revealed white matter lesions, dilated perivascular spaces in the brain parenchyma, ganglia, corpus callosum, and brainstem; atrophy; and ventriculomegaly (Wang et al. Molecular Genetics and Metabolism, 2009). The disease typically manifests itself in the first years of life with organomegaly and skeletal abnormalities. Some affected individuals experience a progressive loss of cognitive function, with most affected individuals dying of disease-associated complications in their first or second decade.

Compositions and methods of the present invention may be used to effectively treat individuals suffering from or susceptible to Sanfilippo Syndrome Type B. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a Sanfilippo Syndrome Type B patient. As used herein, the term "neurological impairment" includes various symptoms associated with impairment of the central nervous system (e.g., the brain and spinal cord). Symptoms of neurological impairment may include, for example, e.g., cognitive impairment; white matter lesions; dilated perivascular spaces in the brain parenchyma, ganglia, corpus callosum, and/or brainstem; atrophy; and/or ventriculomegaly, among others.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with a lysosomal storage disease (e.g., Sanfilippo Syndrome Type B), who is about the same age and/or gender as the individual suffering from the same lysosomal storage disease, who is being treated (to ensure that the stages of the disease in the treated individual and the control individual(s) are comparable).

The individual (also referred to as "patient" or "subject") being treated is an individual (fetus, infant, child, adolescent, or adult human) having a lysosomal storage disease or having the potential to develop a lysosomal storage disease. In some embodiments, the lysosomal storage disease is Sanfilippo Syndrome. In some specific embodiments the lysosomal storage disease is Sanfilippo Syndrome Type B. The individual can have residual endogenous Naglu expression and/or activity, or no measurable activity. For example, the individual having Sanfilipo Syndrome Type B may have Naglu expression levels that are less than about 30-50%, less than about 25-30%, less than about 20-25%, less than about 15-20%, less than about 10-15%, less than about 5-10%, less than about 0.1-5% of normal Naglu expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

All literature citations herein are incorporated herein by reference in their entirety.

The invention will be more fully understood by reference to the following examples. They should not, however, be construed as limiting the scope of the invention.

EXAMPLES

Example 1: Generation of Naglu Fusion Proteins

Overview: The present invention, among other things, sets out to identify and characterize moieties capable of targeting therapeutic proteins to lysosomes for the treatment of lysosomal storage diseases by ERT. For the following examples, the lysosomal enzyme N-Acetylglucosaminidase (Naglu) was chosen as a representative therapeutic protein since deficiency of Naglu causes Sanpfilippo Syndrome (Mucopolysaccharidosis III) Type B. However, it will be understood by one skilled in the art that the present invention is broadly applicable to the targeting of any therapeutic protein that may be used for treatment of conditions associated with lysosomal storage diseases. It is contemplated that targeting moieties of the current invention, which may be peptides for example, facilitate cellular uptake and lysosomal targeting of therapeutic enzymes, and that such targeted enzymes have an activity substantially similar to the native enzyme.

Targeting peptides may be associated with suitable therapeutic enzymes (e.g., lysosomal enzymes) covalently or non-covalently. For example, a targeting peptide may be chemically conjugated to a therapeutic enzyme. Alternatively, a targeting peptide may be linked to a therapeutic enzyme genetically, thereby creating a fusion protein. In the example below, a series of four DNA constructs were created, each designed to express a different Naglu fusion protein.

Naglu-SPP

To generate an exemplary Full-Length Naglu-SPP fusion protein (SEQ ID NO:17), an exemplary DNA construct was created by connecting DNA encoding human Full-Length Naglu Protein (SEQ ID NO:2) to a DNA encoding SPP (SEQ ID NO:4) via an intervening GAG3-encoding linker.

(SEQ ID NO: 17)
MEAVAVAAAVGVLLLAGAGGAAGDEAREAAAVRALVARLLGPGPAADFSV

SVERALAAKPGLDTYSLGGGGAARVRVRGSTGVAAAAGLHRYLRDFCGCH

VAWSGSQLRLPRPLPAVPGELTEATPNRYRYYQNVCTQSYSFVWWDWARW

EREIDWMALNGINLALAWSGQEAIWQRVYLALGLTQAEINEFFTGPAFLA

WGRMGNLHTWDGPLPPSWHIKQLYLQHRVLDQMRSFGMTPVLPAFAGHVP

EAVTRVFPQVNVTKMGSWGHFNCSYSCSFLLAPEDPIFPIIGSLFLRELI

KEFGTDHIYGADTFNEMQPPSSEPSYLAAATTAVYEAMTAVDTEAVWLLQ

GWLFQHQPQFWGPAQIRAVLGAVPRGRLLVLDLFAESQPVYTRTASFQGQ

PFIWCMLHNFGGNHGLFGALEAVNGGPEAARLFPNSTMVGTGMAPEGISQ

NEVVYSLMAELGWRKDPVPDLAAWVTSFAARRYGVSHPDAGAAWRLLLRS

VYNCSGEACRGHNRSPLVRRPSLQMNTSIWYNRSDVFEAWRLLLTSAPSL

ATSPAFRYDLLDLTRQAVQELVSLYYEEARSAYLSKELASLLRAGGVLAY

ELLPALDEVLASDSRFLLGSWLEQARAAAVSEAEADFYEQNSRYQLTLWG

PEGNILDYANKQLAGLVANYYTPRWRLFLEALVDSVAQGIPFQQHQFDKN

VFQLEQAFVLSKQRYPSQPRGDTVDLAKKIFLKYYPRWVAGSWGAPGGGG

GAAAAAGGGGGAPGGGGGAAAAAGGGGGAPGGGGGAAAAAGGGGGAP

QDRLDAPPPPAAPLPRWSGPIGVSWGLRAAAAGGAFPRGGRWRR

Human Full-Length Naglu—in italics
GAG3 Linker—in bold
SPP—underlined
Naglu-tPRGN To generate an exemplary Full-Length Naglu-tPRGN fusion protein (SEQ ID NO:18), an exemplary DNA construct was created by connecting DNA encoding human Full-Length Naglu Protein (SEQ ID NO:2) to a DNA encoding tPRGN (SEQ ID NO:6) via an intervening GAG3-encoding linker.

(SEQ ID NO: 18)
*MEAVAVAAAVGVLLLAGAGGAAGDEAREAAAVRALVARLLGPGPAADFSV*

*SVERALAAKPGLDTYSLGGGGAARVRVRGSTGVAAAAGLHRYLRDFCGCH*

*VAWSGSQLRLPRPLPAVPGELTEATPNRYRYYQNVCTQSYSFVWWDWARW*

*EREIDWMALNGINLALAWSGQEAIWQRVYLALGLTQAEINEFFTGPAFLA*

*WGRMGNLHTWDGPLPPSWHIKQLYLQHRVLDQMRSFGMTPVLPAFAGHVP*

*EAVTRVFPQVNVTICMGSWGHFNCSYSCSFLLAPEDPIFPIIGSLFLREL*

*IKEFGTDHIYGADTFNEMQPPSSEPSYLAAATTAVYEAMTAVDTEAVWLL*

*QGWLFQHQPQFWGPAQIRAVLGAVPRGRLLVLDLFAESQPVYTRTASFQG*

*QPFIWCMLHNFGGNHGLFGALEAVNGGPEAARLFPNSTMVGTGMAPEGIS*

*QNEVVYSLMAELGWRKDPVPDLAAWVTSFAARRYGVSHPDAGAAWRLLLR*

*SVYNCSGEACRGHNRSPLVRRPSLQMNTSIWYNRSDVFEAWRLLLTSAPS*

*LATSPAFRYDLLDLTRQAVQELVSLYYEEARSAYLSKELASLLRAGGVLA*

*YELLPALDEVLASDSRFLLGSWLEQARAAAVSEAEADFYEQNSRYQLTLW*

*GPEGNILDYANKQLAGLVANYYTPRWRLFLEALVDSVAQGIPFQQHQFDK*

*NVFQLEQAFVLSKQRYPSQPRGDTVDLAKKIFLKYYPRWVAGSW*GAPGGG

GGAAAAAGGGGGAPGGGGAAAAAGGGGGAPGGGGAAAAAGGGGGA

<u>PTKCLRREAPRWDAPLRDPALRQLL</u>

Human Full-Length Naglu—in italics
GAG3 Linker—in bold
tPRGN—underlined
Naglu-SapDC To generate an exemplary Full-Length Naglu-SapDC fusion protein (SEQ ID NO:19), an exemplary DNA construct was created by connecting DNA encoding human Full-Length Naglu Protein (SEQ ID NO:2) to a DNA encoding SapDC (SEQ ID NO: 8) via an intervening GAG3-encoding linker.

(SEQ ID NO: 19)
*MEAVAVAAAVGVLLLAGAGGAAGDEAREAAAVRALVARLLGPGPAADFSV*

*SVERALAAKPGLDTYSLGGGGAARVRVRGSTGVAAAAGLHRYLRDFCGCH*

*VAWSGSQLRLPRPLPAVPGELTEATPNRYRYYQNVCTQSYSFVWWDWARW*

*EREIDWMALNGINLALAWSGQEAIWQRVYLALGLTQAEINEFFTGPAFLA*

*WGRMGNLHTWDGPLPPSWHIKQLYLQHRVLDQMRSFGMTPVLPAFAGHVP*

*EAVTRVFPQVNVTKMGSWGHFNCSYSCSFLLAPEDPIFPIIGSLFLRELI*

*KEFGTDHIYGADTFNEMQPPSSEPSYLAAATTAVYEAMTAVDTEAVWLLQ*

*GWLFQHQPQFWGPAQIRAVLGAVPRGRLLVLDLFAESQPVYTRTASFQGQ*

*PFIWCMLHNFGGNHGLFGALEAVNGGPEAARLFPNSTMVGTGMAPEGISQ*

*NEVVYSLMAELGWRKDPVPDLAAWVTSFAARRYGVSHPDAGAAWRLLLRS*

*VYNCSGEACRGHNRSPLVRRPSLQMNTSIWYNRSDVFEAWRLLLTSAPSL*

*ATSPAFRYDLLDLTRQAVQELVSLYYEEARSAYLSKELASLLRAGGVLAY*

*ELLPALDEVLASDSRFLLGSWLEQARAAAVSEAEADFYEQNSRYQLTLWG*

*PEGNILDYANKQLAGLVANYYTPRWRLFLEALVDSVAQGIPFQQHQFDKN*

*VFQLEQAFVLSKQRYPSQPRGDTVDLAKKIFLKYYPRWVAGSW*GAPGGGG

GAAAAAGGGGGAPGGGGAAAAAGGGGGAPGGGGAAAAAGGGGGAP

<u>DGGFCEVCKKLVGYLDRNLEKNSTKQEILAALEKGCSFLPDPYQKQCDQF</u>

<u>VAEYEPVLIEILVEVMDPSFVCLKIGACPSAHKPLLGTEKCIWGPSYWCQ</u>
<u>NTETAAQCNAVEHCKRHVWN</u>

Human Full-Length Naglu—in italics
GAG3 Linker—in bold
SapDC—underlined
Naglu-IGFII To generate a Full-Length Naglu-IGFII fusion protein (SEQ ID NO:20), an exemplary DNA construct was created by connecting DNA encoding human Full-Length Naglu Protein (SEQ ID NO:2) to a DNA encoding a portion (amino acid residues 8-67, IGFII [SEQ ID NO: 21]) of the Insulin-like Growth Factor II peptide sequence via an intervening GAG3-encoding linker.

The IGF-II sequence containing amino acid 8-67 has been reported to bind to the M6P/IGF II receptor (also known as cation-independent mannose-6-phosphate receptor) with a 2-10 fold higher affinity while its ability to bind to the IGF-I receptor is decreased by 30-fold, as compared to the full-length IGF-II (Hashimoto R, JBC 1995 270(30):18013-18018).

(SEQ ID NO: 20)
*MEAVAVAAAVGVLLLAGAGGAAGDEAREAAAVRALVARLLGPGPAADFSV*

*SVERALAAKPGLDTYSLGGGGAARVRVRGSTGVAAAAGLHRYLRDFCGCH*

*VAWSGSQLRLPRPLPAVPGELTEATPNRYRYYQNVCTQSYSFVWWDWARW*

*EREIDWMALNGINLALAWSGQEAIWQRVYLALGLTQAEINEFFTGPAFLA*

*WGRMGNLHTWDGPLPPSWHIKQLYLQHRVLDQMRSFGMTPVLPAFAGHVP*

*EAVTRVFPQVNVTKMGSWGHFNCSYSCSFLLAPEDPIFPIIGSLFLRELI*

*KEFGTDHIYGADTFNEMQPPSSEPSYLAAATTAVYEAMTAVDTEAVWLLQ*

*GWLFQHQPQFWGPAQIRAVLGAVPRGRLLVLDLFAESQPVYTRTASFQGQ*

*PFIWCMLHNFGGNHGLFGALEAVNGGPEAARLFPNSTMVGTGMAPEGISQ*

*NEVVYSLMAELGWRKDPVPDLAAWVTSFAARRYGVSHPDAGAAWRLLLRS*

*VYNCSGEACRGHNRSPLVRRPSLQMNTSIWYNRSDVFEAWRLLLTSAPSL*

*ATSPAFRYDLLDLTRQAVQELVSLYYEEARSAYLSKELASLLRAGGVLAY*

*ELLPALDEVLASDSRFLLGSWLEQARAAAVSEAEADFYEQNSRYQLTLWG*

*PEGNILDYANKQLAGLVANYYTPRWRLFLEALVDSVAQGIPFQQHQFDKN*

*VFQLEQAFVLSKQRYPSQPRGDTVDLAKKIFLKYYPRWVAGSW*GAPGGGG

GAAAAAGGGGGGAPGGGGGAAAAAGGGGGGAPGGGGGAAAAAGGGGGGAP

<u>LCGGELVDTLQFVCGDRGFYFSRPASRVSRRSRGIVEECCFRSCDLALLE</u>

<u>TYCATPAKSE</u>

Human Full-Length Naglu—in italics
GAG3 Linker—in bold
IGFII—underlined (SEQ ID NO: 21)
LCGGELVDTLQFVCGDRGFYFSRPASRVSRRSRGIVEECCFRSCDLALLE
TYCATPAKSE The nucleic acid encoding each different Naglu fusion protein was subcloned into a mammalian expression vector and transfected into human cells from which over-expressing cell lines were derived using standard protocolls. For all in vitro protein based assays and receptor binding experiments, recombinant protein was produced in a wave bioreactor, using a mammalian cell culture expressing system. Following expression, each fusion protein was subjected to a three step purification process. First, the conditioned media was concentrated using an ultra-filtration (UF) device. Then, the fusion protein was purified to greater than 90% purity first by butyl sepharose and then Q sepharose chromatography. The purified fusion protein was transferred into PBS (11.9 mM sodium phosphate, 2.7 mM potassium phosphate, 137 mM sodium chloride at pH 7.4) for storage. The purified proteins were examined by electrophoresis on a SDS-PAGE gel and compared to bovine serum albumin (BSA) to demonstrate the purity of the protein. One example SDS-PAGE gel for Naglu-SPP is shown in FIG. 1.

SEQ ID NO:17-20 are the amino acid sequences of Full-Length Naglu fusion proteins, which still contain those 23 N-terminal amino acids of the Full-Length Naglu protein that are removed during intracellular processing. The amino acid sequences provided below (SEQ ID NO:22-25) are the corresponding sequences that do not include these 23 N-terminal amino acids.

Naglu-SPP:

(SEQ ID NO: 22)
DEAREAAAVRALVARLLGPGPAADFSVSVERALAAKPGLDTYSLGGGGAA

RVRVRGSTGVAAAAGLHRYLRDFCGCHVAWSGSQLRLPRPLPAVPGELTE

ATPNRYRYYQNVCTQSYSFVWWDWARWEREIDWMALNGINLALAWSGQEA

IWQRVYLALGLTQAEINEFFTGPAFLAWGRMGNLHTWDGPLPPSWHIKQL

YLQHRVLDQMRSFGMTPVLPAFAGHVPEAVTRVFPQVNVTKMGSWGHFNC

SYSCSFLLAPEDPIFPIIGSLFLRELIKEFGTDHIYGADTFNEMQPPSSE

PSYLAAATTAVYEAMTAVDTEAVWLLQGWLFQHQPQFWGPAQIRAVLGAV

PRGRLLVLDLFAESQPVYTRTASFQGQPFIWCMLHNFGGNHGLFGALEAV

NGGPEAARLFPNSTMVGTGMAPEGISQNEVVYSLMAELGWRKDPVPDLAA

WVTSFAARRYGVSHPDAGAAWRLLLRSVYNCSGEACRGHNRSPLVRRPSL

QMNTSIWYNRSDVFEAWRLLLTSAPSLATSPAFRYDLLDLTRQAVQELVS

LYYEEARSAYLSKELASLLRAGGVLAYELLPALDEVLASDSRFLLGSWLE

QARAAAVSEAEADFYEQNSRYQLTLWGPEGNILDYANKQLAGLVANYYTP

RWRLFLEALVDSVAQGIPFQQHQFDKNVFQLEQAFVLSKQRYPSQPRGDT

VDLAKKIFLKYYPRWVAGSWGAPGGGGGAAAAAGGGGGGAPGGGGGAAAA

AGGGGGGAPGGGGGAAAAAGGGGGGAPQDRLDAPPPPAAPLPRWSGPIGV

SWGLRAAAAGGAFPRGGRWRR

Human Naglu—in italics
GAG3 Linker—in bold
SPP—underlined

Naglu-tPRGN:

(SEQ ID NO: 23)
DEAREAAAVRALVARLLGPGPAADFSVSVERALAAKPGLDTYSLGGGGAA

RVRVRGSTGVAAAAGLHRYLRDFCGCHVAWSGSQLRLPRPLPAVPGELTE

ATPNRYRYYQNVCTQSYSFVWWDWARWEREIDWMALNGINLALAWSGQEA

IWQRVYLALGLTQAEINEFFTGPAFLAWGRMGNLHTWDGPLPPSWHIKQL

YLQHRVLDQMRSFGMTPVLPAFAGHVPEAVTRVFPQVNVTKMGSWGHFNC

SYSCSFLLAPEDPIFPIIGSLFLRELIKEFGTDHIYGADTFNEMQPPSSE

PSYLAAATTAVYEAMTAVDTEAVWLLQGWLFQHQPQFWGPAQIRAVLGAV

PRGRLLVLDLFAESQPVYTRTASFQGQPFIWCMLHNFGGNHGLFGALEAV

NGGPEAARLFPNSTMVGTGMAPEGISQNEVVYSLMAELGWRKDPVPDLAA

WVTSFAARRYGVSHPDAGAAWRLLLRSVYNCSGEACRGHNRSPLVRRPSL

QMNTSIWYNRSDVFEAWRLLLTSAPSLATSPAFRYDLLDLTRQAVQELVS

LYYEEARSAYLSKELASLLRAGGVLAYELLPALDEVLASDSRFLLGSWLE

QARAAAVSEAEADFYEQNSRYQLTLWGPEGNILDYANKQLAGLVANYYTP

RWRLFLEALVDSVAQGIPFQQHQFDKNVFQLEQAFVLSKQRYPSQPRGDT

VDLAKKIFLKYYPRWVAGSWGAPGGGGGAAAAAGGGGGGAPGGGGGAAAA

AGGGGGGAPGGGGGAAAAAGGGGGGAP<u>TKCLRREAPRWDAPLRDPALRQL</u>

<u>L</u>

Human Naglu—in italics
GAG3 Linker—in bold
tPRGN—underlined

Naglu-SapDC:

(SEQ ID NO: 24)
DEAREAAAVRALVARLLGPGPAADFSVSVERALAAKPGLDTYSLGGGGAA

RVRVRGSTGVAAAAGLHRYLRDFCGCHVAWSGSQLRLPRPLPAVPGELTE

ATPNRYRYYQNVCTQSYSFVWWDWARWEREIDWMALNGINLALAWSGQEA

IWQRVYLALGLTQAEINEFFTGPAFLAWGRMGNLHTWDGPLPPSWHIKQL

YLQHRVLDQMRSFGMTPVLPAFAGHVPEAVTRVFPQVNVTKMGSWGHFNC

SYSCSFLLAPEDPIFPIIGSLFLRELIKEFGTDHIYGADTFNEMQPPSSE

PSYLAAATTAVYEAMTAVDTEAVWLLQGWLFQHQPQFWGPAQIRAVLGAV

PRGRLLVLDLFAESQPVYTRTASFQGQPFIWCMLHNFGGNHGLFGALEAV

NGGPEAARLFPNSTMVGTGMAPEGISQNEVVYSLMAELGWRKDPVPDLAA

WVTSFAARRYGVSHPDAGAAWRLLLRSVYNCSGEACRGHNRSPLVRRPSL

QMNTSIWYNRSDVFEAWRLLLTSAPSLATSPAFRYDLLDLTRQAVQELVS

LYYEEARSAYLSKELASLLRAGGVLAYELLPALDEVLASDSRFLLGSWLE

-continued
QARAAAVSEAEADFYEQNSRYQLTLWGPEGNILDYANKQLAGLVANYYTP

RWRLFLEALVDSVAQGIPFQQHQFDKNVFQLEQAFVLSKQRYPSQPRGDT

VDLAKKIFLKYYPRWVAGSWGAPGGGGAAAAAGGGGGAPGGGGAAAA

AGGGGGGAPGGGGAAAAAGGGGGAP<ins>DGGFCEVCKKLVGYLDRNLEKNS</ins>

<ins>TKQEILAALEKGCSFLPDPYQKQCDQFVAEYEPVLIEILVEVMDPSFVCL</ins>

<ins>KIGACPSAHKPLLGTEKCIWGPSYWCQNTETAAQCNAVEHCKRHVWN</ins>

Human Naglu—in italics
GAG3 Linker—in bold
SapDC—underlined

Naglu-IGFII:
(SEQ ID NO: 25)
DEAREAAAVRALVARLLGPGPAADFSVSVERALAAKPGLDTYSLGGGGA

ARVRVRGSTGVAAAAGLHRYLRDFCGCHVAWSGSQLRLPRPLPAVPGEL

TEATPNRYRYYQNVCTQSYSFVWWDWARWEREIDWMALNGINLALAWSG

QEAIWQRVYLALGLTQAEINEFFTGPAFLAWGRMGNLHTWDGPLPPSWH

IKQLYLQHRVLDQMRSFGMTPVLPAFAGHVPEAVTRVFPQVNVTKMGSW

GHFNCSYSCSFLLAPEDPIFPIIGSLFLRELIKEFGTDHIYGADTFNEM

QPPSSEPSYLAAATTAVYEAMTAVDTEAVWLLQGWLFQHQPQFWGPAQI

RAVLGAVPRGRLLVLDLFAESQPVYTRTASFQGQPFIWCMLHNFGGNHG

LFGALEAVNGGPEAARLFPNSTMVGTGMAPEGISQNEVVYSLMAELGWR

KDPVPDLAAWVTSFAARRYGVSHPDAGAAWRLLLRSVYNCSGEACRGHN

RSPLVRRPSLQMNTSIWYNRSDVFEAWRLLLTSAPSLATSPAFRYDLLD

LTRQAVQELVSLYYEEARSAYLSKELASLLRAGGVLAYELLPALDEVLA

-continued
SDSRFLLGSWLEQARAAAVSEAEADFYEQNSRYQLTLWGPEGNILDYAN

KQLAGLVANYYTPRWRLFLEALVDSVAQGIPFQQHQFDKNVFQLEQAFV

LSKQRYPSQPRGDTVDLAKKIFLKYYPRWVAGSWGAPGGGGAAAAGG

GGGGAPGGGGAAAAAGGGGGAPGGGGAAAAAGGGGGAP<ins>LCGGELV</ins>

<ins>DTLQFVCGDRGFYFSRPASRVSRRSRGIVEECCFRSCDLALLETYCATP</ins>

<ins>AKSE</ins>

HumanNaglu—in italics
GAG3 Linker—in bold
IGFII—underlined

Activity Assay

Figure 2:
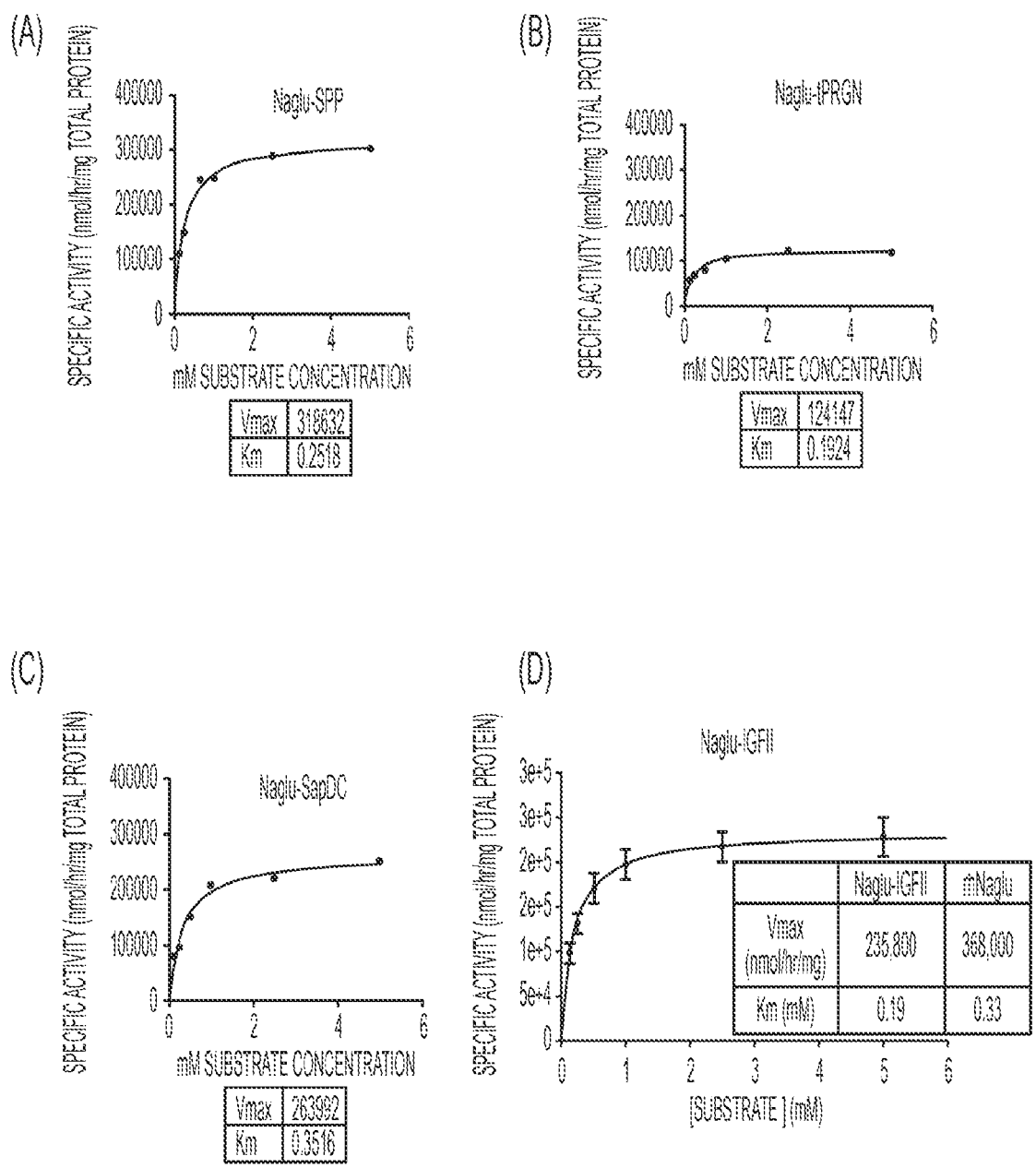
FIG. 2 shows enzyme kinetics ($V_{max}$ (nmol/hr/mg) and $K_m$ (mM)) of each of the four Naglu fusion proteins Naglu-SPP (A), Naglu-tPRGN (B), Naglu-SapDC (C), and Naglu-IGFII (D).

Following purification, each fusion protein was evaluated for proper function, by examining its specific activity and enzyme kinetics using a well-defined method using a cleavable fluorescent substrate. Each of the fusion proteins Naglu-SPP, Naglu-tPRGN, Naglu-SapDC, and Naglu-IGFII demonstrated specificity for the Naglu substrate with a Michaelis constant ($K_m$) in the range of 0.18-0.35 nM and a specific activity $V_{max}$ value in the range of 124,147-318,632 nmol/hr/mg (FIG. 2). All the fusion proteins tested exhibited $K_m$ and $V_{max}$ values similar to the corresponding values of rhNaglu (compare tables in FIGS. A-C with table in FIG. D).

Example 2: SORT1 Binding Studies

Studies were also carried out to determine the binding properties of Naglu-SPP and evaluate its specificity for SORT1 by surface plasmone resonance (SPR), a commonly used standard technique. Briefly, anti-His mAb (capturing molecule) was diluted in immobilization buffer and bound on the dextran surface of a SPR sensor chip housed in a microfluidic system. Next, a solution containing recombinant 6×Histidine tagged human SORT1 (ligand) was injected into the microflow system and run over the surface-bound anti-His mAbs to form a "capture complex." A solution containing purified Naglu-SPP protein (analyte) was then injected into the device. As the solution moved over the SPR sensor chip, the analyte bound to the capture complex and an increase in SPR signal (expressed in response units, RU) was observed. Finally, a solution without analyte was injected into the microfluidic device to detach bound SORT1 from the capture complex, resulting in a decrease in SPR signal. The detailed experimental conditions are described in Table 6 below.

TABLE 6

Experimental Design For Exemplary Surface Plasmone Resonance Assay

| Capturing Molecule | Ligand | Analyte | Analyte Conc. | Flow Rate | Association Time | Dissociation Time |
| --- | --- | --- | --- | --- | --- | --- |
| Anti-His mAB | SORT1-6xHis | Naglu-SPP | 0 nM<br>0.625 nM<br>1.25 nM<br>2.5 nM<br>5 nM<br>10 nM<br>20 nM | 30 µl/min | 300 sec | 300 sec |

Figure 3A:
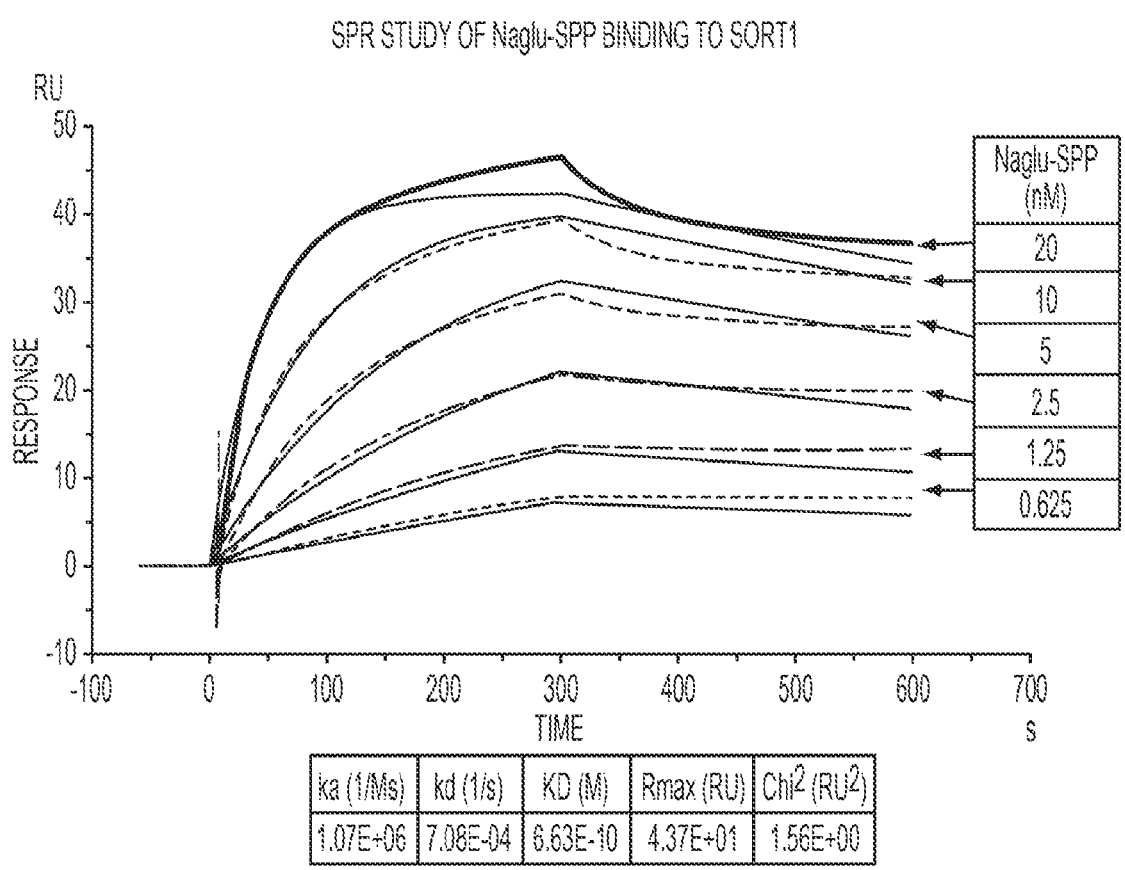
FIG. 3A shows binding of Naglu-SPP to SORT1 over a range of Naglu-SPP concentrations, as determined by surface plasmone resonance (SPR) analysis.

Naglu-SPP showed strong binding to SORT1 at all concentrations tested (0 to 20 nM), with an average association constant ($K_a$ [1/Ms]) of approximately $1.1 \times 10^6$, a dissociation constant ($K_d$ [1/s]) of approximately $7.1 \times 10^{-4}$, and an average equilibrium dissociation constant ($K^D$[M]) of approximately $6.6 \times 10^{-10}$ (FIG. 3A).

To evaluate the specificity of Naglu-SPP's binding to SORT1, the above-described binding reaction was conducted in the presence of purified human Neurotensin (20 µM). Neurotensin is a known ligand for SORT1 that can be used to competitively inhibit binding of a number of other SORT1 ligands. The detailed experimental conditions are described in Table 7 below.

TABLE 7

Experimental Design For Exemplary Surface Plasmone Resonance Assay

| Capturing Molecule | Ligand | Analyte | Analyte (Conc.) | Neurotensin (Conc.) | Flow Rate | Assoc. Time | Dissoc. Time |
|---|---|---|---|---|---|---|---|
| Anti-His mAB | SORT1-6xHis | Naglu-SPP | 20.0 nM | 0.0 μM | 30 μl/min | 300 sec | 300 sec |
| | | | 0.0 nM | 20 μM | | | |
| | | | 0.625 nM | 20 μM | | | |
| | | | 1.25 nM | 20 μM | | | |
| | | | 2.5 nM | 20 μM | | | |
| | | | 5 nM | 20 μM | | | |
| | | | 10 nM | 20 μM | | | |
| | | | 20 nM | 20 μM | | | |

Figure 3B:
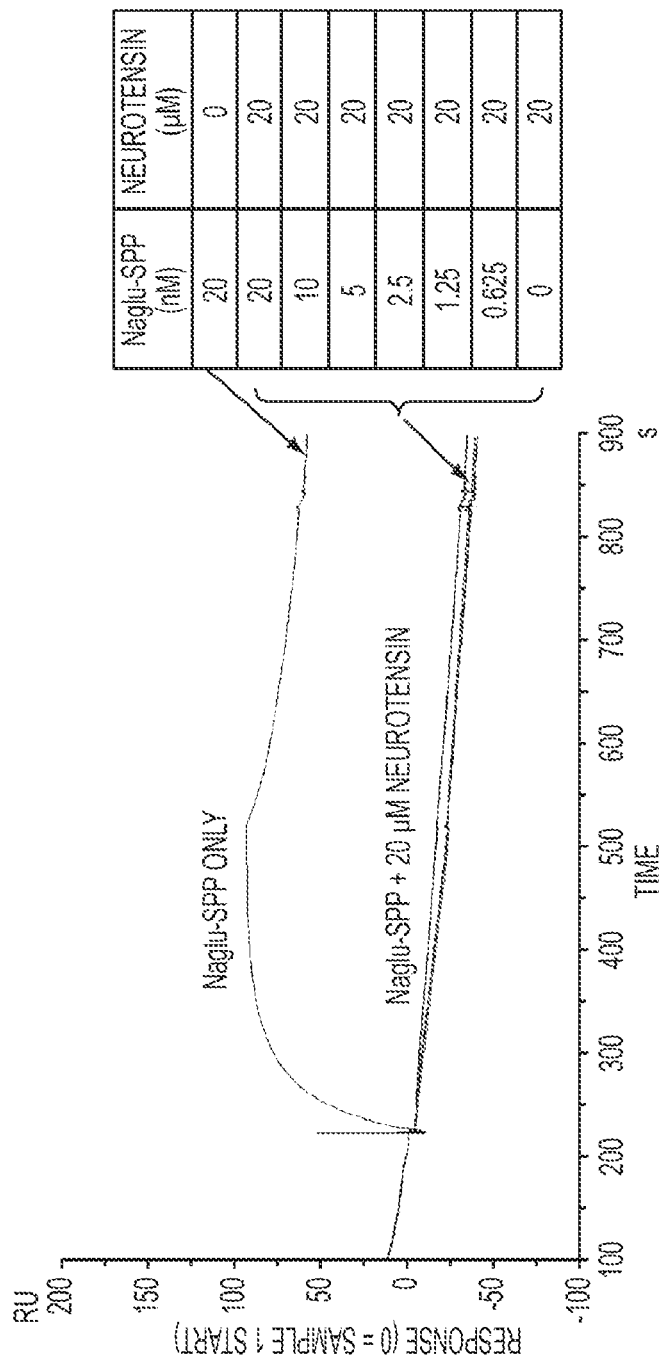
FIG. 3B shows binding of Naglu-SPP to SORT1 in the absence or presence of the competitive inhibitor Neurotensin, as determined by surface plasmone resonance (SPR) analysis.

The data show that addition of 20 μM Neuotensin to the above described SPR binding assay completely blocks binding of Naglu-SPP to SORT1 (FIG. 3B). This effect was observed at all Naglu-SPP concentrations tested (0 to 20 nM). The data also indicate that binding of Naglu-SPP to SORT1 is specific and mediated by the fusion protein's SPP peptide.

The above analysis was further extended by evaluating the competitive inhibition of a constant concentration of Naglu-SPP (20 nM) by varying concentrations of Neurotensin (0 to 1500 nM). The experimental conditions used for this assay are described in Table 8 below.

TABLE 8

Experimental Design For Exemplary Surface Plasmone Resonance Assay

| Capturing Molecule | Ligand | Analyte | Analyte (Conc.) | Neurotensin (Conc.) | Flow Rate | Assoc. Time | Dissoc. Time |
|---|---|---|---|---|---|---|---|
| Anti-His mAB | Sortilin-6xHis | Naglu-SPP | 20 nM | 0.0 nM | 30 μl/min | 300 sec | 300 sec |
| | | | 20 nM | 25 nM | | | |
| | | | 20 nM | 50 nM | | | |
| | | | 20 nM | 100 nM | | | |
| | | | 20 nM | 200 nM | | | |
| | | | 20 nM | 400 nM | | | |
| | | | 20 nM | 600 nM | | | |
| | | | 20 nM | 1.0 μM | | | |
| | | | 20 nM | 1.5 μM | | | |

Figure 4A:
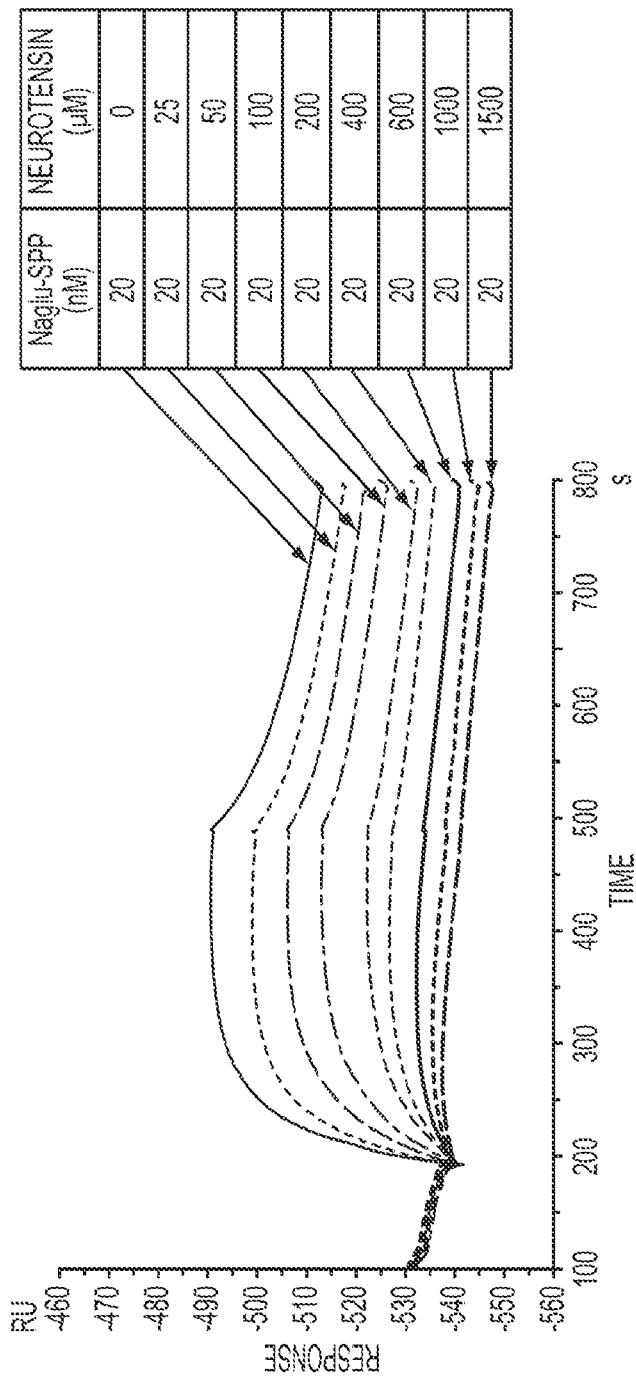
FIG. 4A shows inhibition of Naglu-SPP binding to SORT1 by various concentrations of Neurotensin, as determined by surface plasmone resonance (SPR) analysis.
Figure 4B:
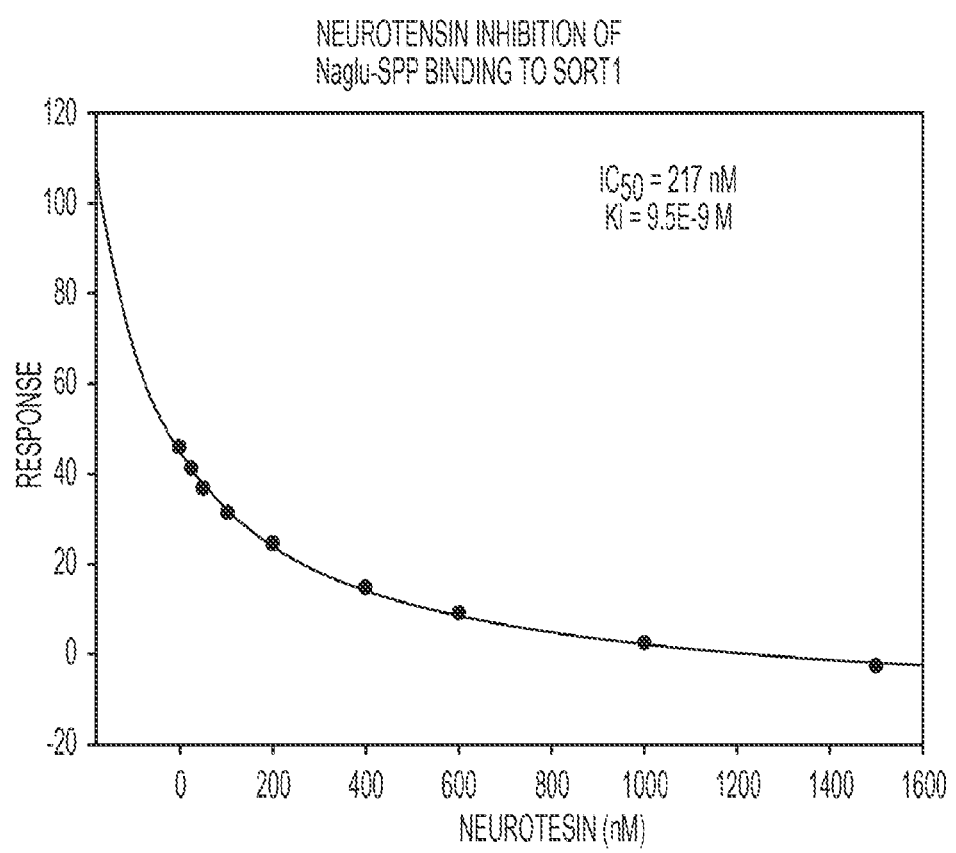
FIG. 4B shows a Neurotensin inhibition curve based on the data presented in FIG. 4A.

The data show that Neurotensin inhibits Naglu-SPP binding to SORT1 in a dose dependent manner across the entire range of Neurotensin concentrations tested; 1.5 μM Neurotensin, the highest concentration tested, leads to a complete loss of Naglu-SPP binding to SORT1 (FIG. 4A). Analysis of the data revealed that Neurotensin competitively inhibits binding of Naglu-SPP to SORT1 with an $IC_{50}$=217 nM and a $K_i$ value of $9.5 \times 10^{-9}$ (FIG. 4B).

Taken together, the inventors' findings clearly demonstrate that Naglu-SPP effectively binds to SORT1 through interaction of its SPP peptide region. Furthermore, Naglu-SPP binding is selective for SORT1 and can be disrupted by a well-established competitive inhibitor of SORT1, i.e., Neurotensin. The specific binding of Naglu-SPP allows for the fusion protein's SORT1-mediated cellular entry and lysosomal targeting.

Example 3: In Vitro Studies

Cellular Uptake in Sortilin Overexpressing Cells

Figure 5:
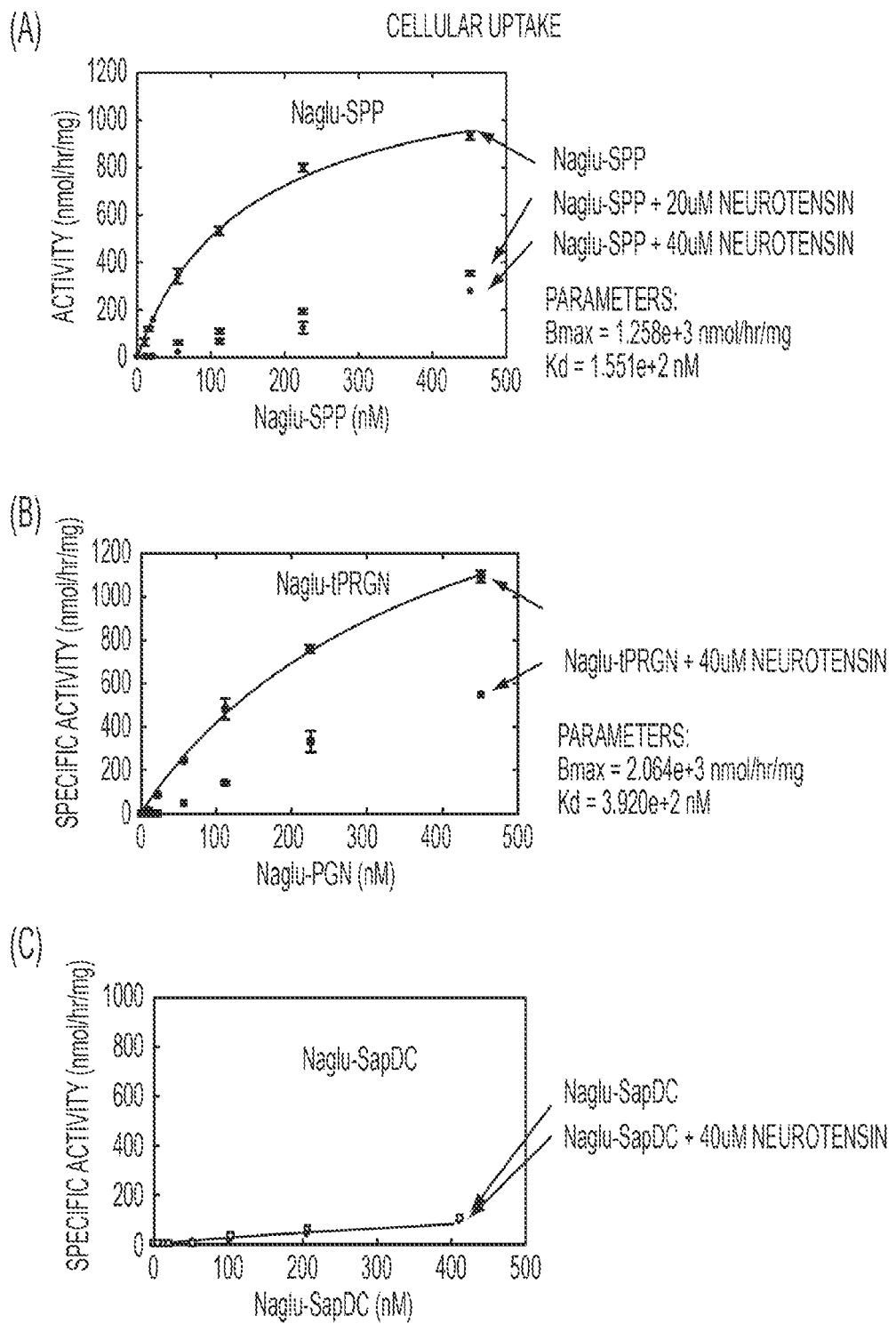
FIG. 5 shows binding and cellular uptake of Naglu-SPP (A), Naglu-tPRGN(B) and Naglu-SapDC fusion proteins (C) in the presence and absence of Neurotensin.

A study was performed to assess cellular uptake of the following Naglu fusion proteins: Naglu-SPP, Naglu-tPRGN and Naglu-SapDC. A cell line was established overexpressing SORT1, using standard technologies known in the art. SORT1 overexpressing cells were grown to confluence and then treated with a solution of recombinant Naglu-SPP, Naglu-tPRGN or Naglu-SapDC at various concentrations in the presence or absence of Neurotensin (FIG. 5). After a specified period of time, the supernatant was removed and the cells were washed repeatedly. Then, cells were lysed and each sample was assayed for Naglu enzyme activity. The data show that intracellular levels of Naglu activity increase following treatment of cells with Naglu-SPP and Naglu-tPRGN. This suggests that both Naglu-SPP and Naglu-tPRGN are effectively internalized. The data also indicate that cellular uptake occurs in a dose dependent fashion since the intracellular Naglu activity detected increased proportionally to the increasing amounts of Naglu-SPP and Naglu-tPRGN used for the binding/uptake assay (FIG. 5, panels A and B).

Naglu-SPP binds SORT1 with a $K_d$ of 155 nM and a $B_{max}$ of $1.26 \times 10^3$ nmol/hr/mg, and Naglu-tPRGN binds SORT1 with a $K_d$ of 392 nM and a $B_{max}$ of $2.06 \times 10^3$ nmol/hr/mg (FIG. 5, panels A and B).

The data also demonstrate that, different from treatment of cells with Naglu-SPP and Naglu-tPRGN, treatment of cells with Naglu-SapDC results in only a very limited increase in the level of intracellular Naglu activity, suggesting that Naglu-SapDC is not effectively internalized by cells (FIG. 5, panel C).

In stark contrast to the aforesaid, co-administration of Naglu-SPP and Naglu-tPRGN fusion proteins with Neurotensin (200 μM and 400 μM) results in a strongly reduced increase of intracellular accumulation of Naglu activity (FIG. 5, panels A and B). Neurotensin is a known ligand for SORT1 and can competitively inhibit binding of other ligands. The data indicate that Neurotensin is able to outcompete binding of Naglu-SPP and Naglu-tPRGN to SORT1, and thereby block internalization of these fusion proteins (FIG. 5, panel A and B). Given that Neurotensin binding is specific for SORT1, these findings further suggest that lysosomal targeting and entry of Naglu-SPP and Naglu-tPRGN is facilitated through a SORT1 mediated pathway.

Visualization of Lysosomal Targeting and Entry of Naglu-SPP

Figure 6A:
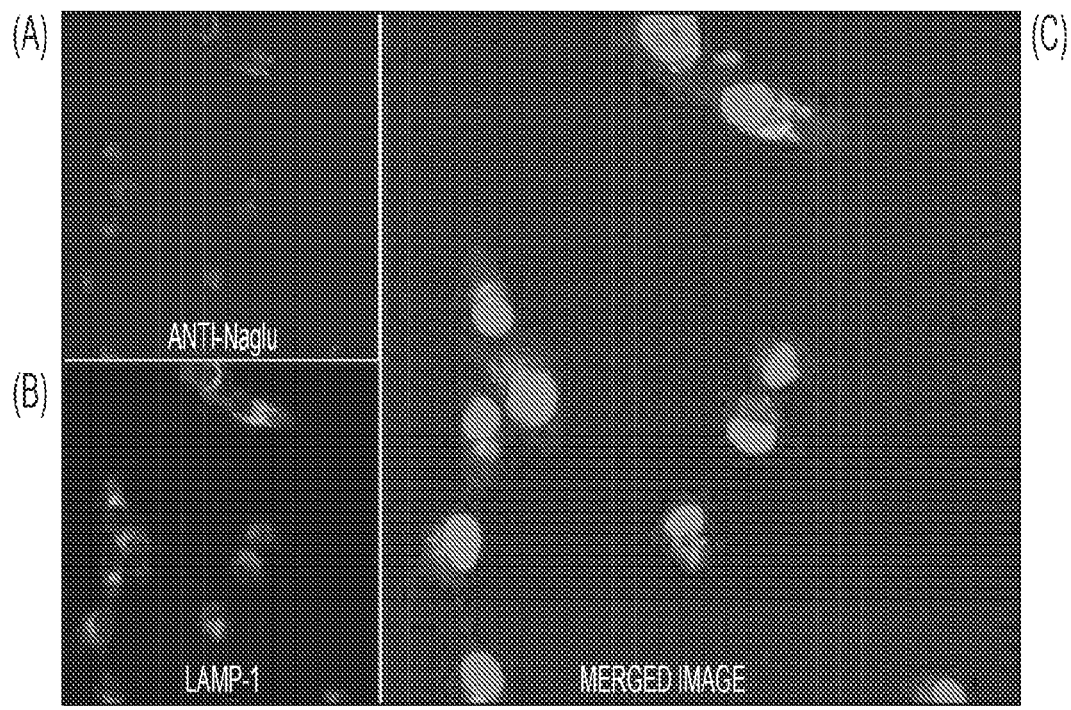
FIGS. 6A-B show the results of a confocal fluorescence microscopy study of cellular uptake of Naglu-SPP and its co-localization with lysosomes. Cells were treated with a vehicle control (6A) or Naglu-SPP (FIG. 6B). Intracellular localization of Naglu and its co-localization with the lysosomal marker Lamp-1 were determined by immunofluorescence using specific antibodies (Panels A-C). Cell nuclei (Panel C) were visualized using DAPI.
Figure 6B:
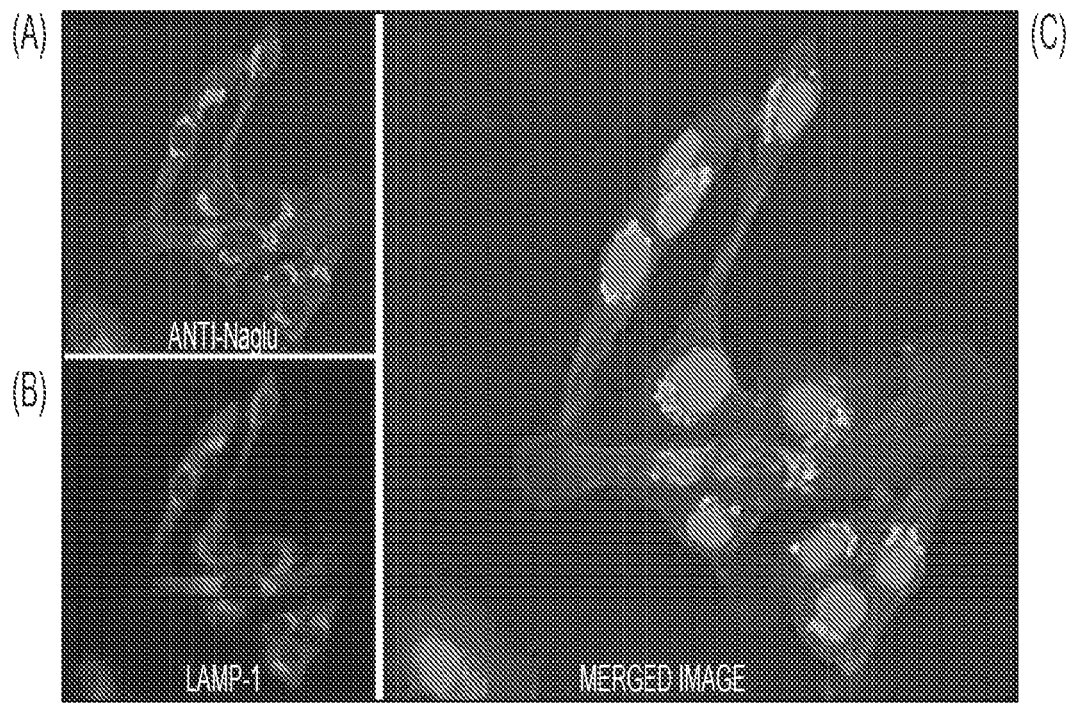

Studies were carried out using immunofluorescence microscopy to evaluate cellular entry and lysosomal targeting. For these studies, SORT overexpressing cells were treated with vehicle control or Naglu-SPP and then fixed and prepared for staining. Both vehicle control (FIG. 6A) and Naglu-SPP (FIG. 6B) treated cells were stained using antibodies specific for human Naglu and Lamp-1, a lysosome-specific protein biomarker. Contrary to the cells treated with the vehicle control (FIG. 6A), cells treated with Naglu-SPP showed a strong, Naglu-specific fluorescence signal (FIG. 6B, panel A). Small punctate regions of fluorescence were observed when cells were stained for Naglu, and this fluorescence was localized predominantly within lysosomal vesicles, as confirmed by co-localization with Lamp-1-derived immunofluorescence (FIG. 6B, panel C). Consistent with the findings above, these microscopy data further demonstrate that Naglu-SPP enters cells and is targeted to the lysosomal compartment.

Example 4: Biodistribution of Naglu Fusion Proteins Administered to Wild Type Rats Via Intrathecal Injection To evaluate biodistribution of the SORT1-binding Naglu fusion proteins, an in vivo study was conducted using wild-type rats subjected to intrathecal administration of vehicle control (PBS), rhNaglu, Naglu-IGFII, Naglu-SPP, Naglu-SapDC or Naglu-tPRGN. Details of the experimental design are provide in Table 9 below. Previous experiments had shown that Naglu-IGFII but not rhNaglu penetrates into brain tissue and is targeted to lysosomes after intrathecal injection. Accordingly, rhNaglu and Naglu-IGFII were utilized in this study as negative and positive controls, respectively.

TABLE 9

Experimental Design to Assay Intracellular Delivery

| Group | No. | Treatment | Dose (ug/animal) | Route | Sacrifice |
|---|---|---|---|---|---|
| A | 10 | Vehicle | N/A | Intrathecal | n = 5 at 4 hrs |
| B | 10 | rhNaglu | 385 | | n = 5 at 24 hrs post dose |
| C | 10 | Naglu-IGFII | 385 | | |
| D | 10 | Naglu-SPP | 385 | | |
| E | 10 | Naglu-SapDC | 385 | | |
| F | 10 | Naglu-tPRGN | 385 | | |

Intracellular Accumulation of Naglu Fusion Proteins

Figure 7A:
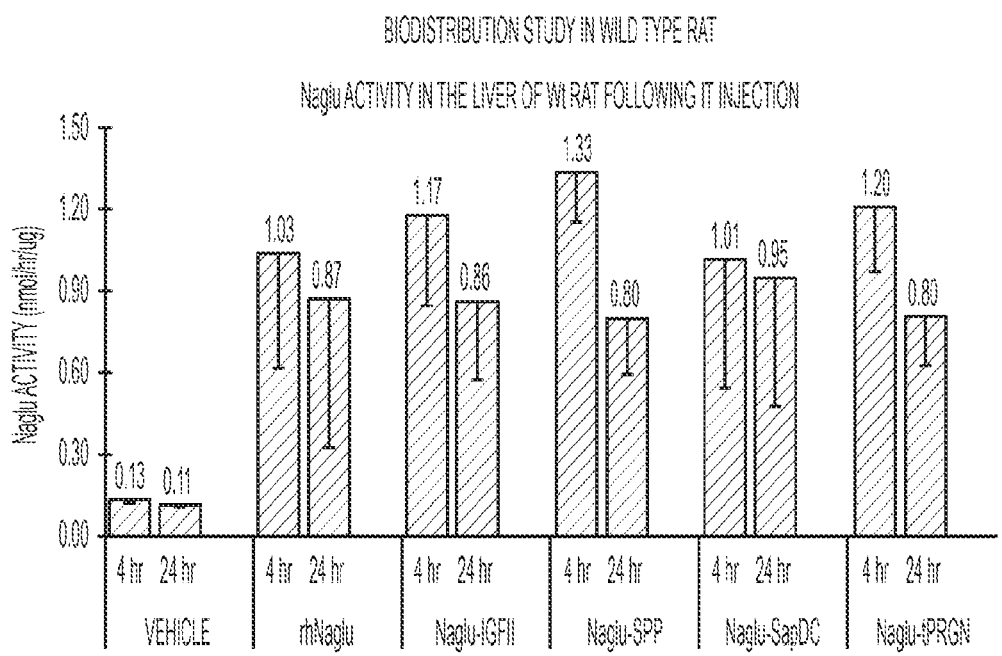
FIGS. 7A-B demonstrates in vivo Naglu enzyme activity in (A) liver and (B) brain following intrathecal delivery of vehicle control, non-fusion rhNaglu, Naglu-IGFII, Naglu-SPP, Naglu-SapDC or Naglu-tPRGN to wild-type rats in a biodistribution study.
Figure 7B:
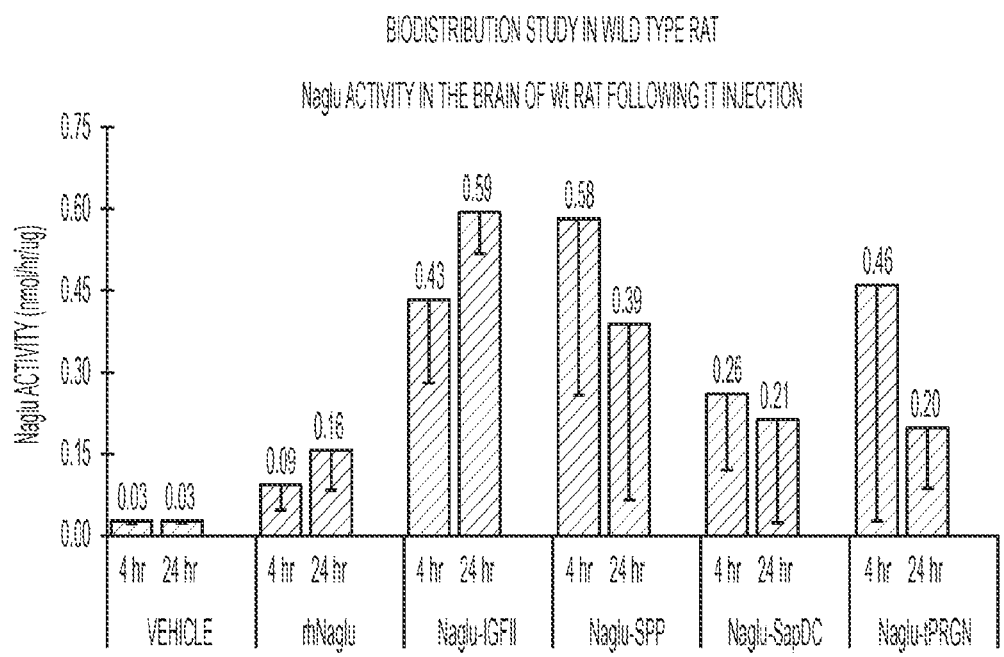

Rats were sacrificed either 4 or 24 hours post intrathecal administration of the respective fusion protein and total Naglu enzyme activity in the animals' liver and brain tissue was determined using a well-established enzyme activity assay (FIGS. 7A and B). Briefly, brain and liver tissue homogenates were prepared and incubated in the presence of a Naglu specific substrate, i.e., methylumbelliferyl-N-acetyl-α-D-glucosainide; accumulation of cleavage product was then measured by examining fluorescence intensity at 360/460 nm (excitation/emission) using a fluorescent plate reader.

The data show that intrathecal administration of the described Naglu fusion proteins leads to an elevated level of Naglu enzyme activity in the liver of test animals. By contrast, only administration of Naglu-IGFII, Naglu-SPP, Naglu-SapDC and Naglu-tPGRN resulted in markedly elevated levels of Naglu enzyme activity in the brain, with the highest activity being observed in rats treated with Naglu-IGFII or Naglu-SPP.

Together, our data show that the SPP peptide (SEQ ID NO: 4), just like the IGFII peptide (SEQ ID NO: 21), facilitates CI-MPR-independent cellular uptake of fusion proteins into the brain in vivo. And the data also indicate that fusion enzymes carrying the SPP peptide are fully functional.

Biodistribution of Naglu Fusion Proteins in the Brain Tissue by Immunohistochemistry (IHC)

Rats were sacrificed either 4 or 24 hours post intrathecal administration of the respective fusion protein. Brain tissue samples were collected, fixed in 10% NBF and processed for paraffin embedding. 5 μm paraffin sections from each tissue assayed were subjected to immunostaining using an anti-human Naglu antibody.

Figure 8A:
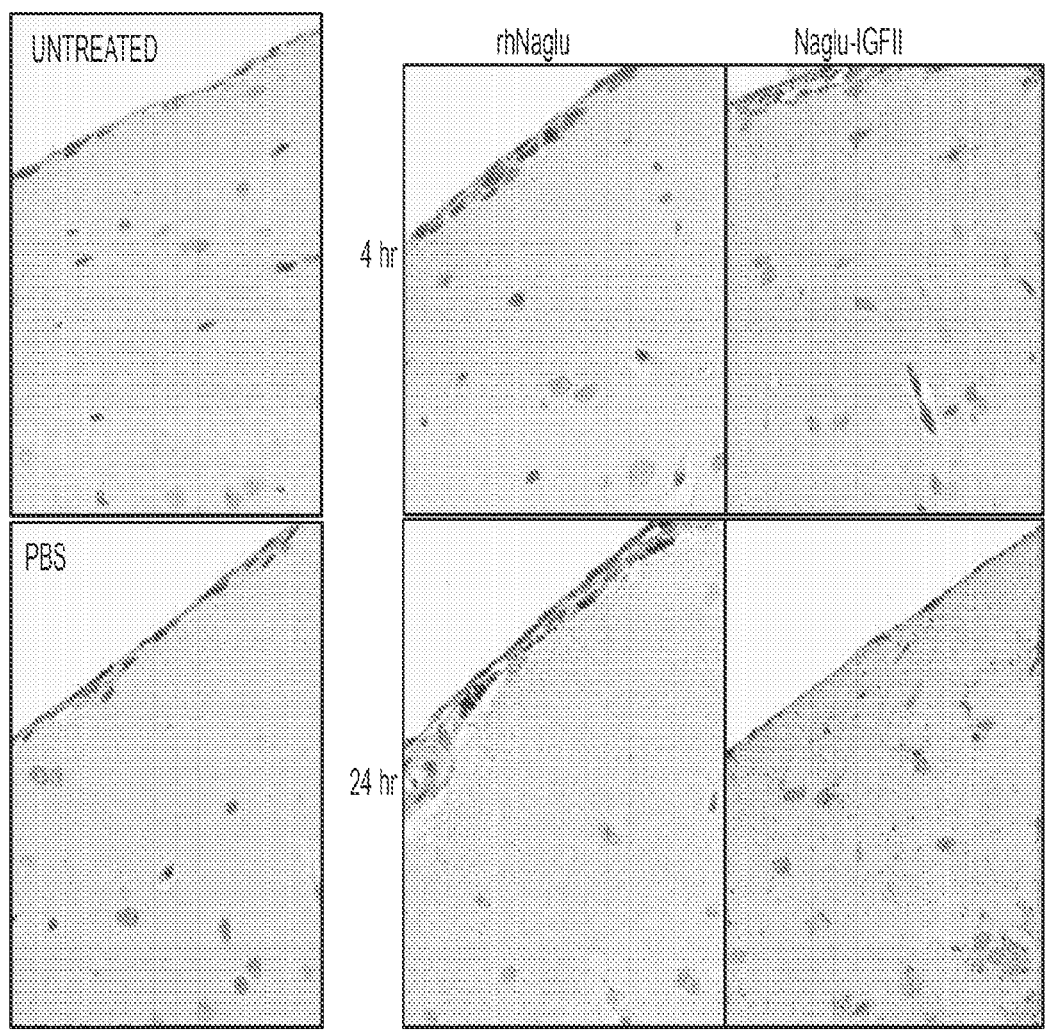
FIG. 8A-H shows immunohistochemical staining of Naglu protein in wild-type rat cerebral cortex tissue at 4 hours and 24 hours post intrathecal delivery of (A) vehicle control, non-fusion rhNaglu and Naglu-IGFII fusion protein, and (B) Naglu-SPP, Naglu-SapDC and Naglu-tPRGN fusion proteins.

Cerebral cortex tissue of vehicle control (PBS) treated rats showed little to no background Naglu signal at 4 and 24 hours post injection, confirming the specificity of the human anti-Naglu antibody used (FIGS. 8A and C). Similarly, cerebral cortex tissue of rats treated with recombinant human Naglu (rhNaglu) resulted in only minor Naglu signal, and most of the staining occurred on the meninges and the interstitial area of the brain, not in the neurons and glia cells. This result indicates that rhNaglu is not properly internalization into brain tissue (FIG. 8A, D).

Figure 8G:
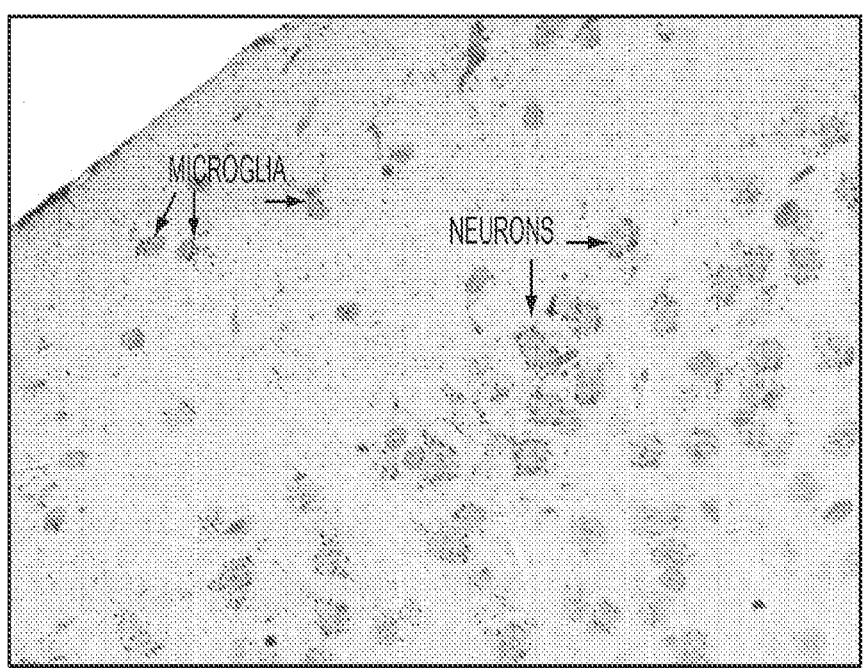
Figure 9A:
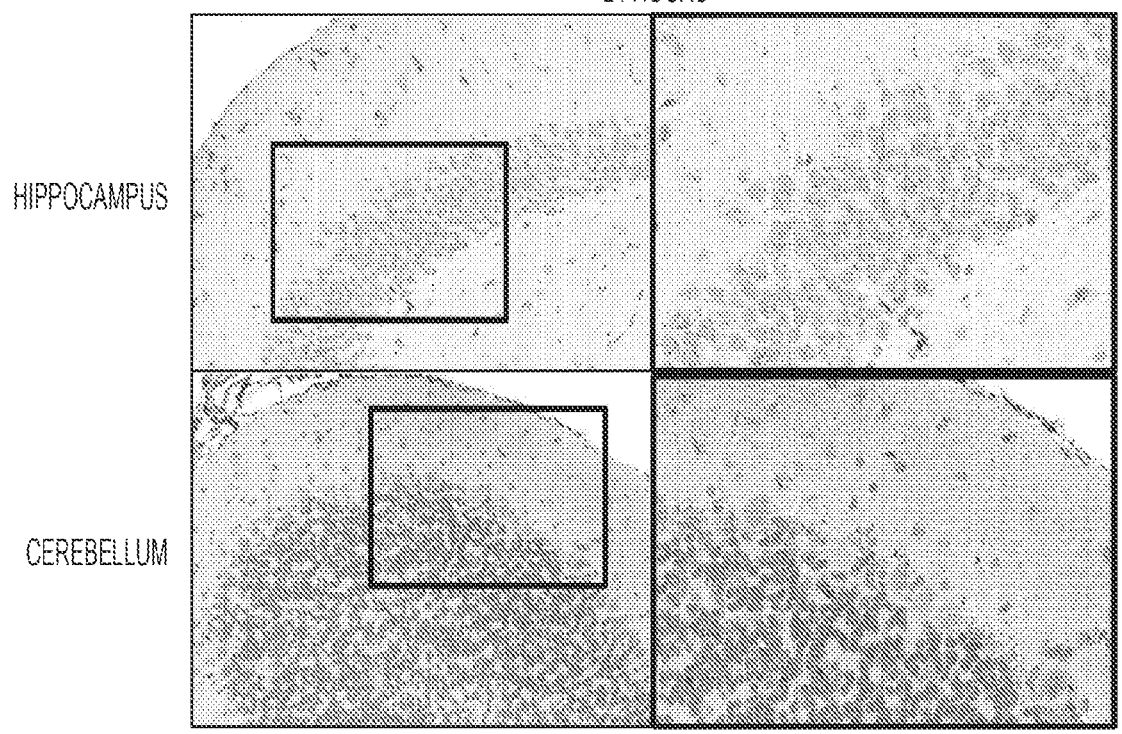
FIGS. 9A-B show immunohistochemical staining of Naglu protein in wild-type rat hippocampus and cerebellum tissues at 24 hours post intrathecal injection of (A) Naglu-IGFII or (B) Naglu-SPP.

In contrast, intrathecal administration of Naglu-IGFII resulted in positive staining in brain parenchyma of rats sacrificed 4 and 24 hours post treatment (FIGS. 8A, G). As is particularly evident in FIG. 8G, Naglu staining was distributed in a punctate pattern in neuron and glia cells, which is a pattern consistent with intracellular, lysosomal delivery. Immunohistochemical analysis also revealed strong Naglu signal in the cerebellum and the hippocampal region of the brain (FIG. 9A).

Figure 8B:
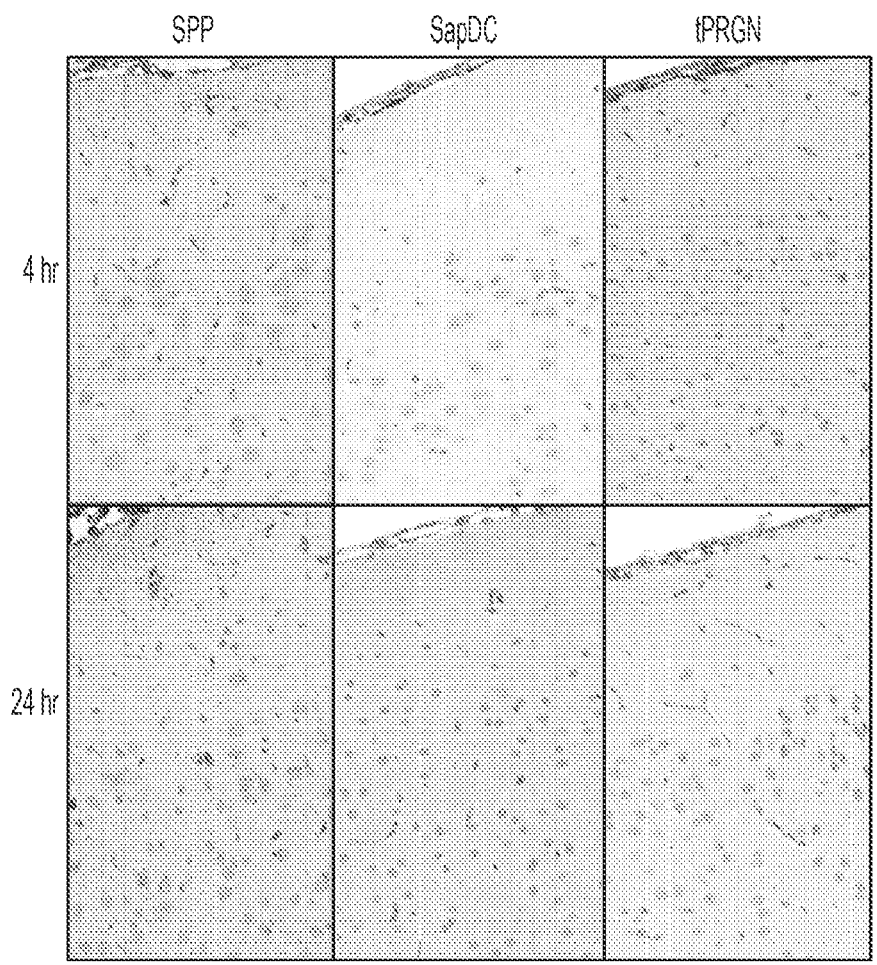
Figure 8C:
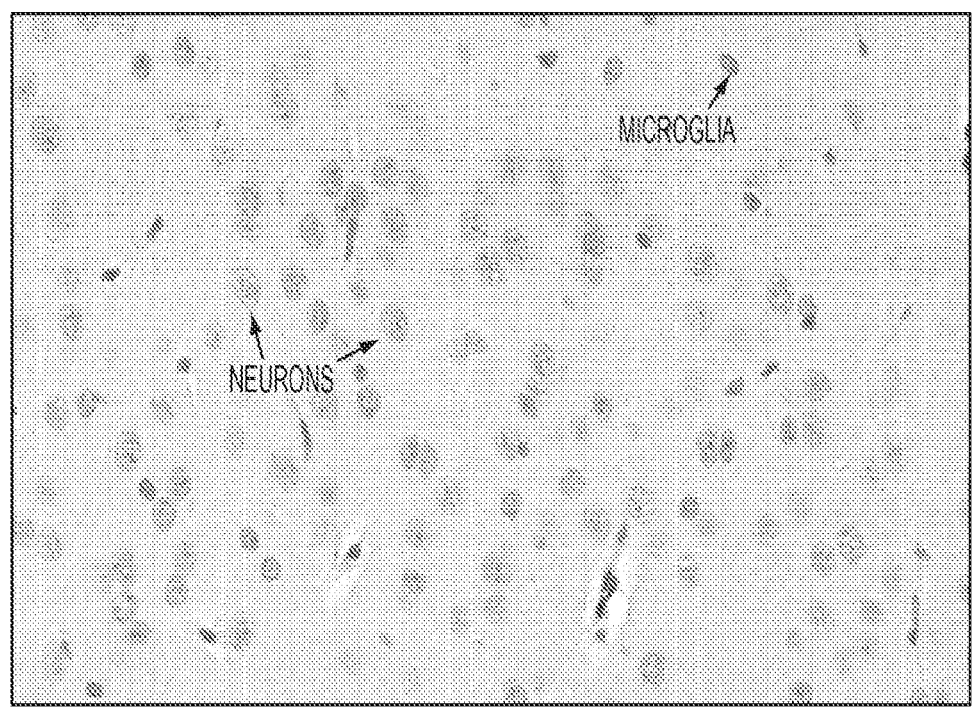
Figure 8D:
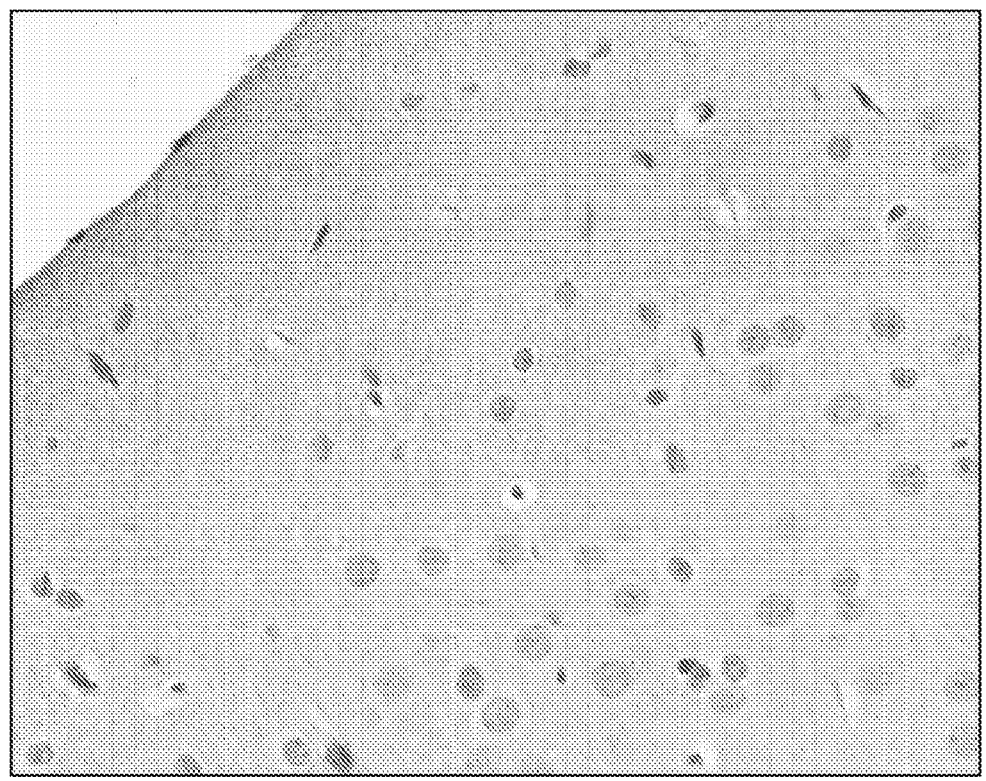
Figure 8E:
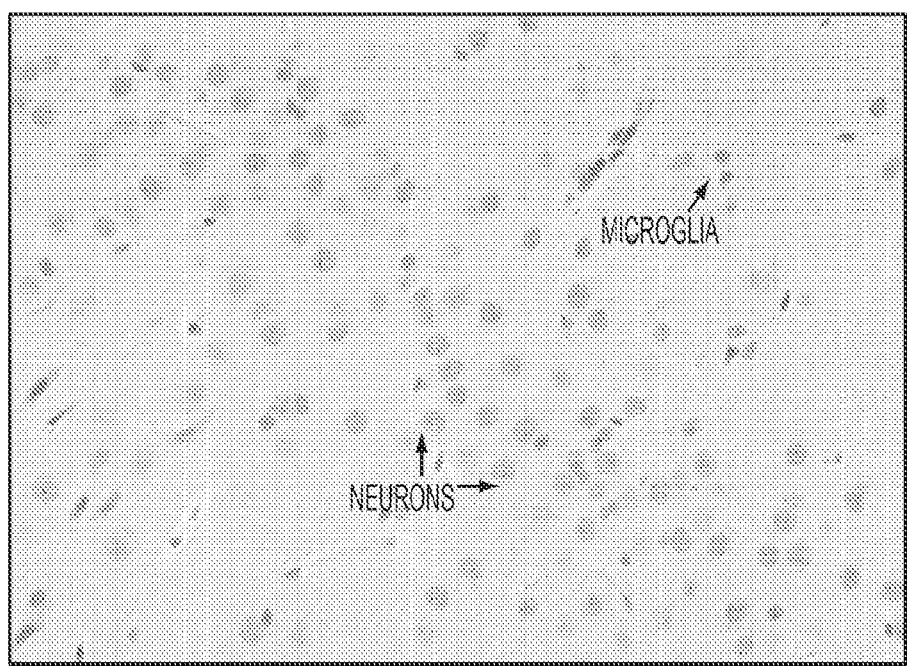
Figure 8F:
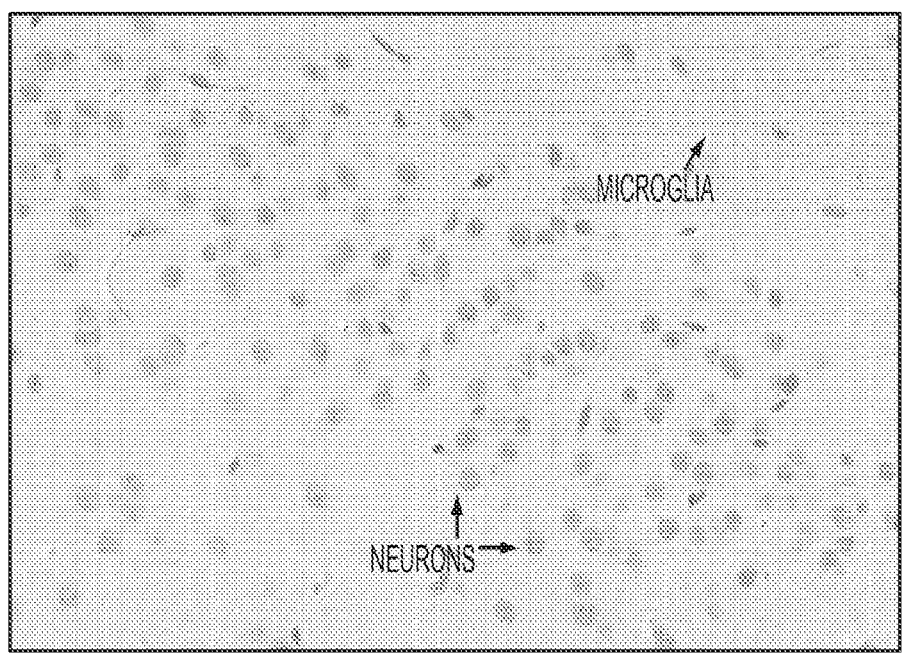
Figure 8H:
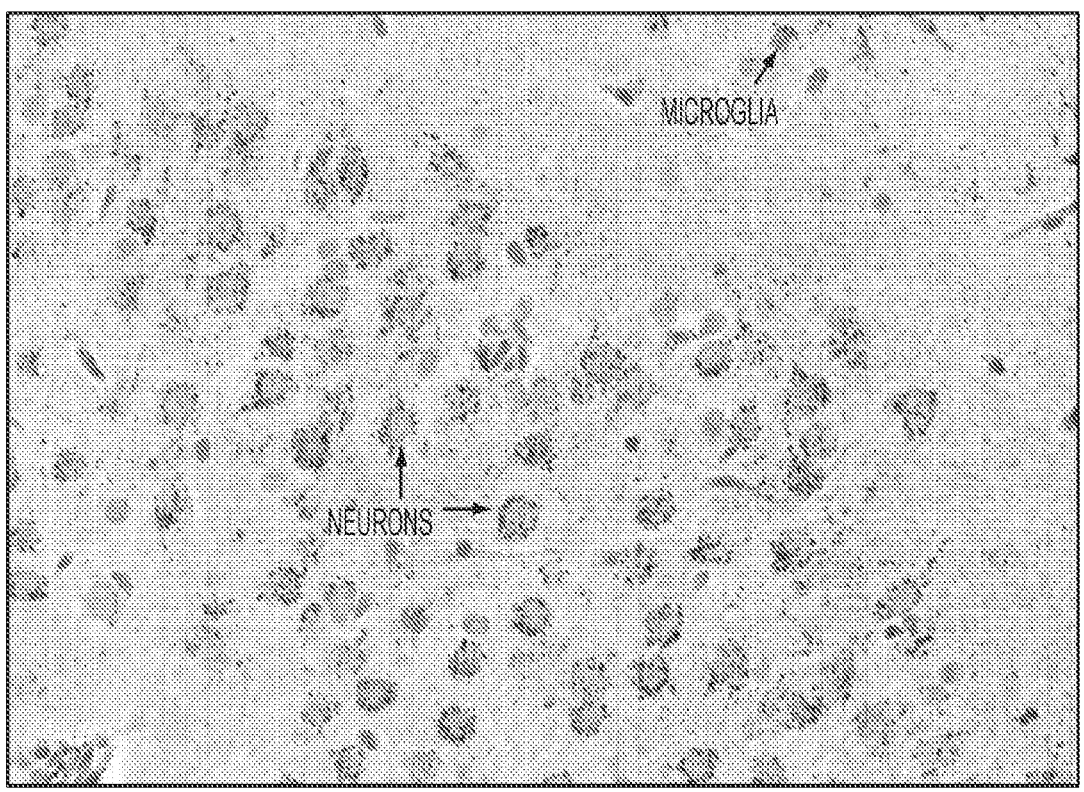
Figure 9B:
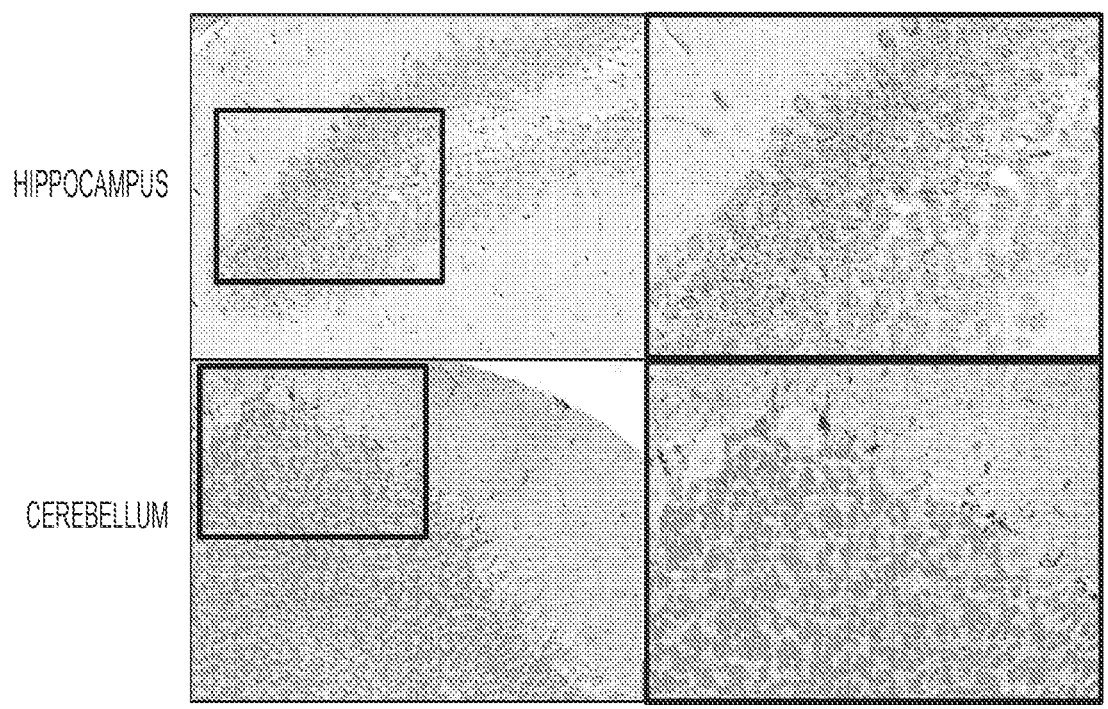

Similarly, intrathecal administration of Naglu-SPP resulted in positive staining in brain parenchyma of rats sacrificed 4 and 24 hours post treatment (FIG. 8B). As is particularly evident in FIG. 8H, Naglu staining was distributed in a punctate pattern in neuron and glia cells, which is a pattern consistent with intracellular, lysosomal delivery. Immunohistochemical analysis also revealed strong Naglu signal in the cerebellum and the hippocampal region of brain (FIG. 9B).

Notably, little to no Naglu signal was observed in brain tissue from rats that had received intrathecal delivery of Naglu-SapDC and Naglu-tPRGN (FIGS. 8B, E and F). These findings suggest, that while Naglu-SPP, Naglu-SapDC and Naglu-tPRGN are able to bind to SORT1 in vitro (FIG. 5), only Naglu-SPP and the positive control Naglu-IGFII are targeted to lysosomes of neurons and glia cells in vivo. Thus, among the fusion proteins tested, only Naglu-SPP represents a viable option for treatment of lysosomal storage diseases, including San B, in human patients.

Example 5: In Vivo Activity and Treatment Efficacy of Naglu-SPP

To evaluate the in vivo activity of Naglu-SPP and its efficacy as a therapeutic for the treatment of lysosomal storage diseases, particularly San B, Naglu-SPP was administered to Naglu KO mice via intrathecal injection. Intrathecal administration of Naglu-IGFII served as a positive control. The experimental conditions used for this assay are described in Tables 10 and 11 below.

TABLE 10

Experimental Design to Assay Efficacy of Naglu-SPP

| Group | No. | Treatment | Dose (mg/kg brain) | Route | Frequency | Sacrifice |
|---|---|---|---|---|---|---|
| A | 3 | Vehicle | N/A | Intrathecal | 2x Weekly | 24 hrs post final dose |
| B | 6 | Naglu-SPP | 520 | | | |
| C | 3 | Vehicle | N/A | Intrathecal | 3x Weekly | 24 hrs post final dose |
| D | 6 | Naglu-SPP | 520 | | | |

TABLE 11

Experimental Design to Assay Efficacy of Naglu-IGFII

| Group | No. | Treatment | Dose (mg/kg brain) | Route | Frequency | Sacrifice |
|---|---|---|---|---|---|---|
| A | 2 | Vehicle | N/A | Intrathecal | Single injection | 24 hrs post final dose |
| B | 5 | Naglu-IGFII | 520 | | | |
| C | 2 | Vehicle | N/A | Intrathecal | 2x weekly | 24 hrs post final dose |
| D | 5 | Naglu-IGFII | 520 | | | |
| E | 2 | Vehicle | N/A | Intrathecal | 3x wekly | 24 hrs post final dose |
| F | 5 | Naglu-IGFII | 520 | | | |

Figure 10A:
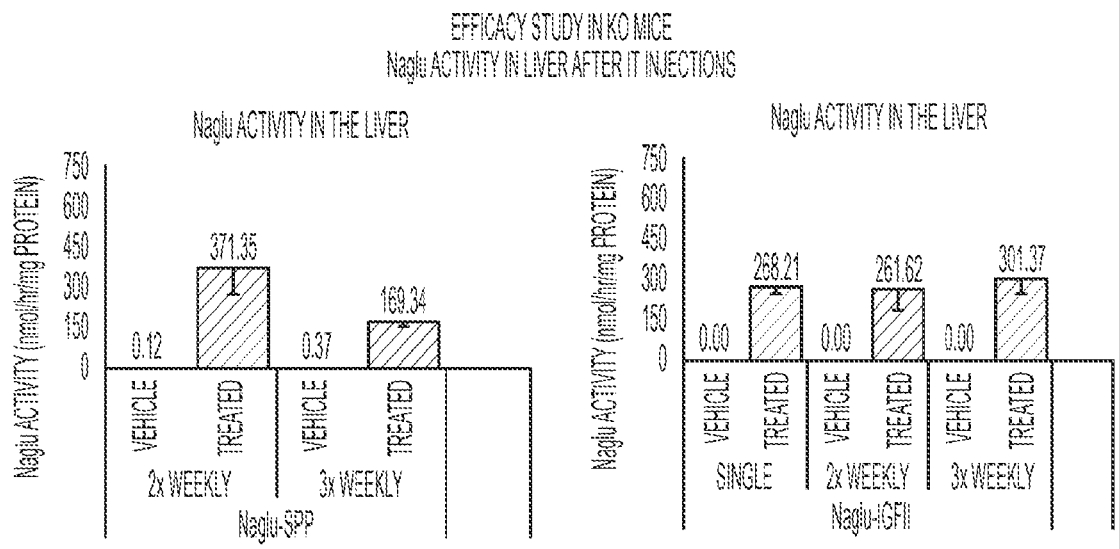
FIGS. 10A-B show in vivo Naglu enzyme activity in the (A) liver and (B) brain of Naglu knock-out mice following intrathecal delivery of vehicle control, Naglu-SPP or Naglu-IGFII.
Figure 10B:
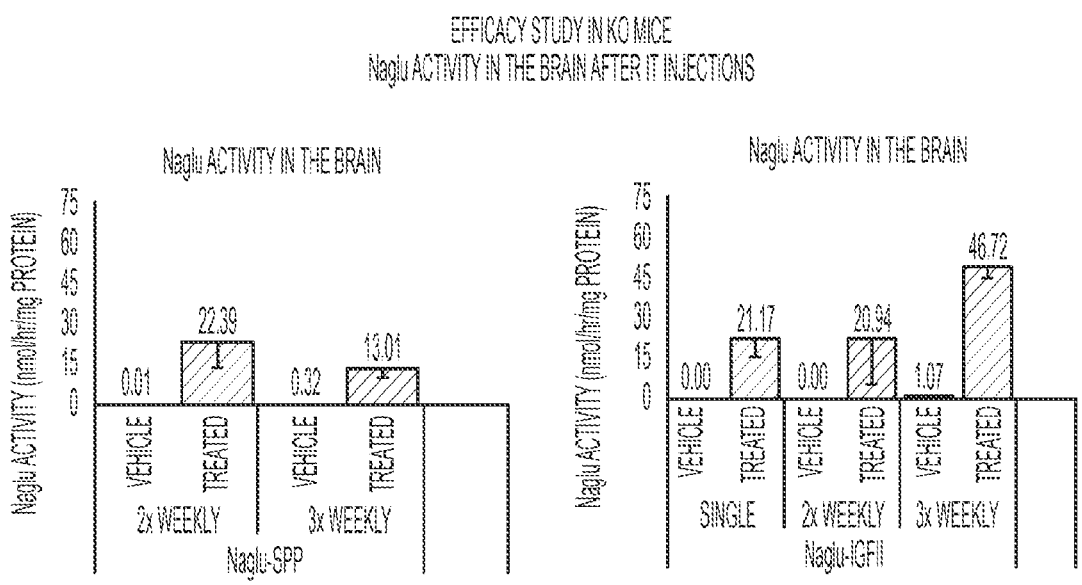

Intracellular Accumulation of Naglu Activity and the Reduction of the Natural Substrate after Intrathecal Treatment of Naglu-SPP and Naglu-IGFII 24 hours after intrathecal administration of each respective fusion protein, Naglu KO mice were sacrificed and Naglu enzyme activity in various tissues was assayed. Total Naglu activity was evaluated using a well-established enzyme activity assay. Briefly, tissue homogenate was incubated in the presence of the Naglu specific substrate methylumbelliferyl-N-acetyl-α-D-glucosainide, and accumulation of cleavage product was measured by examining fluorescence intensity at 360/460 nm (excitation/emission) using a fluorescent plate reader. The data demonstrate that treatment with Naglu-SPP and Naglu-IGFII results in a dramatic increase of Naglu activity in both liver and brain tissue, when compared to vehicle control (FIGS. 10A and B). This increase in enzyme activity was observed over the duration of the 3 week treatment period. It suggests that Naglu-SPP and Naglug-IGFII are properly internalized into cells and targeted to lysosomes, while, at the same time, maintaining enzyme activity.

Figure 11A:
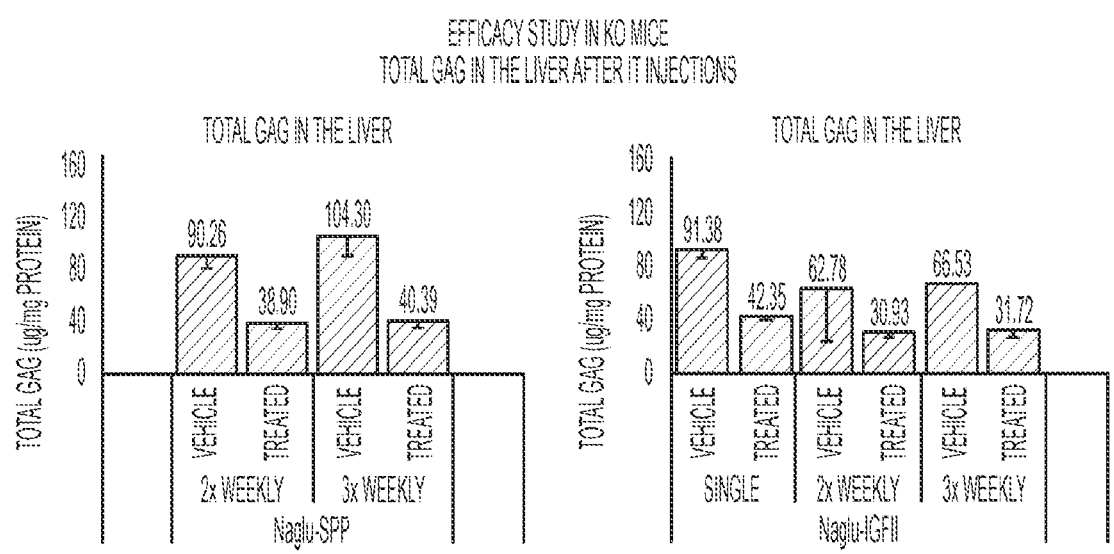
FIGS. 11A-B show in vivo levels of total glucosaminoglycan (GAG) in the (A) liver and (B) brain of Naglu knock-out mice following intrathecal delivery of vehicle control, Naglu-SPP or Naglu-IGFII. Total GAG levels in liver tissue were assayed in tissue homogentate; total GAG levels in brain tissue were assayed following GAG extraction.
Figure 11B:
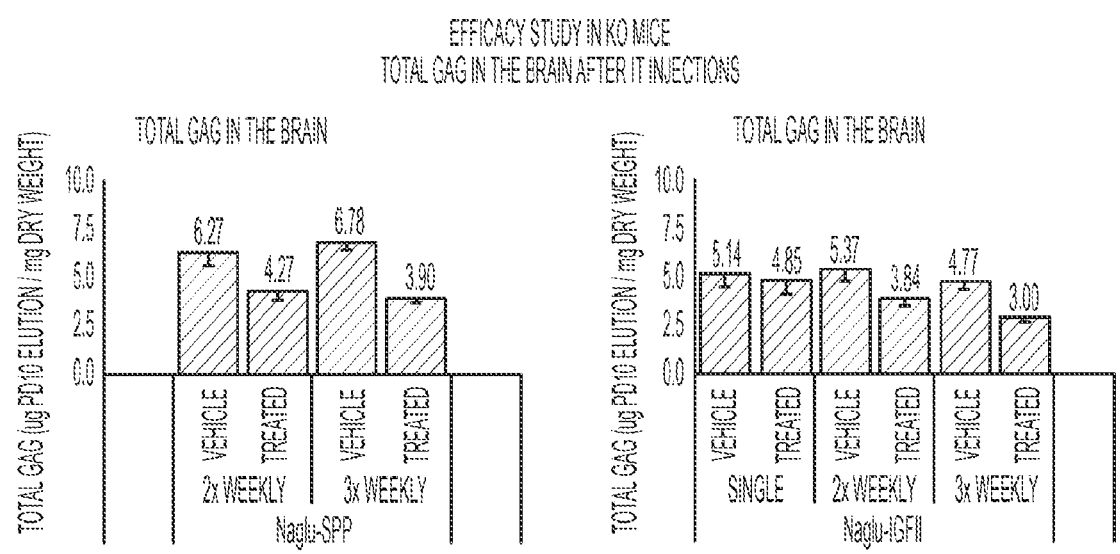

The activity of Naglu-SPP and Naglu-IGFII in vivo was also evaluated by examining the intracellular accumulation of natural substrates of Naglu in treated mice. One such assay was designed to evaluate the total concentration of glycosaminoglycan (GAG) in liver (FIG. 11A) and brain (FIG. 11B) tissue of treated mice in accordance with de Jong et al. (Clin Chem 38(6):803-807, 1992). Briefly, liver tissue was homogenized and total GAG quantified using dimethylmethylene blue. Brain tissue was homogenized and then incubated with pronase and benzonase to break down protein and nucleic acid. Total GAG was then extracted by passing the brain homogenate through a DEAE column. The eluate was further buffer exchanged through a desalting column, and the total GAG content was quantified using dimethylmethylene blue. As shown in FIGS. 11A and B, intrathecal delivery of Naglu-SPP and Naglu-IGFII resulted in a significant reduction in total GAG concentration within liver and brain tissue of Naglu KO mice, when compared to vehicle control. The reduction of total GAG amount in brain tissue was significant in the 2x weekly as well as the 3x weekly treatment groups.

Figure 12:
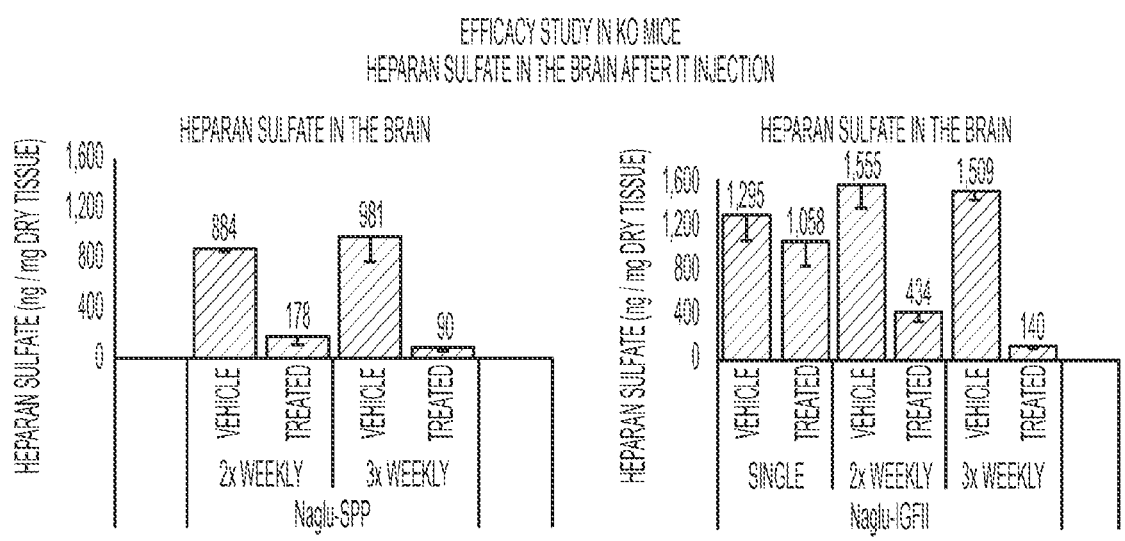
FIG. 12 shows in vivo levels of heparan sulfate (HS) in mouse brains of Naglu knock-out mice following intrathecal delivery of vehicle control, Naglu-SPP or Naglu-IGFII.

In a second assay, we evaluation the total amount of heparan sulfate in the brain of treated KO mice. Heparan sulfate is a specific type of GAG that has been shown to accumulate in the brains of Sanfillipo type B patients. To measure heparan sulfate in mouse brain tissue, a highly sensitive LC/MS method was applied (Lawrence et al, 2012, Nat Chem Biol. 2012 Jan. 8; 8(2):197-204). Briefly, total GAG from brain tissue was extracted by a DEAE column and a desalting column, and then dried and weighted. The extracted GAG was treated with heparin lyases that specifically release unique mono, di and tri saccharides of heparan sulfate, and the sample was then analyzed by LC/MS. The released saccharides were identified and quantified using commercially available saccharide standards of heparan sulfate degradation. Similar to the GAG study describe above, the data illustrate that treatment with Naglu-SPP and Naglu-IGFII leads to a strong reduction in the total amount of heparan sulfate accumulation in brain tissue after 2x weekly and 3x weekly treatment (FIG. 12).

Figure 13A:
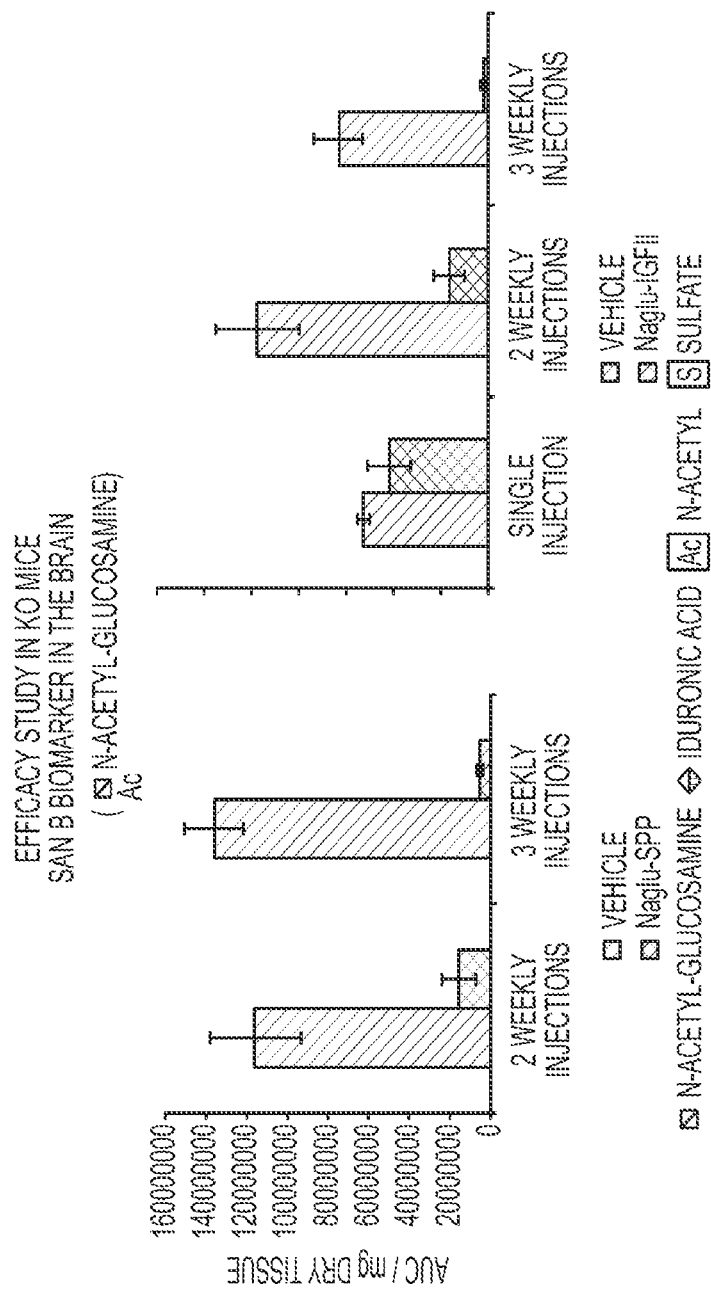
FIGS. 13A-C show in vivo levels of three San B biomarkers in mouse brains of Naglu knock-out mice following intrathecal delivery of vehicle control, Naglu-SPP or Naglu-IGFII.
Figure 13B:
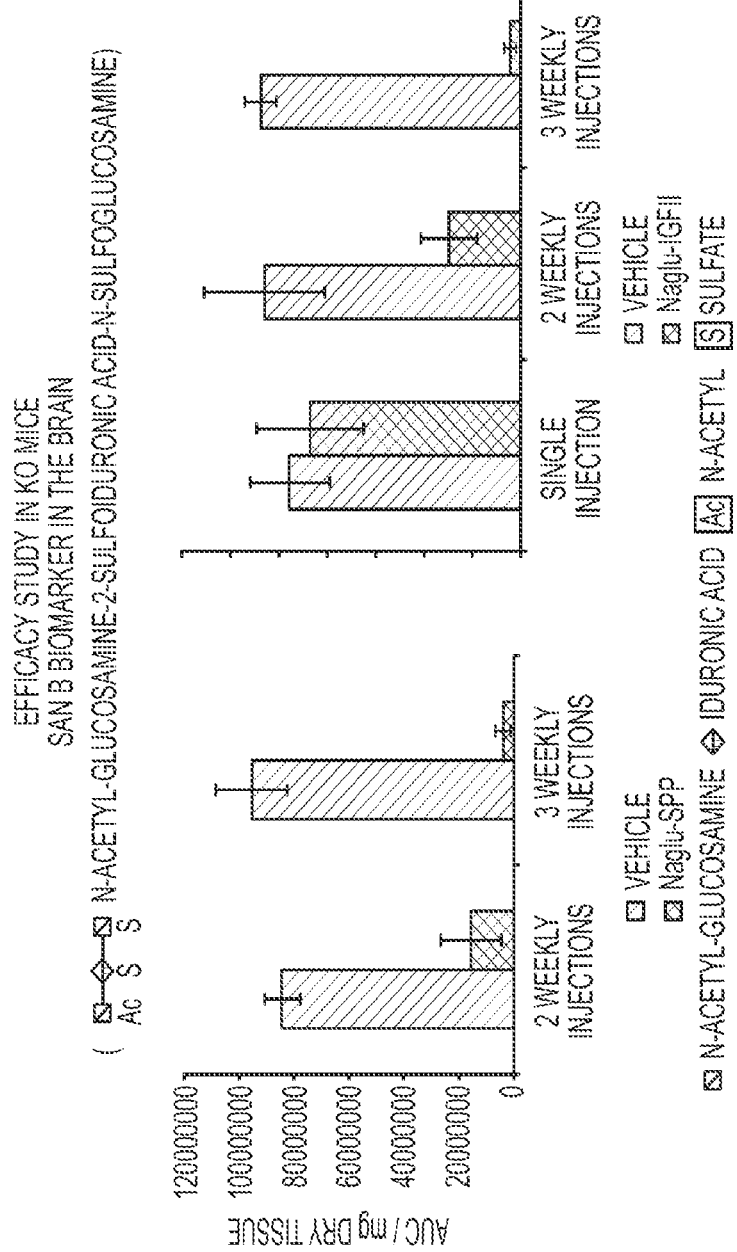
Figure 13C:
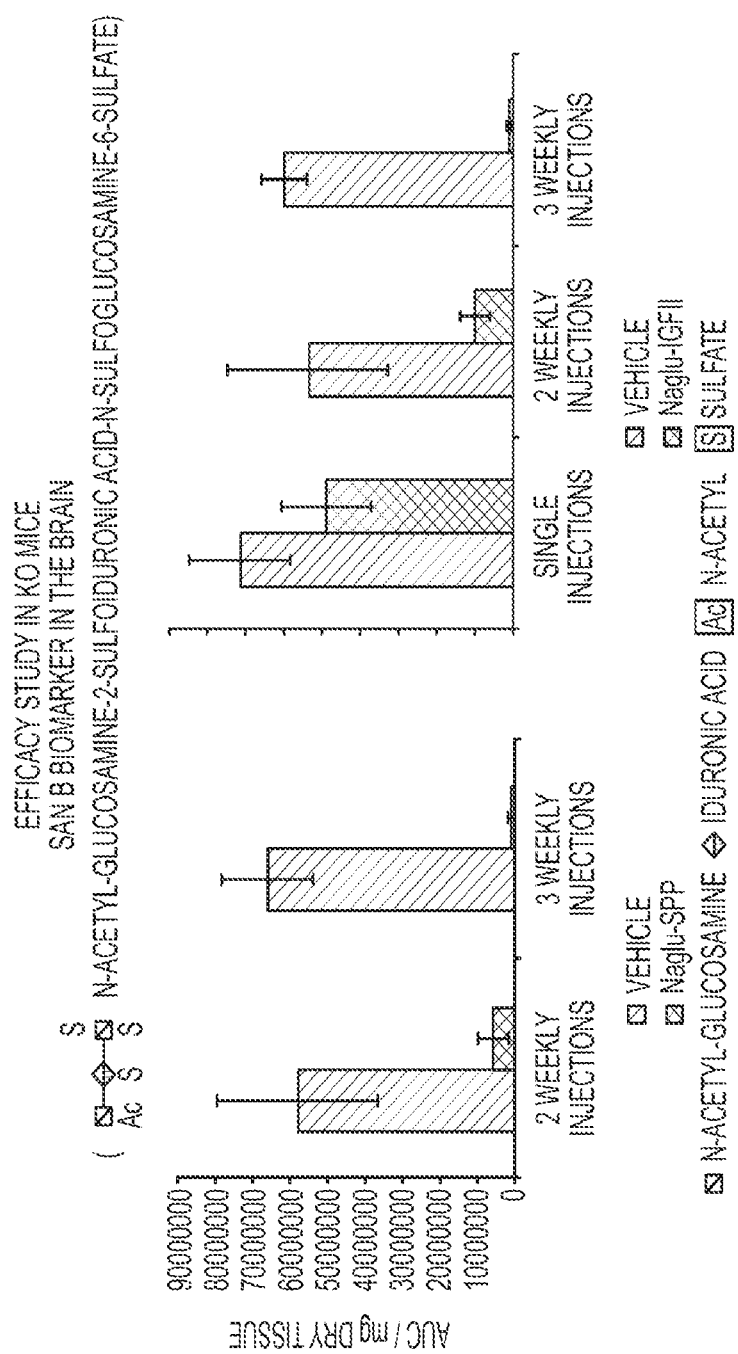

Using the same LC/MS technology as used for the quantification of heparin sulfate (see above), the presence of Sanfillipo B specific biomarkers in brains of treated KO mice were evaluated. Naglu deficiency causes the accumulation of certain heparin sulfate degradation products (presented in FIGS. 13A-C) which are natural substrates of Naglu. These biomarkers are the most relevant indications for Naglu deficiency. The data demonstrates that intrathecal delivery of Naglu-SPP and Naglu-IGFII results in a dramatic decrease in the accumulation of all three GAG cleavage products in the brain (FIGS. 13A-C), especially in the 2x weekly and 3x weekly treatment groups.

Taken together, the above three approaches demonstrate an overall reduction in GAG levels and cleavage products, which suggests that Naglu-SPP is efficiently internalized by neurons and/or glia cell in the brain and targeted to lysosomes, and that targeted Naglu-SPP maintains enzyme activity.

Immunohistochemical Staining of the Liver and Brain of KO Mice after Intrathecal Administration of Naglu-SPP The lysosomal targeting of Naglu-SPP and Naglu-IGFII was further examined by immunohistochemical analysis. Tissue samples were collected, fixed in 10% NBF and processed for paraffin embedding. For each tissue assayed, 5 µm paraffin sections was subjected to immunostaining using antibodies against lamp lysosomal associated membrane protein 1 (Lamp-1), glial fibrillary acidic protein (GFAP) and the ionized calcium-binding adapter molecule 1 (Iba-1).

Figure 14A:
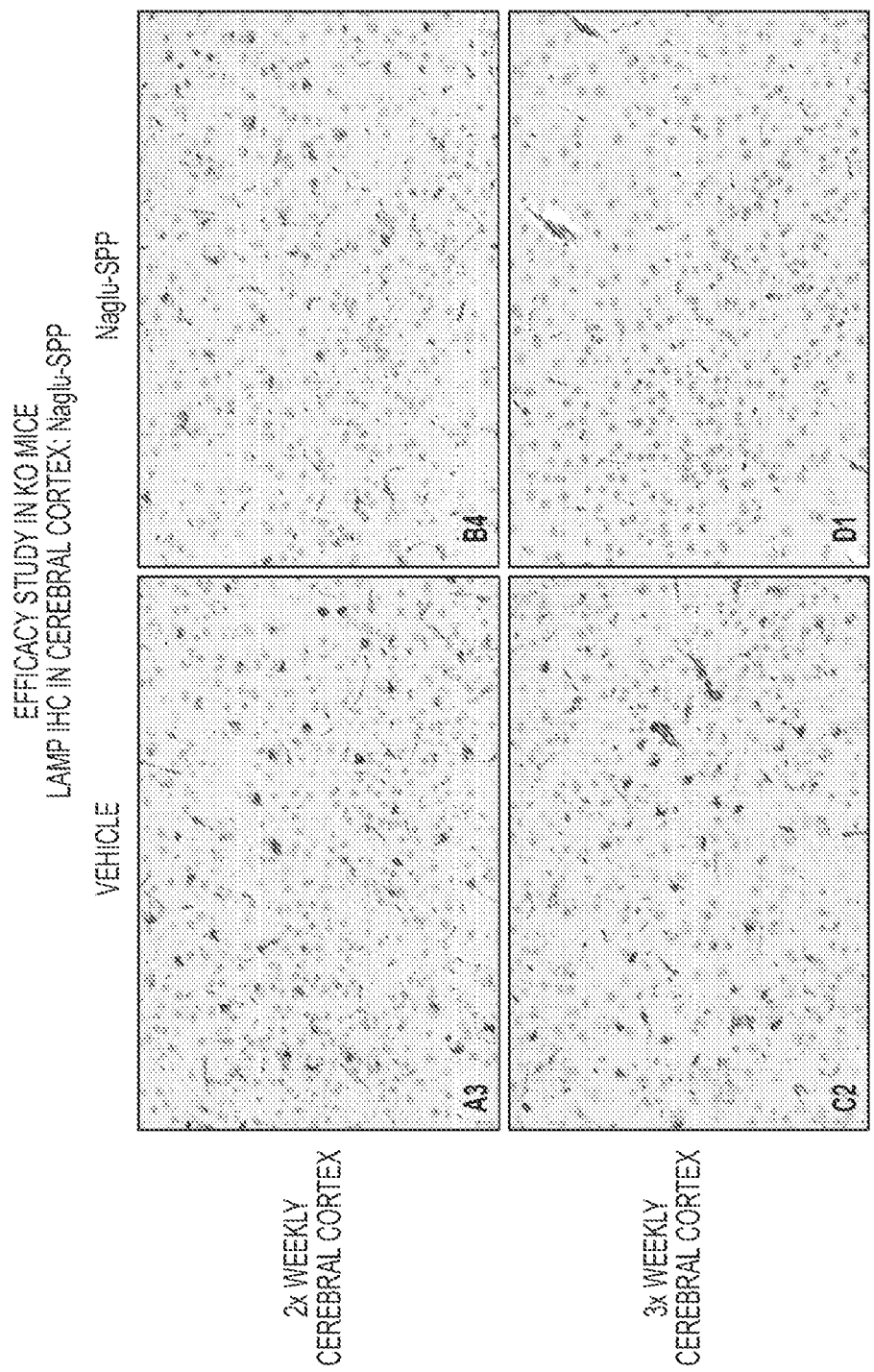
FIGS. 14A-E show LAMP-1 immunohistochemical staining in brain tissues of Naglu knock-out mice following two or three weekly intrathecal deliveries of vehicle control or Naglu-SPP ((A) cerebral cortex, (B) cerebellum, (C) thalamus, (D) striatum and (E) white matter).
Figure 14B:
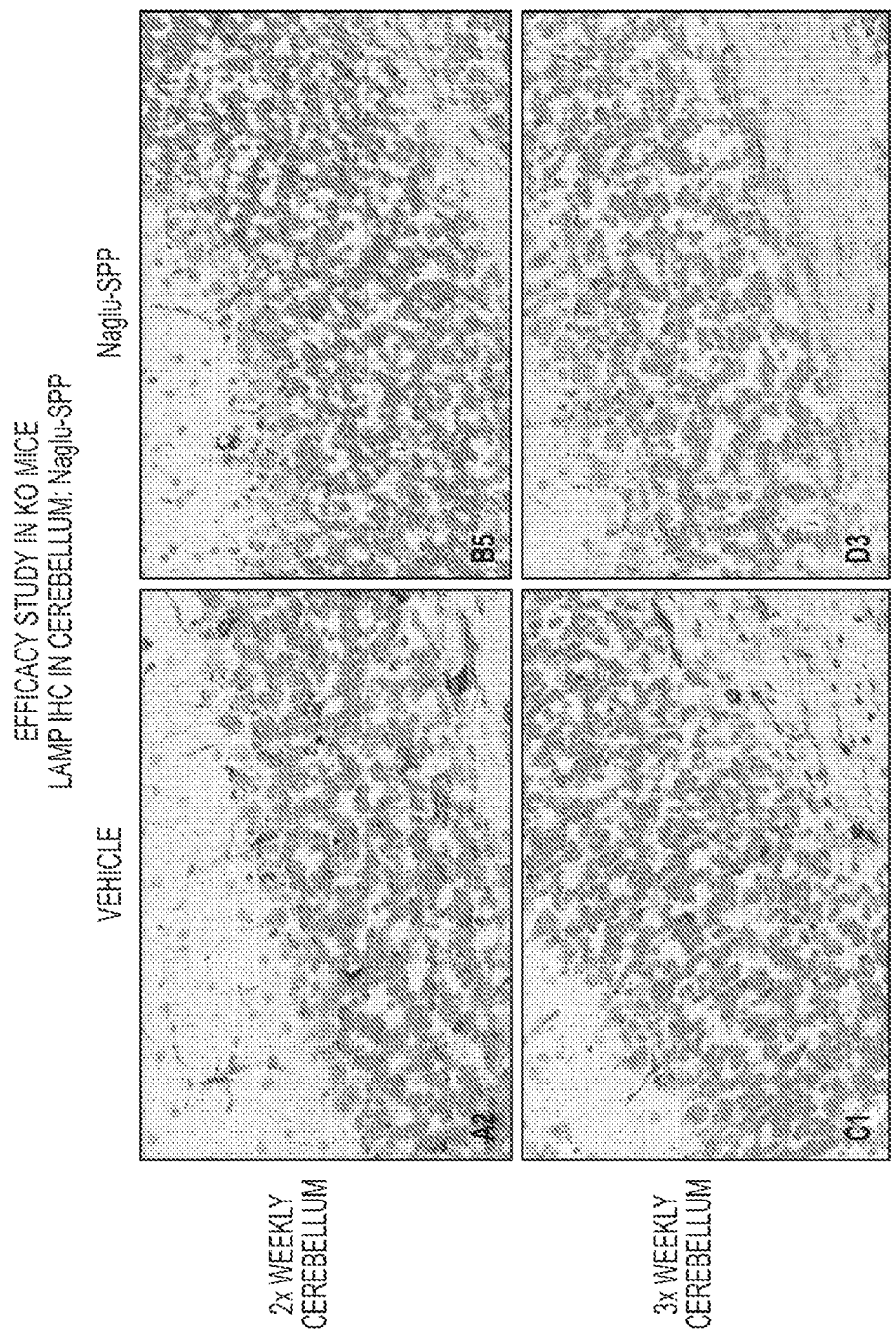
Figure 14C:
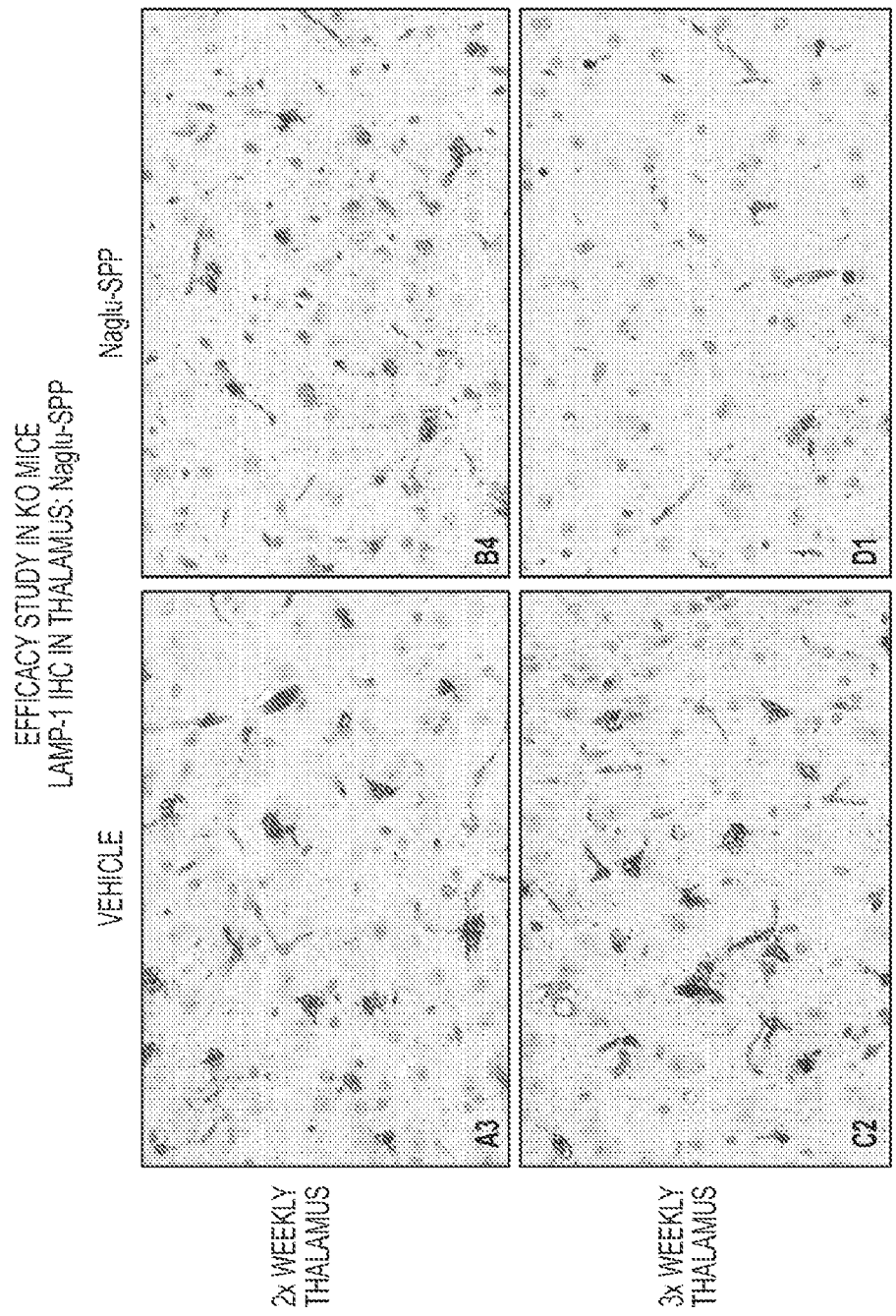
Figure 14D:
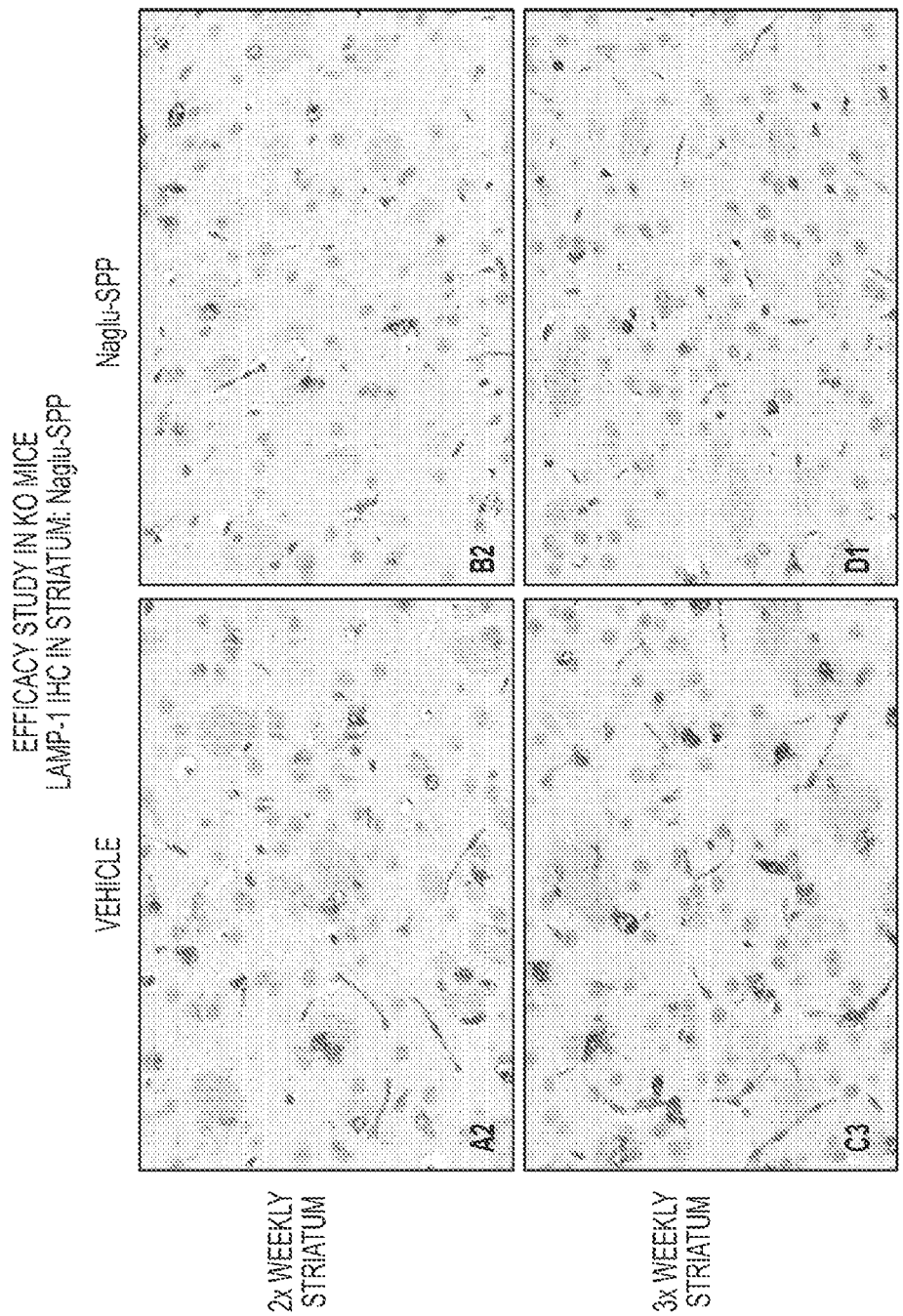
Figure 14E:
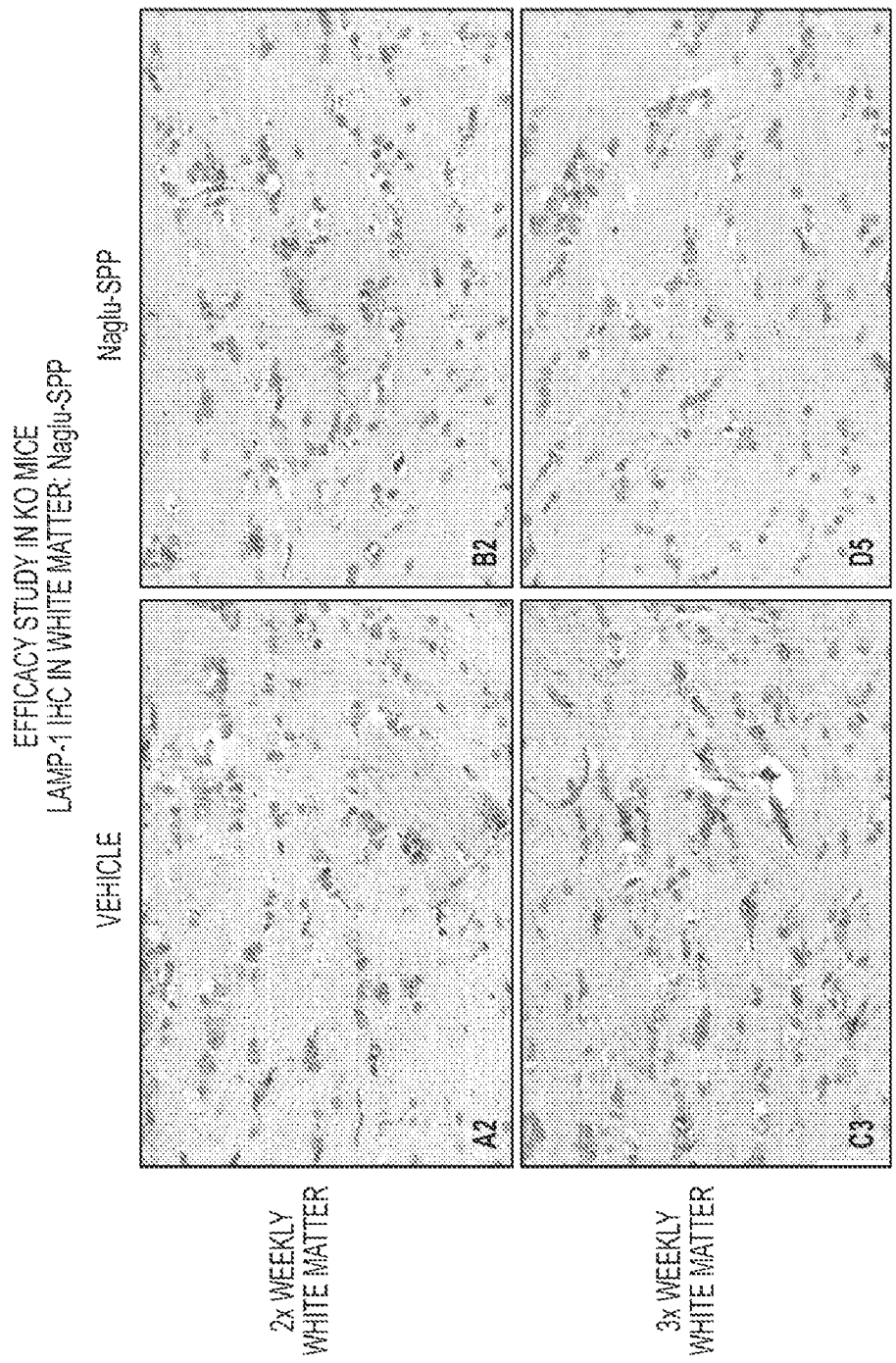
Figure 15:
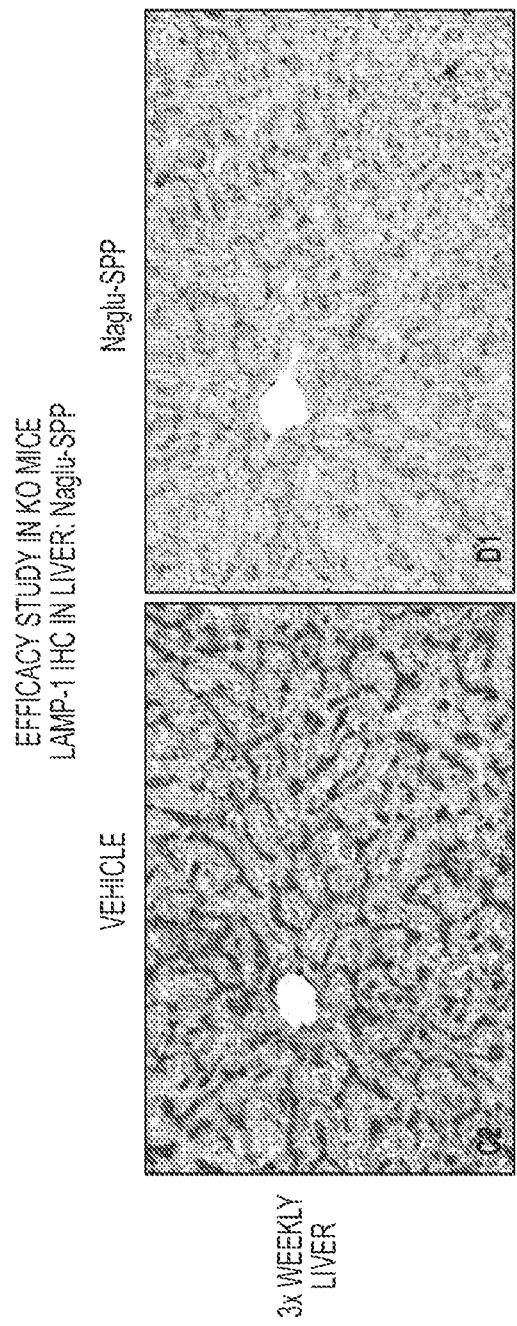
FIG. 15 shows LAMP-1 immunohistochemical staining in liver tissue of Naglu knock-out mice following three weekly intrathecal deliveries of Naglu-SPP.

To further elucidate and confirm intracellular delivery and lysosomal entry of Naglu-SPP, the inventors examined Lamp-1 immunoreactivity for each experimental treatment group. Lamp-1 is a lysosomal specific protein the intracellular distribution of which can be used to monitor lysosome size and number of processes. Vehicle control mice showed an increased level of Lamp-1 immunoreactivity, as is indicated by the increased number and size of lysosomes detected in cerebral cortex tissue (FIG. 14A). In contrast, intrathecal delivery of Naglu-SPP resulted in a decrease in Lamp-1 immonostaining in mice treated 2× weekly and 3× weekly (FIG. 14A). This dramatic overall reduction in lysosome size and number of processes, as compared to vehicle control was consistently observed in various other areas of the brain of Naglu-SPP treated KO mice, such as cerebellum (FIG. 14B); thalamus (FIG. 14C); striatum (FIG. 14D); and white matter (FIG. 14E). Lamp-1 immunoreactivity was also reduced significantly in the liver (FIG. 15) of KO mice treated with Naglu-SPP.

Figure 16:
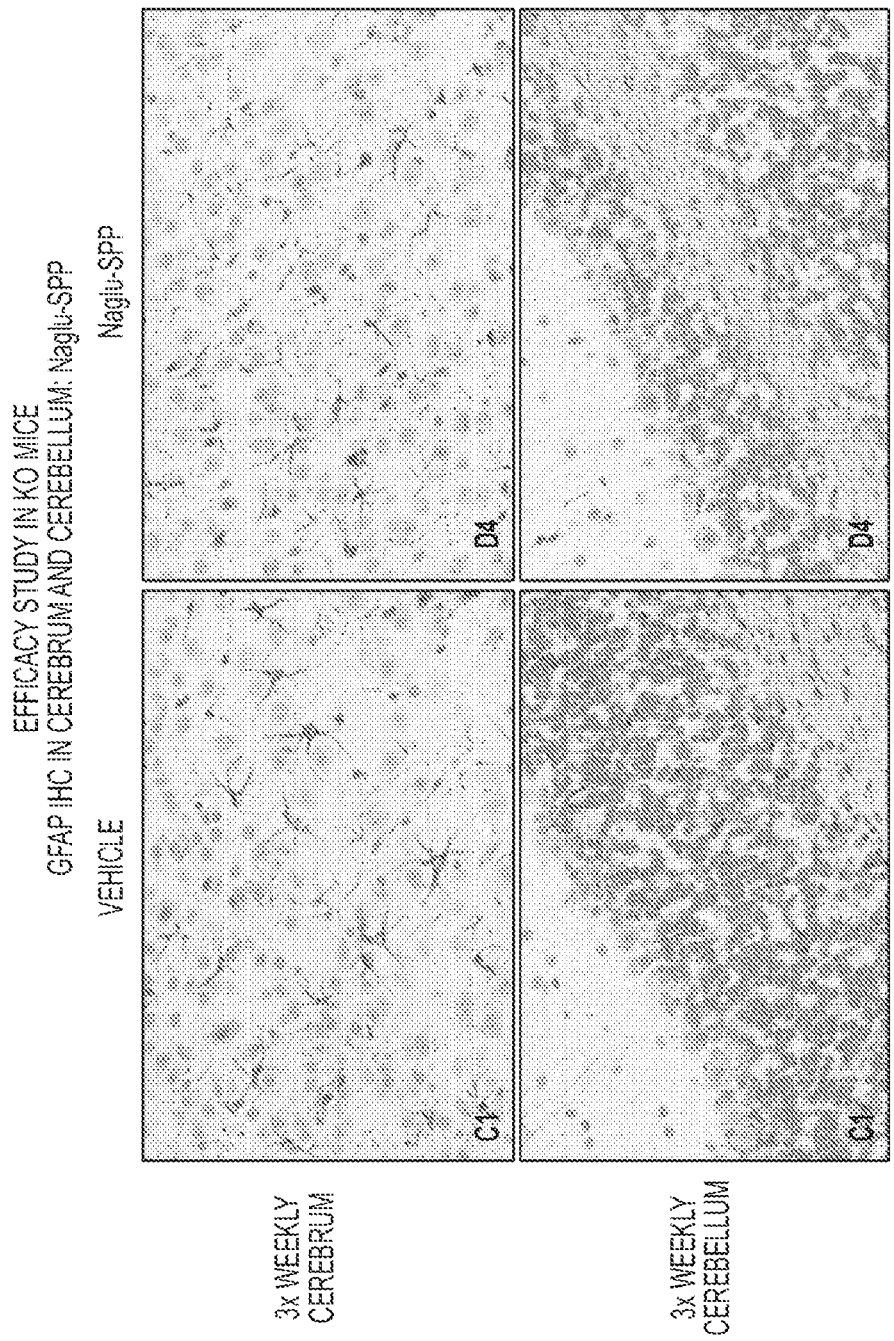
FIG. 16 shows immunohistochemical staining of GFAP in cerebrum and cerebellum tissues of Naglu knock-out mice following three weekly intrathecal injections of vehicle control or Naglu-SPP.
Figure 17:
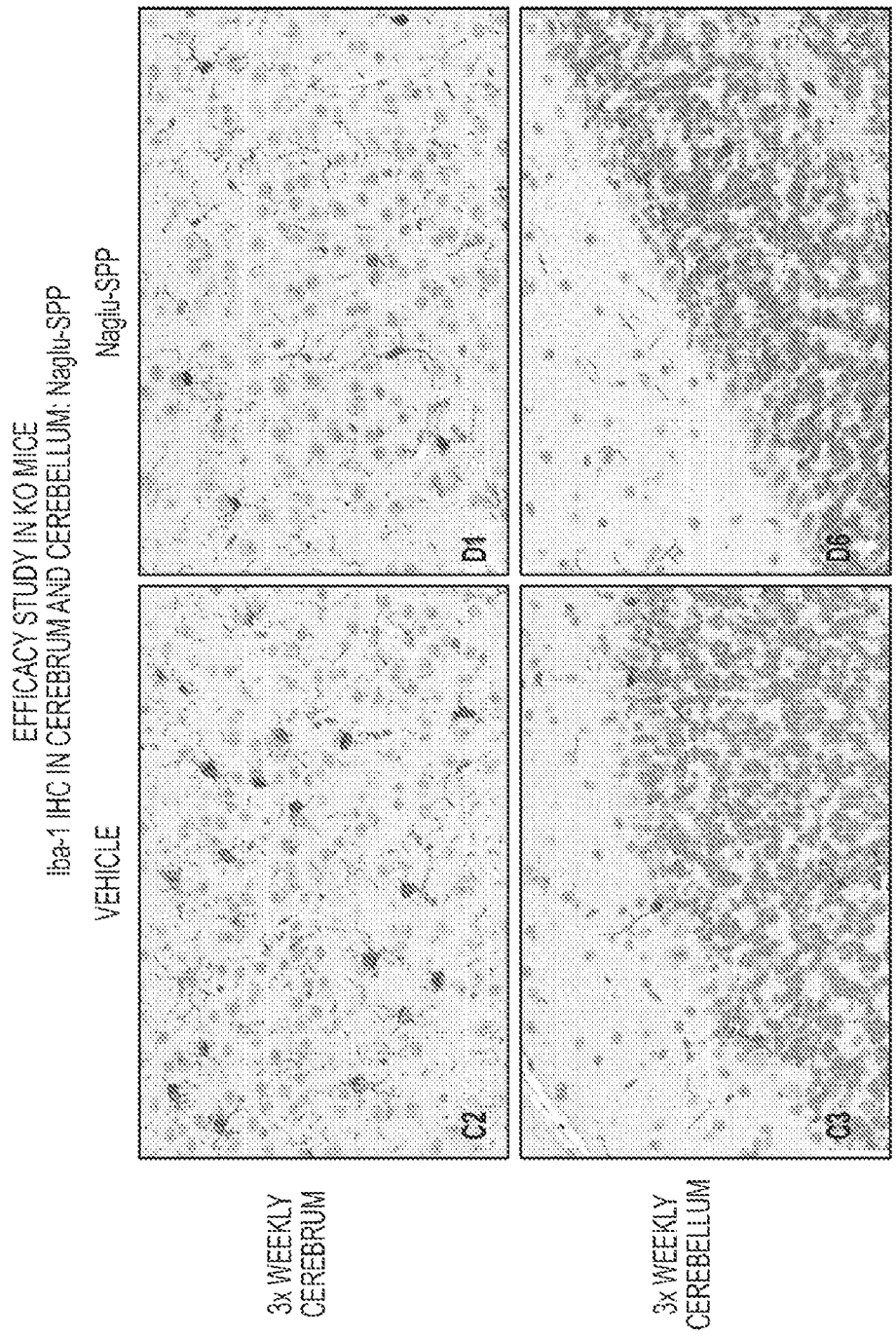
FIG. 17 shows immunohistochemical staining of Iba-1 in cerebrum and cerebellum tissue of Naglu knock-out mice following three weekly intrathecal injections of vehicle control or Naglu-SPP.

Two additional cellular biomarkers were used to further evaluate efficacy of Naglu-SPP treatment of KO mice, i.e., glial fibrillary acidic protein (GFAP) and the ionized calcium-binding adapter molecule 1 (Iba-1). Each protein is a well-established indicator of cellular inflammatory response and can be used to gauge the level and intensity of inflammation in specific cell types. In particular, GFAP staining has been used extensively to demonstrate the size and number of processes in astrocytes, while Iba-1 staining is predominantly used for evaluating microglial cells. As shown in FIG. 16, mice subjected to intrathecal delivery of Naglu-SPP have a reduced signal in GFAP staining in the cerebral cortex and the cerebellum and a reduced number of astrocyte size with a reduced number of processes. A similar trend was also observed with respect to Iba-1 staining in the cerebral cortex and the cerebellum (FIG. 17); microglial cells are reduced in size and have a smaller number of processes.

Figure 18A:
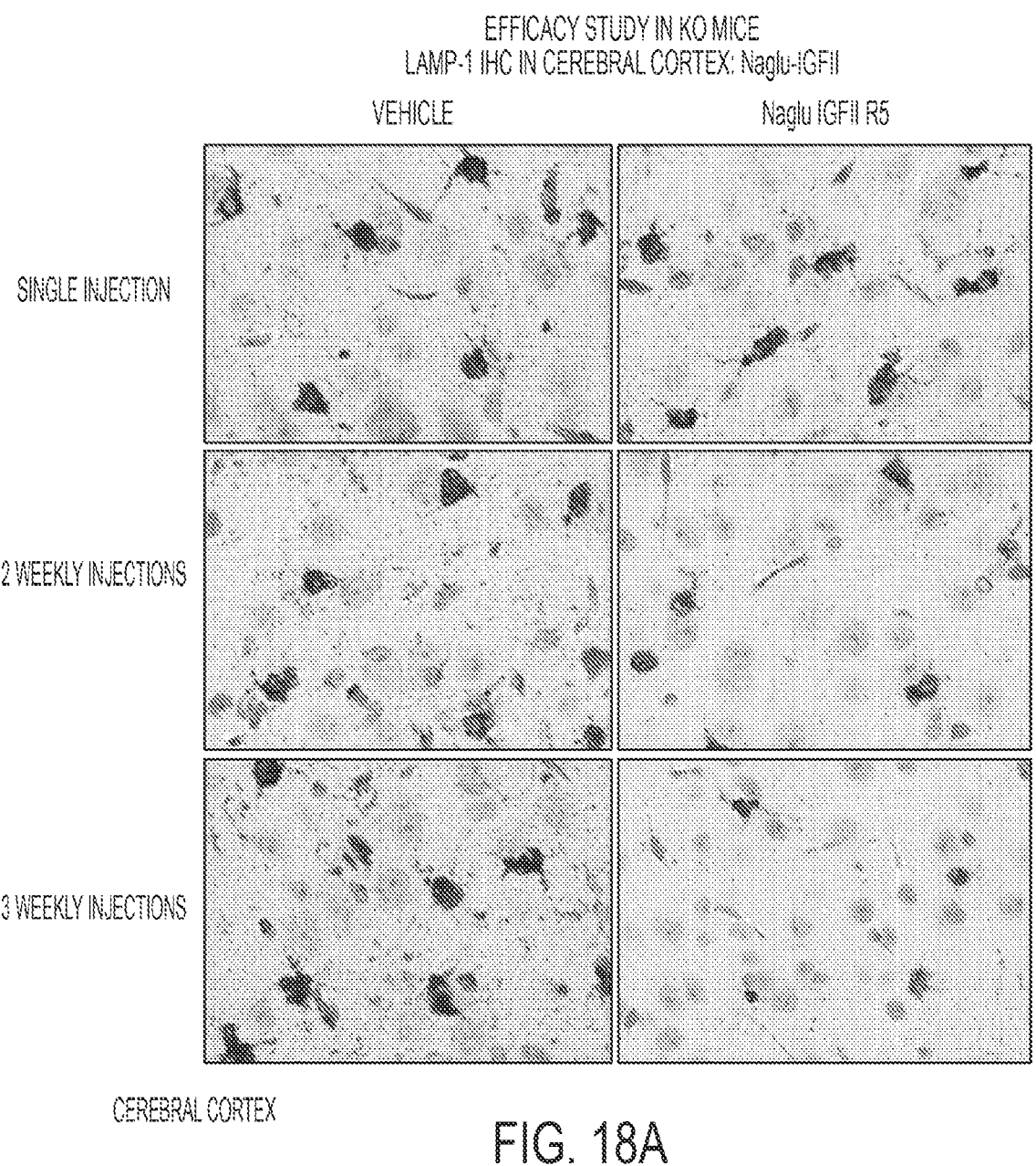
FIG. 18A-E shows LAMP-1 immunohistochemical staining in brain tissues of Naglu knock-out mice following two or three weekly intrathecal injections of vehicle control or Naglu-IGFII ((A) cerebral cortex, (B) cerebellum, (C) thalamus, (D) striatum and (E) white matter).
Figure 18B:
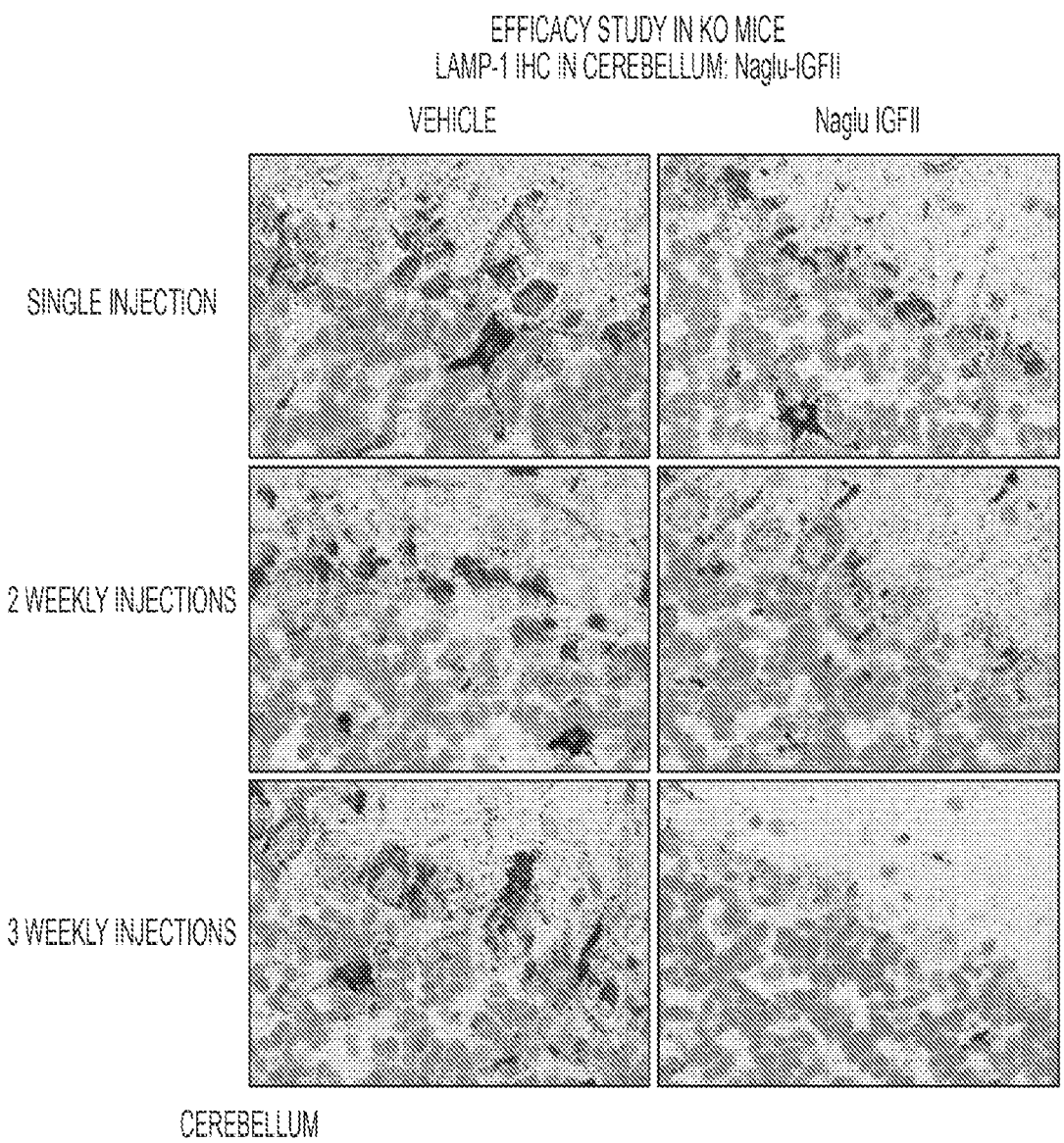
Figure 18C:
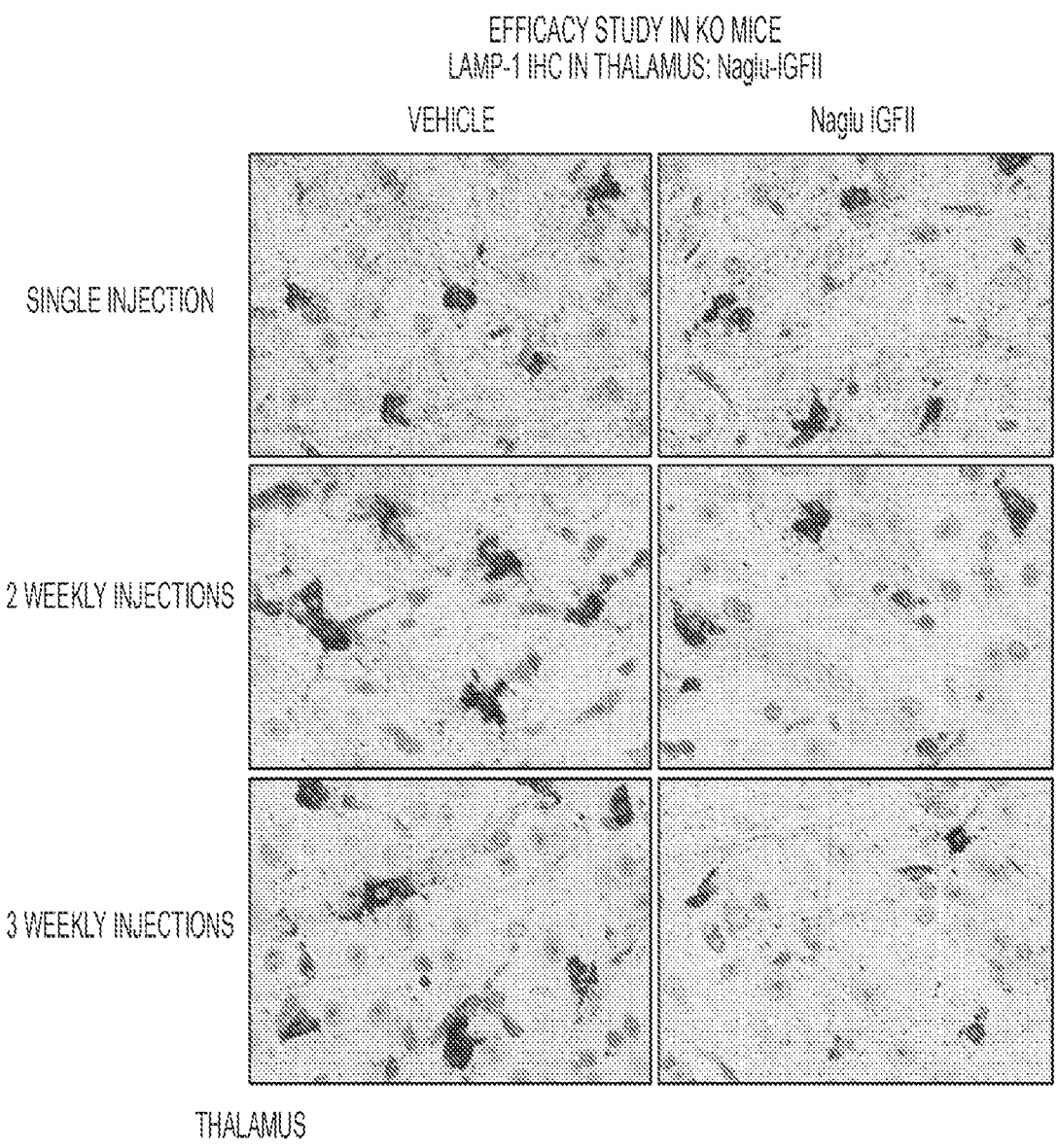
Figure 18D:
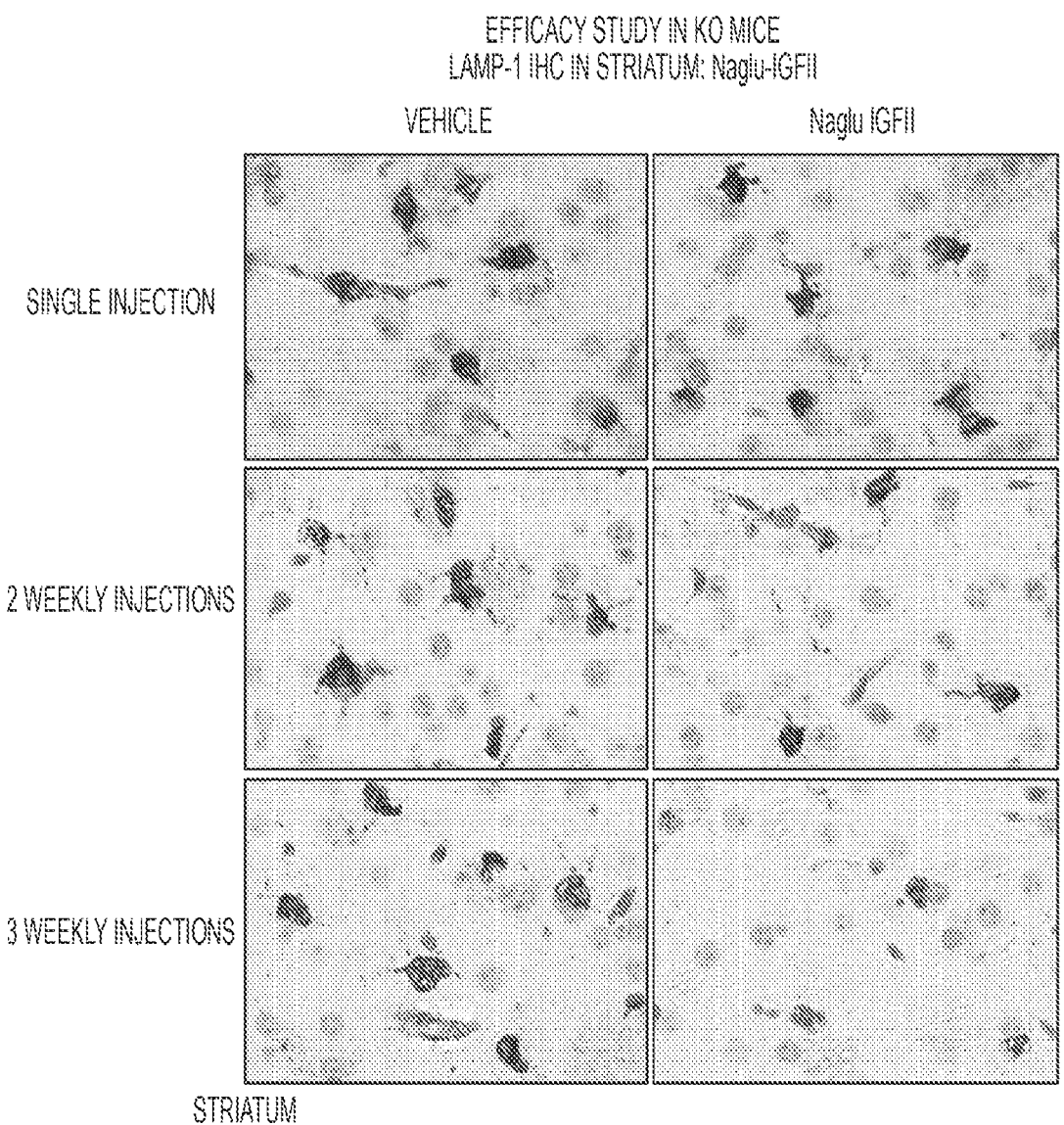
Figure 18E:
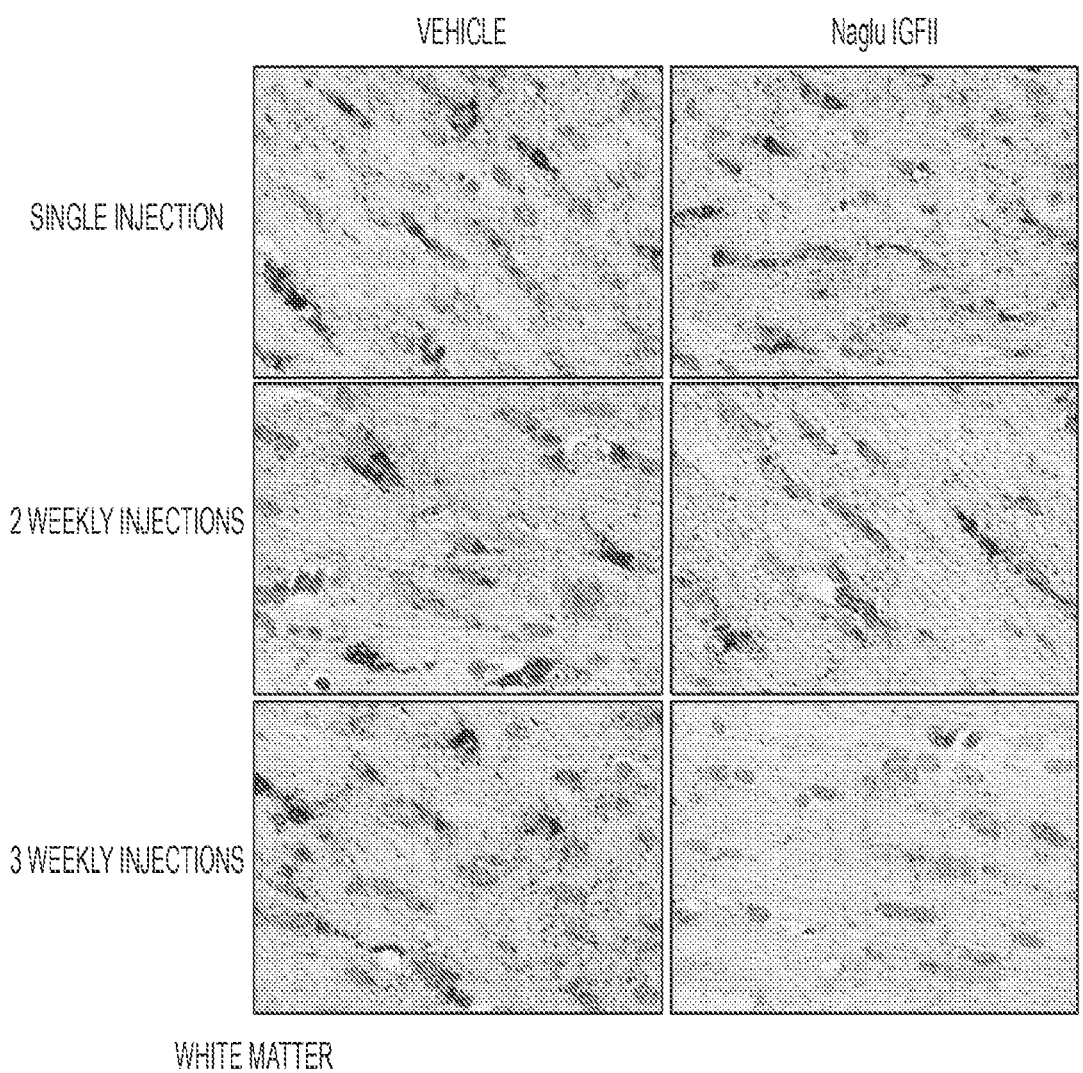
Figure 19:
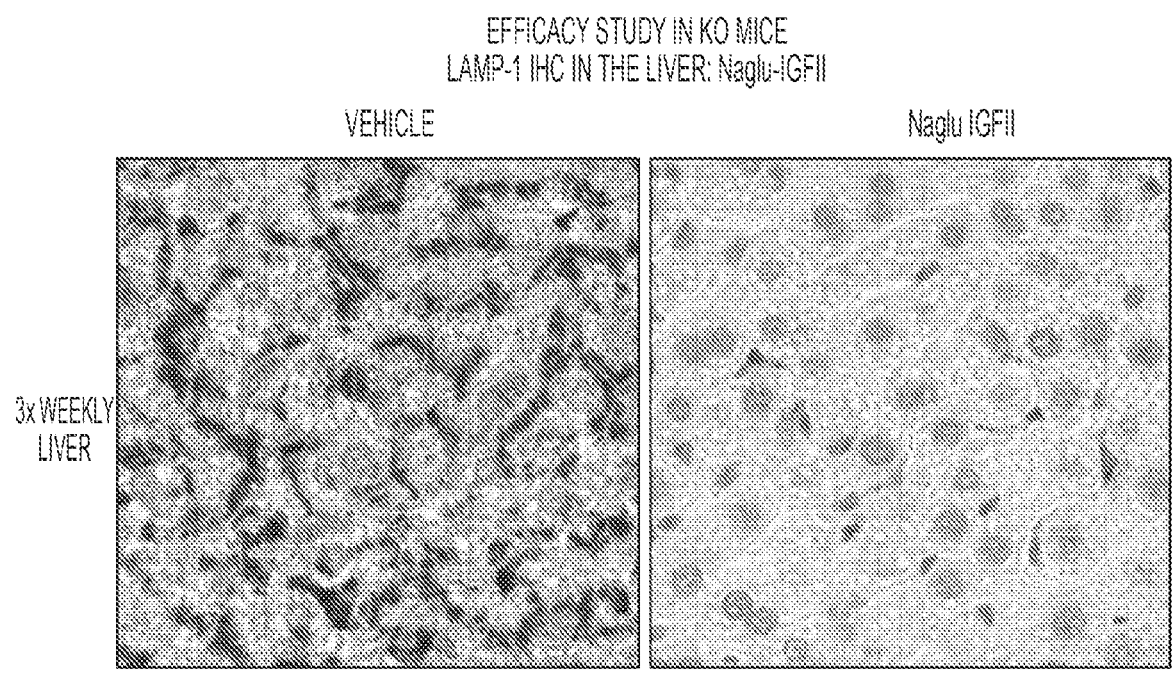
FIG. 19 shows LAMP-1 immunohistochemical staining in liver tissue of Naglu knock-out mice following three weekly intrathecal injections of vehicle control or Naglu-IGFII.

The efficacy of intrathecal delivery of Naglu-IGFII was analyzed in the same way that delivery of Naglu-SPP was analyzed. Administration of Naglu-IGFII resulted in a decrease in Lamp-1 immonostaining in both treatment groups (FIG. 18A). The dramatic overall reduction in lysosome size and number of lysosomal processes, as compared to vehicle control, was consistently observed in various areas of the brain of KO mice, such as cerebellum (FIG. 18B); thalamus (FIG. 18C); striatum (FIG. 18D); and white matter (FIG. 18E). Lamp-1 immunoreactivity was also reduced significantly in the liver (FIG. 19) of Naglu-IGFII treated KO mice.

Figure 20:
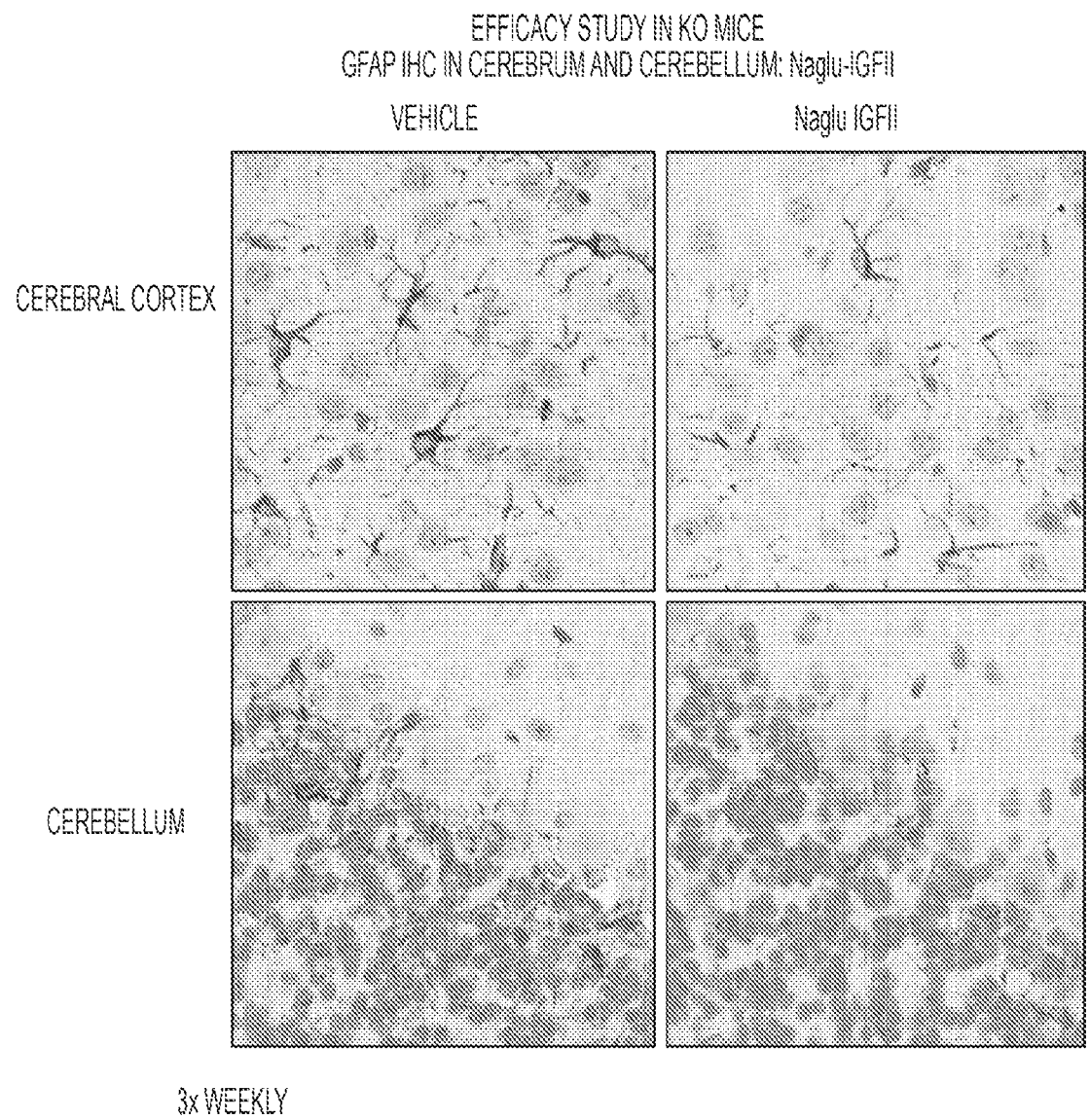
FIG. 20 shows immunohistochemical staining of GFAP in cerebrum and cerebellum tissues of Naglu knock-out mice following three weekly intrathecal injections of vehicle control or Naglu-IGFII.
Figure 21:
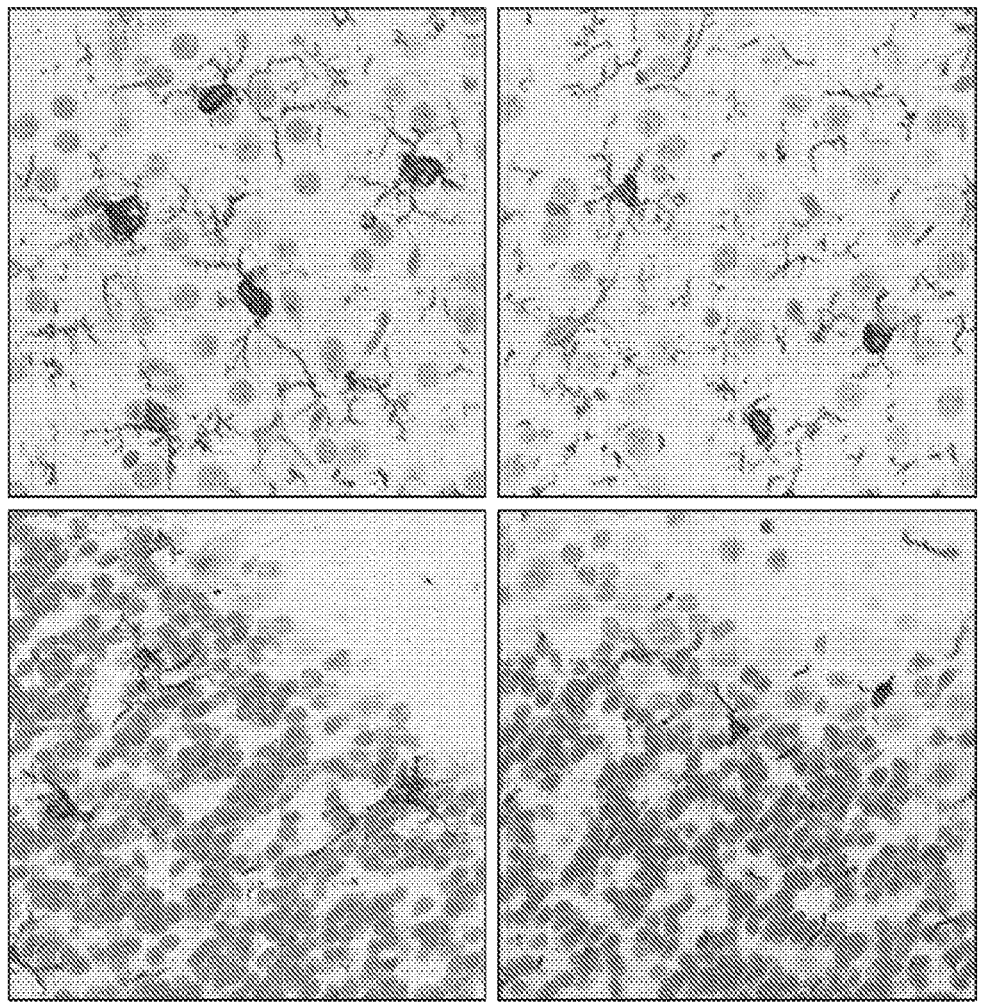
FIG. 21 shows immunohistochemical staining of Iba-1 cerebrum and cerebellum tissue of Naglu knock-out mice following three weekly intrathecal injections of vehicle control or Naglu-IGFII.

Mice subjected to intrathecal delivery of Naglu-IGFII also had a reduced signal in GFAP staining in the cerebral cortex and the cerebellum, and the size of astrocytes was reduced and the number of their processes diminished (FIG. 20). A similar trend was also observed with respect to Iba-1 staining in the cerebral cortex and the cerebellum of analyzed KO mice (FIG. 21); microglial cells had a reduced size and a reduced number of processes.

The above described data provide strong in vivo support that Naglu-SPP binds to SORT1, enters various cells types and is targeted to lysosomes. Surprisingly, intrathecally delivered Naglu-SPP is widely bioavailable throughout the body and localized in neuronal tissue as well as various other organ systems, such as the liver. The data further suggest that upon entry into the cell, the Naglu-SPP fusion protein maintains enzyme activity and proper function, as demonstrated by the overall reduction in excess accumulation of glucosaminoglycans, heparan sulfate and biomarkers specific for Sanfilippo type B in Naglu knockout mice. Our data show that Naglu-SPP fusion proteins have excellent efficacy, biodistribution and ability to enter lysosomes via the SORT1 pathway. Our data also show that Naglu-SPP is overall as effective as Naglu-IGFII in terms of its targeting to lysosomes of neurons and glia cells in the brain and its bioactivity in vivo.

The above suggests that the use of Naglu-SPP could be extremely effective with respect to enzyme replacement therapy in humans. Since SORT1-derived peptides can be used in conjunction with any lysosomal enzyme, our data indicate that our invention is applicable to the treatment by enzyme replacement therapy of any lysosomal storage disease.

We claim:

1. A targeted fusion protein comprising:
   a lysosomal enzyme; and
   a lysosomal targeting moiety that comprises a Sortilin-1 receptor propeptide (SPP) comprising an amino acid sequence at least 95% identical to SEQ ID NO: 4.

2. The targeted fusion protein of claim 1, wherein the lysosomal enzyme comprises an amino acid sequence identical to SEQ ID NO: 1.

3. The targeted fusion protein of claim 1, wherein the SPP comprises SEQ ID NO:4.

4. The targeted fusion protein of claim 1, wherein the lysosomal targeting moiety and the lysosomal enzyme are fused via a linker.

5. The targeted fusion protein of claim 4, wherein the linker comprises a sequence of

GAPGGGGGAAAAAGGGGGAPGGGGGAAAAAGGGGGAPGGGGGAAAAAGGGGGAP,

6. The targeted fusion protein of claim 1, wherein the targeted fusion protein comprises a sequence at least 80% identical to the amino acid sequence of SEQ ID NO: 17.

7. The targeted fusion protein of claim 1, wherein the targeted fusion protein comprises a sequence at least 80% identical to the amino acid sequence of SEQ ID NO: 22.

* * * * *